US012311151B2

(12) United States Patent
Finkelstein et al.

(10) Patent No.: US 12,311,151 B2
(45) Date of Patent: May 27, 2025

(54) DRUG DELIVERY DEVICE

(71) Applicant: AMGEN INC., Thousand Oaks, CA (US)

(72) Inventors: Emil Finkelstein, Frederiksberg (DK); Soren Forbech Skall, Søborg (DK); Lars Eilertsen, Søborg (DK); Matias Melander, Copenhagen (DK); Jan Jensen, Copenhagen (DK)

(73) Assignee: AMGEN INC., Thousand Oaks, CA (US)

( * ) Notice: Subject to any disclaimer, the term of this patent is extended or adjusted under 35 U.S.C. 154(b) by 0 days.

(21) Appl. No.: 18/534,155

(22) Filed: Dec. 8, 2023

(65) Prior Publication Data
US 2024/0100258 A1  Mar. 28, 2024

Related U.S. Application Data

(63) Continuation of application No. 17/036,129, filed on Sep. 29, 2020, now Pat. No. 11,878,149.
(Continued)

(51) Int. Cl.
*A61M 5/315* (2006.01)
*A61M 5/20* (2006.01)
(Continued)

(52) U.S. Cl.
CPC .......... *A61M 5/31536* (2013.01); *A61M 5/20* (2013.01); *A61M 5/3137* (2013.01);
(Continued)

(58) Field of Classification Search
CPC .. A61M 5/31536; A61M 5/20; A61M 5/3137; A61M 5/3157; A61M 5/3204;
(Continued)

(56) References Cited

U.S. PATENT DOCUMENTS

| 3,494,358 A | 2/1970 | Fehlis et al. |
| 4,717,383 A | 1/1988 | Phillips et al. |

(Continued)

FOREIGN PATENT DOCUMENTS

| EP | 0734738 B1 | 10/2003 |
| EP | 1259274 B1 | 11/2006 |

(Continued)

OTHER PUBLICATIONS

First Office Action received in related Eurasian Patent Application No. 202291044, dated Dec. 2, 2022.
(Continued)

*Primary Examiner* — Tasnim Mehjabin Ahmed

(57) ABSTRACT

A drug delivery device may include a housing defining a longitudinal axis and having an opening and a drug storage container including a delivery member having an insertion end configured to extend at least partially through the opening during a delivery state. The device may also include plunger moveable toward the distal end of the drug storage container to expel a drug from the drug storage container through the delivery member, the plunger including a body portion having an inner wall defining an axial chamber and an outer wall cooperating with the inner wall to define a body thickness. The device may further include a plunger biasing member disposed at least partially within the axial chamber, the plunger biasing member configured to urge the plunger toward the distal end of the drug storage container.

25 Claims, 43 Drawing Sheets

Related U.S. Application Data

(60) Provisional application No. 62/961,031, filed on Jan. 14, 2020, provisional application No. 62/908,504, filed on Sep. 30, 2019.

(51) Int. Cl.
*A61M 5/31* (2006.01)
*A61M 5/32* (2006.01)

(52) U.S. Cl.
CPC ......... *A61M 5/3157* (2013.01); *A61M 5/3204* (2013.01); *A61M 2205/581* (2013.01); *A61M 2205/582* (2013.01)

(58) Field of Classification Search
CPC .............. A61M 5/3271; A61M 5/2033; A61M 5/31511; A61M 2005/2013; A61M 2005/3247; A61M 2005/3267; A61M 2205/581; A61M 2205/582
See application file for complete search history.

(56) References Cited

U.S. PATENT DOCUMENTS

| | | | |
|---|---|---|---|
| 4,902,279 | A | 2/1990 | Schmidtz et al. |
| 4,946,446 | A | 8/1990 | Vadher |
| 5,593,388 | A | 1/1997 | Phillips |
| 5,599,309 | A | 2/1997 | Marshall et al. |
| 5,681,291 | A | 10/1997 | Galli |
| 5,709,662 | A | 1/1998 | Olive et al. |
| 6,120,479 | A * | 9/2000 | Campbell ............. A61M 5/508 604/110 |
| 6,183,446 | B1 | 2/2001 | Jeanbourquin |
| 6,620,137 | B2 | 9/2003 | Kirchhofer et al. |
| 6,676,641 | B2 | 1/2004 | Woodard, Jr. et al. |
| 7,112,187 | B2 | 9/2006 | Karlsson |
| 7,597,685 | B2 | 10/2009 | Olson |
| 8,591,465 | B2 | 11/2013 | Hommann |
| 8,932,254 | B2 | 1/2015 | Eaton |
| 9,408,976 | B2 | 8/2016 | Olson et al. |
| 11,878,149 | B2 * | 1/2024 | Finkelstein ......... A61M 5/2033 |
| 2005/0165353 | A1 | 7/2005 | Pessin |
| 2006/0264830 | A1 * | 11/2006 | Hommann .......... A61M 5/2033 604/136 |
| 2011/0218500 | A1 | 9/2011 | Grunhut et al. |
| 2012/0123350 | A1 | 5/2012 | Giambattista et al. |
| 2013/0281938 | A1 | 10/2013 | Ekman et al. |
| 2013/0317432 | A1 * | 11/2013 | Fabien ................ A61M 5/3157 604/131 |
| 2016/0089498 | A1 | 3/2016 | Daniel |
| 2017/0246400 | A1 | 8/2017 | Stefanov et al. |
| 2018/0193562 | A1 | 7/2018 | Gibson et al. |
| 2018/0296767 | A1 | 10/2018 | Säll |
| 2018/0315345 | A1 | 11/2018 | Daniel |
| 2019/0050375 | A1 | 2/2019 | Fitzgibbon et al. |

FOREIGN PATENT DOCUMENTS

| | | |
|---|---|---|
| EP | 2823838 A1 | 1/2015 |
| EP | 2823840 A1 | 1/2015 |
| EP | 2438948 B1 | 3/2016 |
| EP | 2781230 B1 | 8/2019 |
| JP | 2007509657 A | 4/2007 |
| JP | 4699192 B2 | 6/2011 |
| JP | 2016523672 A | 8/2016 |
| WO | 2004028598 A1 | 4/2004 |
| WO | 2010084306 A2 | 7/2010 |
| WO | 2011047298 A2 | 4/2011 |
| WO | 2012022810 A2 | 2/2012 |
| WO | 2012032411 A2 | 3/2012 |
| WO | 2012045350 A1 | 4/2012 |
| WO | 2015004052 A1 | 1/2015 |
| WO | 2016193374 A1 | 12/2016 |
| WO | 2017071909 A1 | 5/2017 |
| WO | 2018107270 A1 | 6/2018 |
| WO | 2018166985 A1 | 9/2018 |
| WO | 2019081578 A1 | 5/2019 |

OTHER PUBLICATIONS

Second Office Action received in related Eurasian Patent Application No. 202291044 dated Jun. 27, 2023.
International Application No. PCT/US2020/053180, International Search Report and Written Opinion, mailed Dec. 8, 2020.
International Application No. PCT/US2020/053178, International Search Report and Written Opinion, mailed Dec. 17, 2020.
International Application No. PCT/US2020/053179, International Search Report and Written Opinion, mailed Jan. 12, 2021.
International Application No. PCT/US2020/053176, International Search Report and Written Opinion, mailed Jan. 13, 2021.
International Application No. PCT/US2020/070591, International Search Report and Written Opinion, mailed Mar. 26, 2021.
Office Action received in counterpart Chinese Patent Application No. 202080067398.4, dated Jan. 27, 2024.
First Examination Report received in counterpart Saudi Arabia Patent Application No. 522432121, dated Jun. 6, 2024.
Search Report received in counterpart Eurasian Patent Application No. 202490359, dated Jun. 10, 2024.
Office Action received in counterpart Japanese Patent Application No. 2022-519218, dated Sep. 17, 2024.
Second Examination Report received in counterpart Saudi Arabia Patent Application No. 522432121, dated Dec. 5, 2024.
Second Office Action received in counterpart Japanese Patent Application No. 2022-519218, dated Mar. 11, 2025.

* cited by examiner

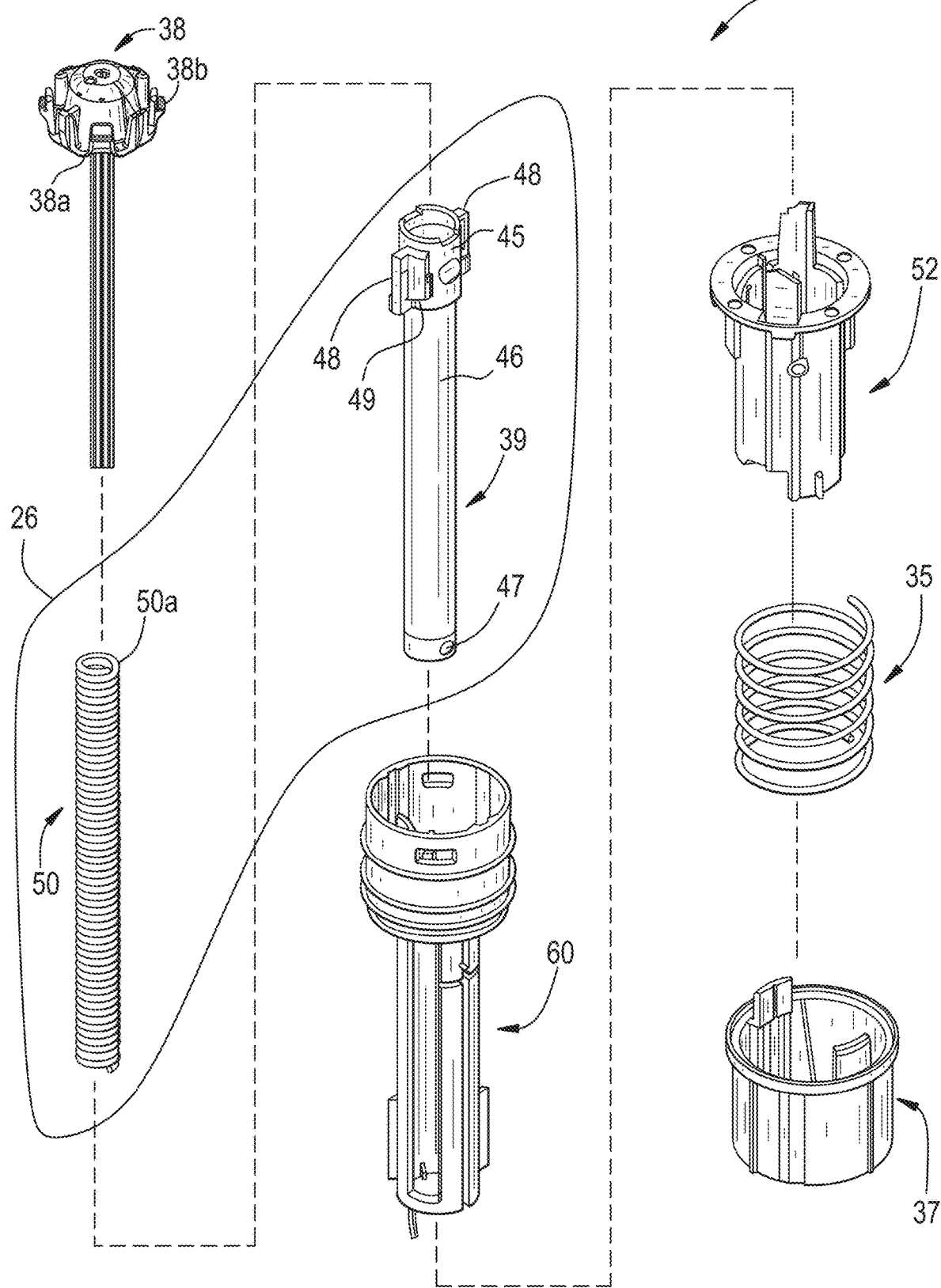

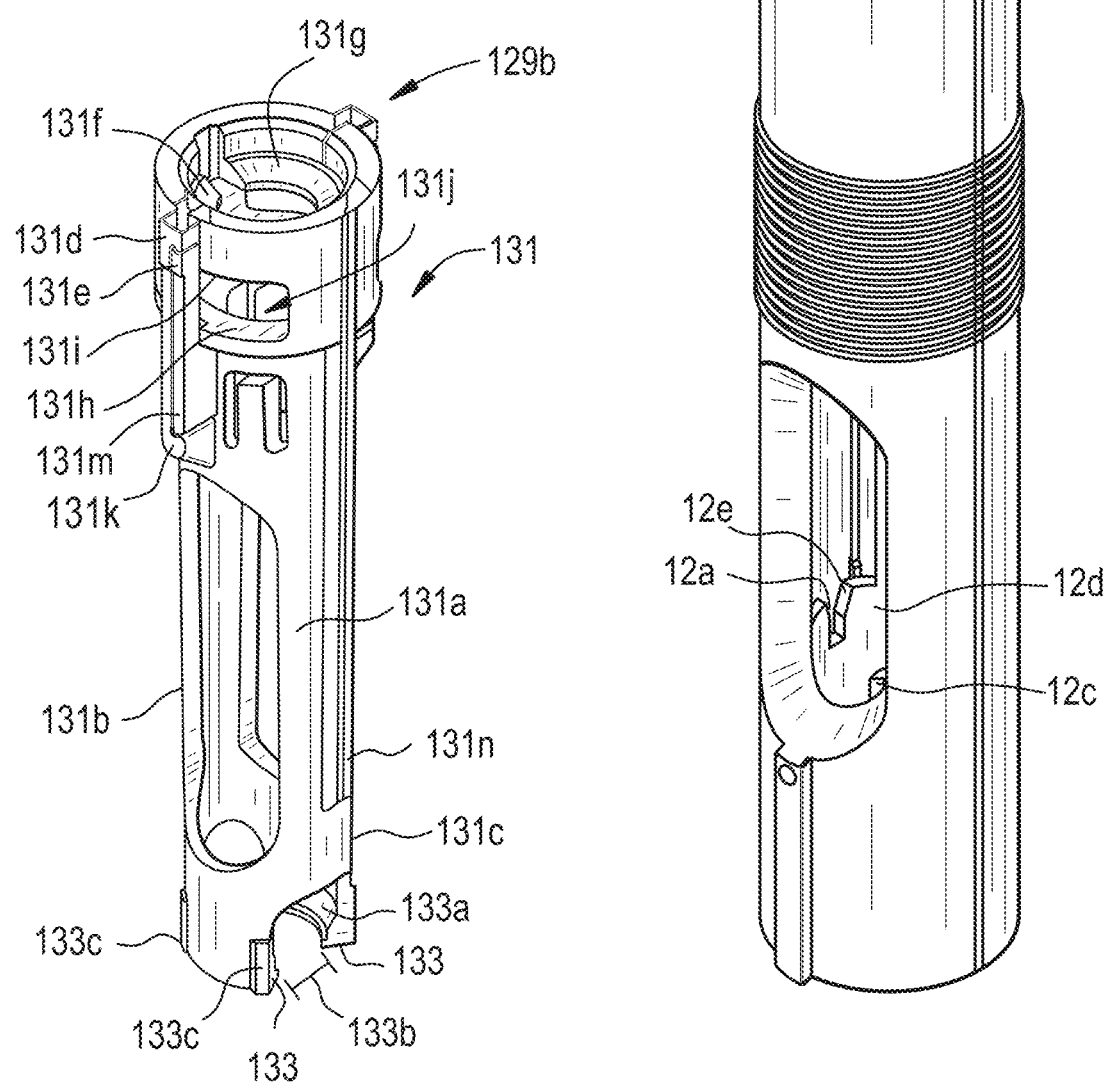

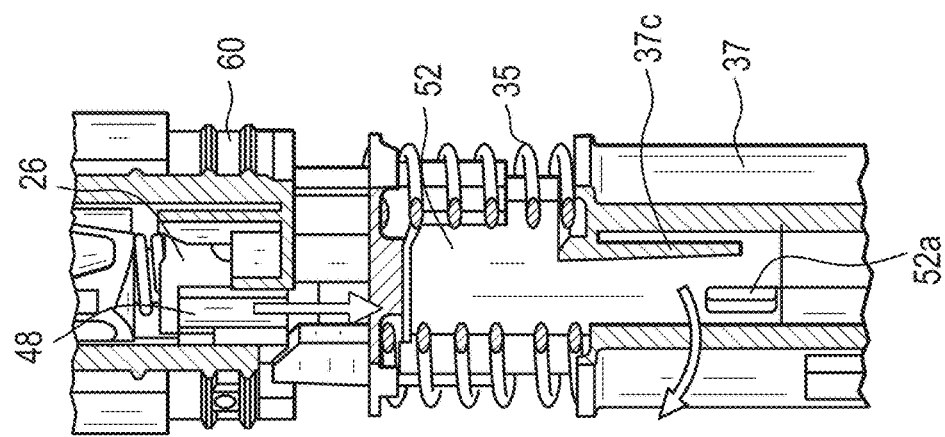
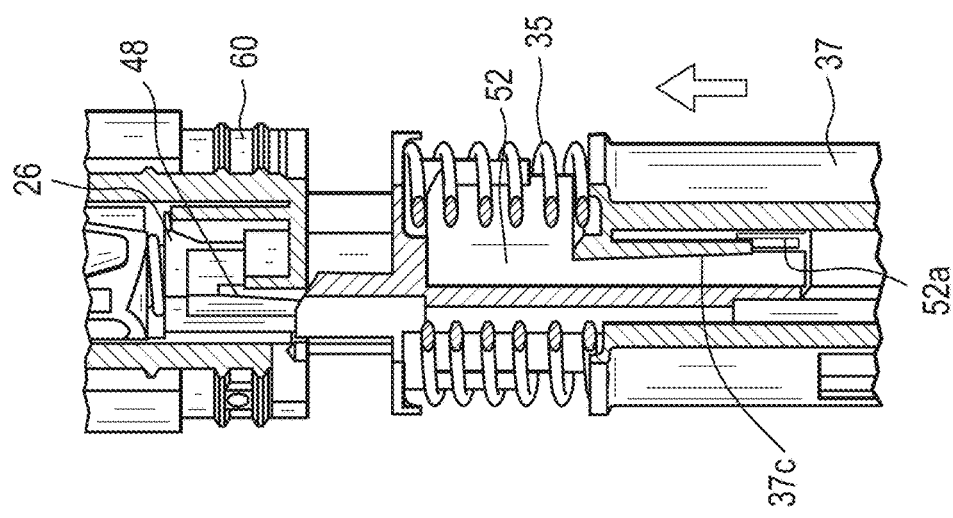
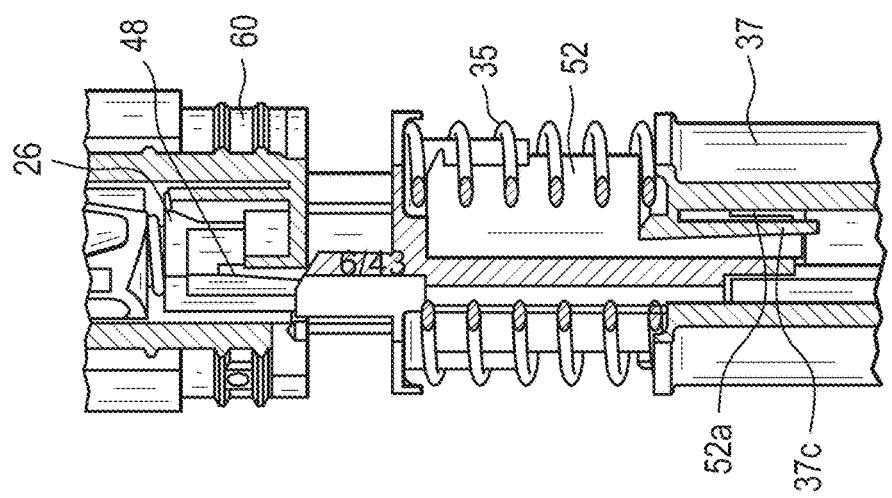

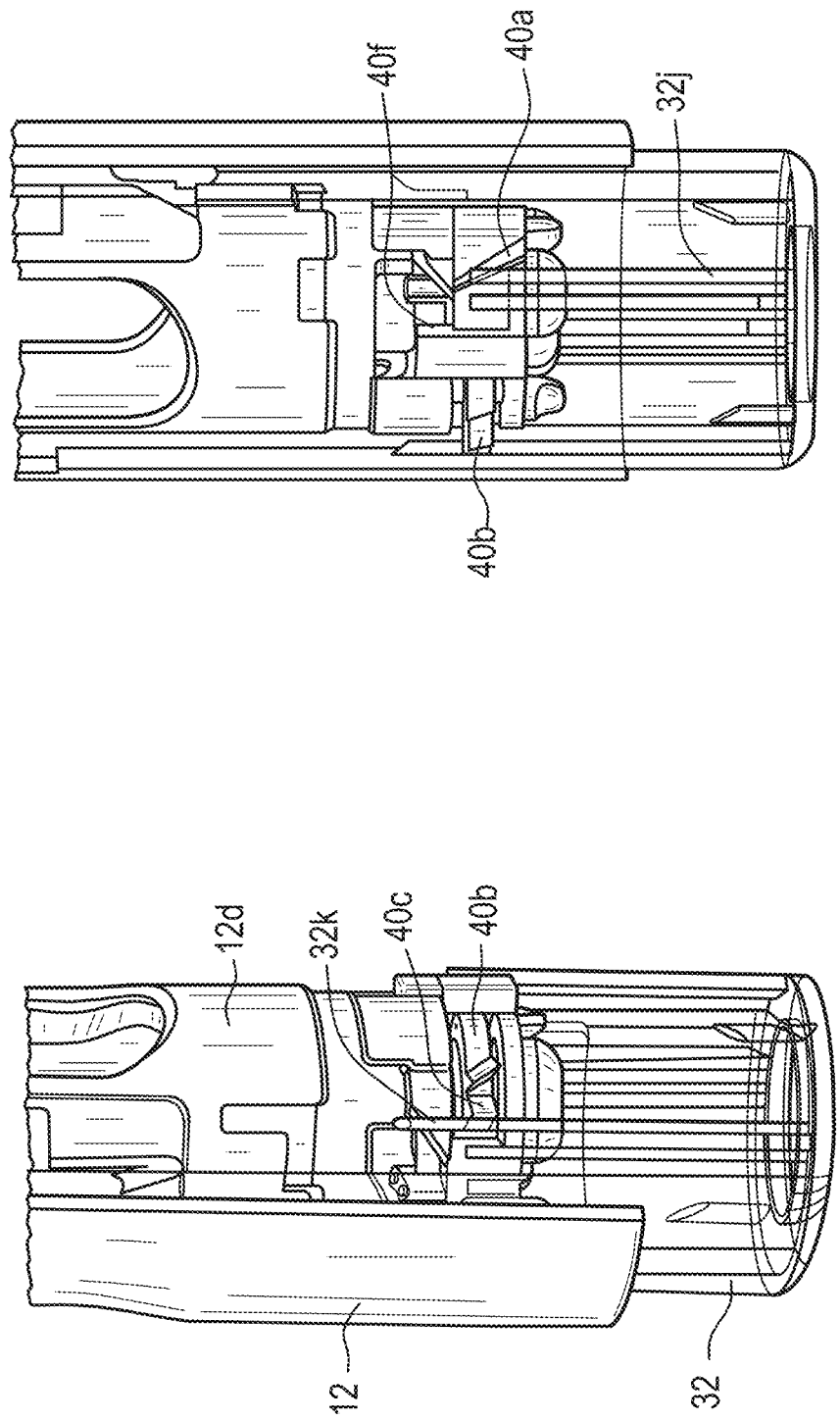

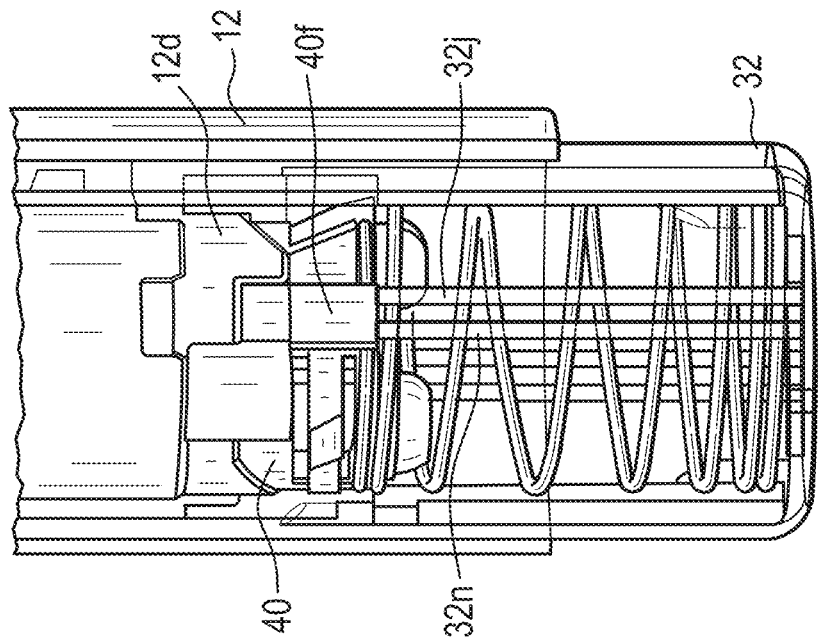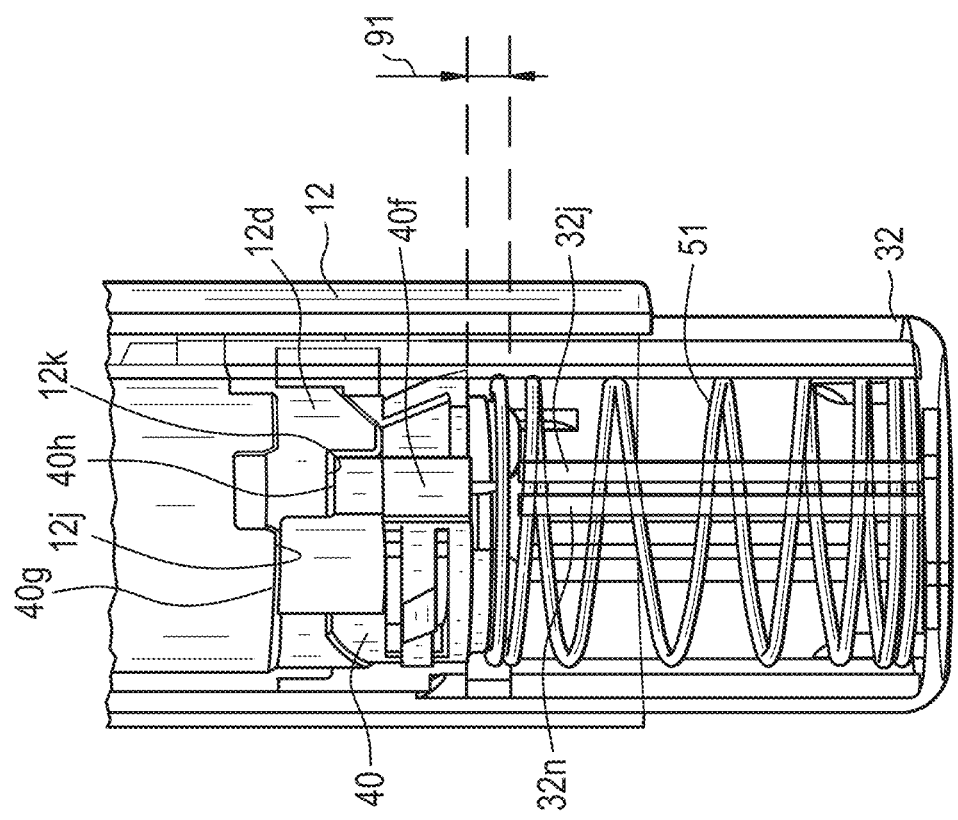

DRUG DELIVERY DEVICE

CROSS-REFERENCES TO RELATED APPLICATIONS

The present application is a continuation of U.S. Non-Provisional patent application Ser. No. 17/036,129, filed Sep. 29, 2020, entitled, "Drug Delivery Device," which claims the priority of U.S. Provisional Application No. 62/908,504, filed Sep. 30, 2019, entitled, "Drug Delivery Device," and U.S. Provisional Application No. 62/961,031, filed Jan. 14, 2020, entitled, "Drug Delivery Device," each of which is incorporated by reference herein in its entirety.

FIELD OF DISCLOSURE

The present disclosure relates to drug delivery devices, and, more particularly, devices for automatically injecting a drug into a patient.

BACKGROUND

A general aversion to exposed needles, as well as health and safety issues, have led to the development of drug delivery devices which conceal a needle or other insertion member prior to use and which automate various aspects of an injection process. Such devices offer a variety of benefits as compared with traditional forms of drug delivery including, for example, delivery via a conventional syringe.

Many injector systems use coil and other spring structures to provide actuation energy for functions such as needle insertion and/or fluid delivery. The use of springs can offer benefits of simplicity and low cost, but it may have certain limitations. For example, there is a linear relationship between force and displacement in spring actuators. To provide sufficient energy for drug delivery at the end of plunger stroke, an excessive amount of energy may be input to the system as drug delivery commences. As another example, as higher viscosity drugs are delivered via auto-injectors, the requisite spring forces will likely increase. Springs with higher spring constants may transmit more force to the drug product and primary container. Various physical characteristics of a spring may affect the spring rate, and thus the spring force, such as wire diameter of the spring, mean diameter of the spring, the number of spring coils, and the spring material. Therefore, it may be desirable and/or advantageous to include device components that permit flexibility in spring design and/or that facilitate the use of springs with different physical characteristics with the remaining device components.

The present disclosure sets forth drug delivery devices embodying advantageous alternatives to existing drug delivery devices, and that may address one or more of the challenges or needs mentioned herein.

SUMMARY

One aspect of the present disclosure provides a drug delivery device including a housing defining a longitudinal axis and having an opening and a drug storage container including a delivery member having an insertion end configured to extend at least partially through the opening during a delivery state. The device may further include a plunger moveable toward the distal end of the drug storage container to expel a drug from the drug storage container through the delivery member, the plunger including a body portion having an inner wall defining an axial chamber and an outer wall cooperating with the inner wall to define a body thickness. The device may also include a plunger biasing member disposed at least partially within the axial chamber, the plunger biasing member configured to urge the plunger toward the distal end of the drug storage container.

The plunger body portion may have a hollow tubular shape. The plunger body portion may be made of metal or non-metal.

The plunger may be configured to selectively rotate from an initial rotational position to a second rotational position under a biasing force exerted by the plunger biasing member and to translate linearly toward the distal end of the drug storage container under the biasing force exerted by the plunger biasing member after rotating from the initial rotational position to the second rotational position.

The device may further include a plunger guide fixed relative to the housing, the plunger being disposed at least partially within the plunger guide. One of the plunger and the plunger guide may comprises a cam and the other one of the plunger and the plunger guide may comprises a cam follower.

The plunger may include the cam follower and the plunger guide includes the cam, and the cam follower may be formed by at least one flange extending radially outwardly from the plunger.

The plunger body thickness may be less than 0.6 millimeters, less than 0.4 millimeters, less than 0.3 millimeters, less than 0.2 millimeters, less than 0.1 millimeters, or less than 0.05 millimeters.

Another aspect of the present disclosure provides a drug delivery device including a housing defining a longitudinal axis and having an opening and a drug storage container including a delivery member having an insertion end configured to extend at least partially through the opening during a delivery state. The device may further include a plunger moveable toward the distal end of the drug storage container to expel a drug from the drug storage container through the delivery member, the plunger including a body portion having an inner wall defining an axial chamber and an outer wall cooperating with the inner wall to define a body thickness less than 0.6 millimeters. The device may also include a plunger biasing member coupled with the plunger and configured to urge the plunger toward the distal end of the drug storage container.

BRIEF DESCRIPTION OF THE DRAWINGS

It is believed that the disclosure will be more fully understood from the following description taken in conjunction with the accompanying drawings. Some of the drawings may have been simplified by the omission of selected elements for the purpose of more clearly showing other elements. Such omissions of elements in some drawings are not necessarily indicative of the presence or absence of particular elements in any of the exemplary embodiments, except as may be explicitly delineated in the corresponding written description. Also, none of the drawings is necessarily to scale.

FIG. 3A is an exploded assembly view of a portion, namely the drive mechanism, of the drug delivery device in FIG. 2;

FIG. 4D is a perspective view of an exemplary container holder for use with a drug delivery device in accordance with various embodiments, where the container holder is in a closed position;

FIG. 4E is a perspective view of an exemplary housing for use with a drug delivery device in accordance with various embodiments;

FIG. 11A is a perspective view of the components in FIG. 9A plus additional components, such as an exemplary guard extension, and wherein the drug delivery device is in a pre-injection position;

FIG. 11B is a perspective view of the components in FIG. 11A, wherein the guard extension has been moved proximally but the plunger has not been released;

FIG. 11C is a perspective view of the components in FIG. 11A, wherein the guard extension has been further moved proximally and the plunger has released but has not yet traveled axially;

FIG. 15A is a perspective view of the distal portion of the device shown in FIG. 14, where the guard member is in an initial deflection stage;

FIG. 15B is a perspective view of the same device and the same stage as FIG. 15A, from a view that is approximately 90 degrees from that shown in FIG. 15A;

FIG. 18A is a perspective view of the distal portion of the device shown in FIG. 14, where the guard member is in a fully-retracted, locked-out position with respect to the housing, and the device is in a post-injection stage;

FIG. 18B is a perspective view of the distal portion of the device shown in FIG. 14, where the guard member is in a near fully-retracted, locked-out position with respect to the housing, and the device is in a post-injection stage;

DETAILED DESCRIPTION

The present disclosure generally relates to drug delivery devices operable by a user for administering a drug, or in the case where a patient is the user, self-administering a drug. Various features are disclosed for streamlining, simplifying, automating and/or facilitating certain aspects of drug delivery, such as those utilized in auto-injectors, on-body injectors, or other automatic or partially automatic drug delivery devices (collectively autoinjectors or auto-injectors). For example, these features may include automatically covering a needle in a pre-delivery and/or post-delivery state, automatically inserting a needle and/or a cannula into a user, automatically activating a drive mechanism, automatically indicating to the user that drug delivery is complete, among other features. Although known drug delivery devices incorporate a separate or independently operable mechanism to realize each of its automated features, the present disclosure includes eliminating and/or combining at least some of these features and/or providing device components that permit flexibility in device design. For example, the device may include components that permit flexibility in spring design and/or that facilitate the use of springs with different physical characteristics with the remaining device components. As another example, the device may include components that reduce the part number, part complexity, overall weight of the device, and/or overall complexity of the device. For example, the present disclosure may include a plunger moveable toward the distal end of the drug storage container to expel a drug from the drug storage container through the delivery member, where the plunger includes a body portion having an inner wall defining an axial chamber and an outer wall cooperating with the inner wall to define a body thickness. The present disclosure may also include a plunger biasing member disposed at least partially within the axial chamber, where the plunger biasing member is configured to urge the plunger toward the distal end of the drug storage container.

Figures 1A, 1B:
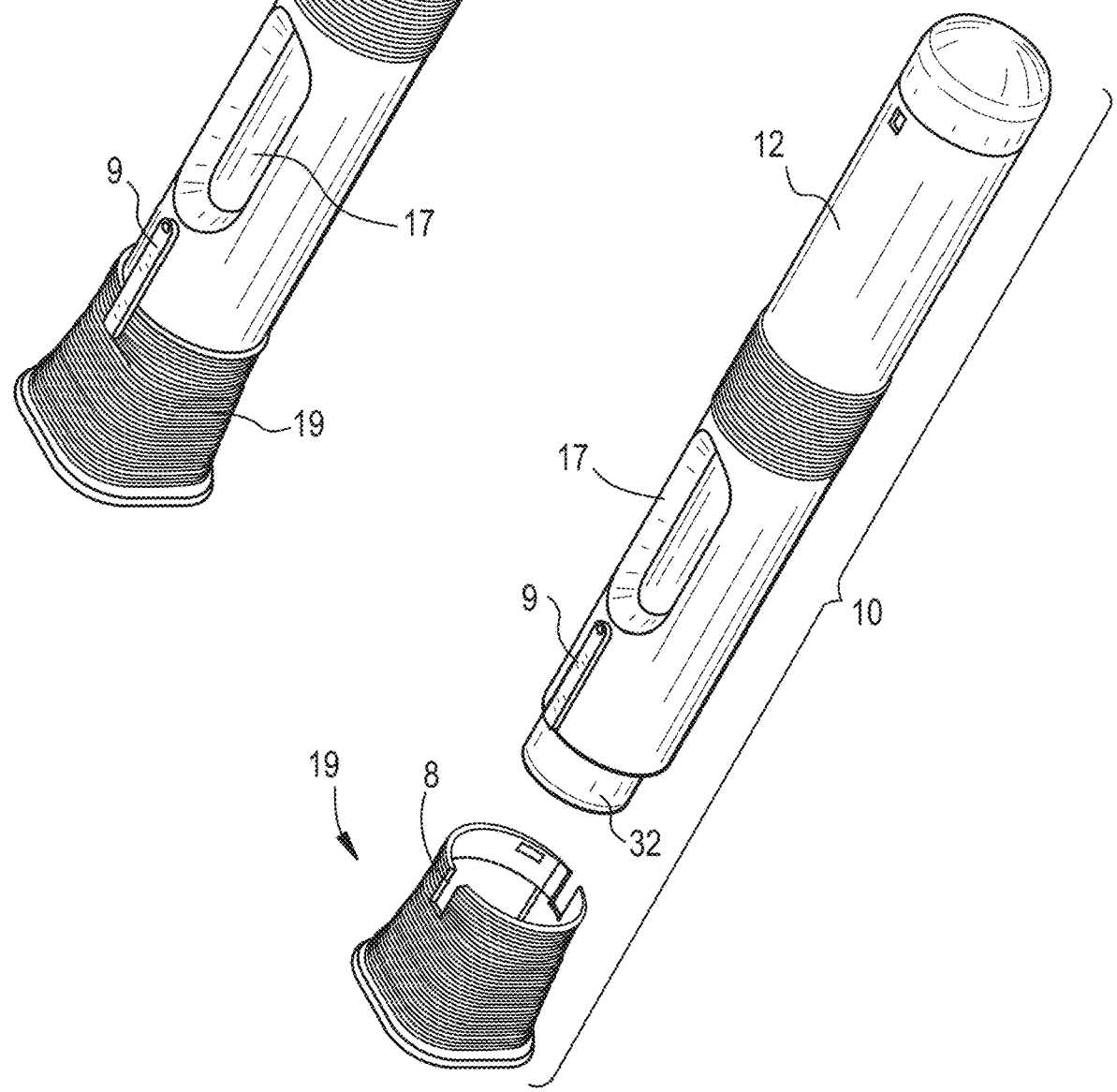
FIG. 1A is a perspective view of an exemplary drug delivery device in accordance with various embodiments.
FIG. 1B is a perspective view of the drug delivery device in FIG. 1A, with a cap removed therefrom.
Figure 1C:
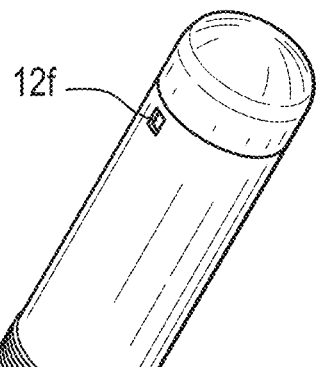
FIG. 1C is a perspective view of the drug delivery device in FIG. 1A, in a pre-injection configuration.
Figure 1D:
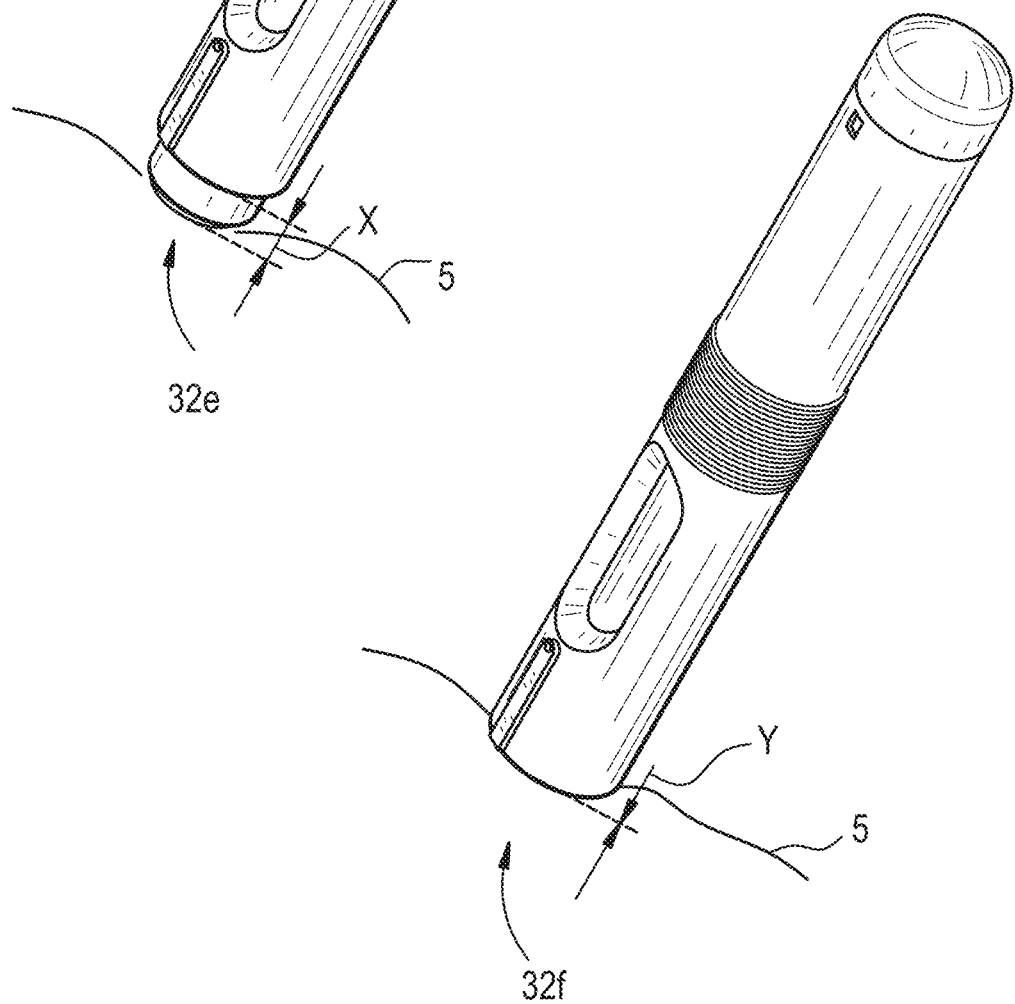
FIG. 1D is a perspective view of the drug delivery device in FIG. 1A, in an injection configuration.
Figure 2:
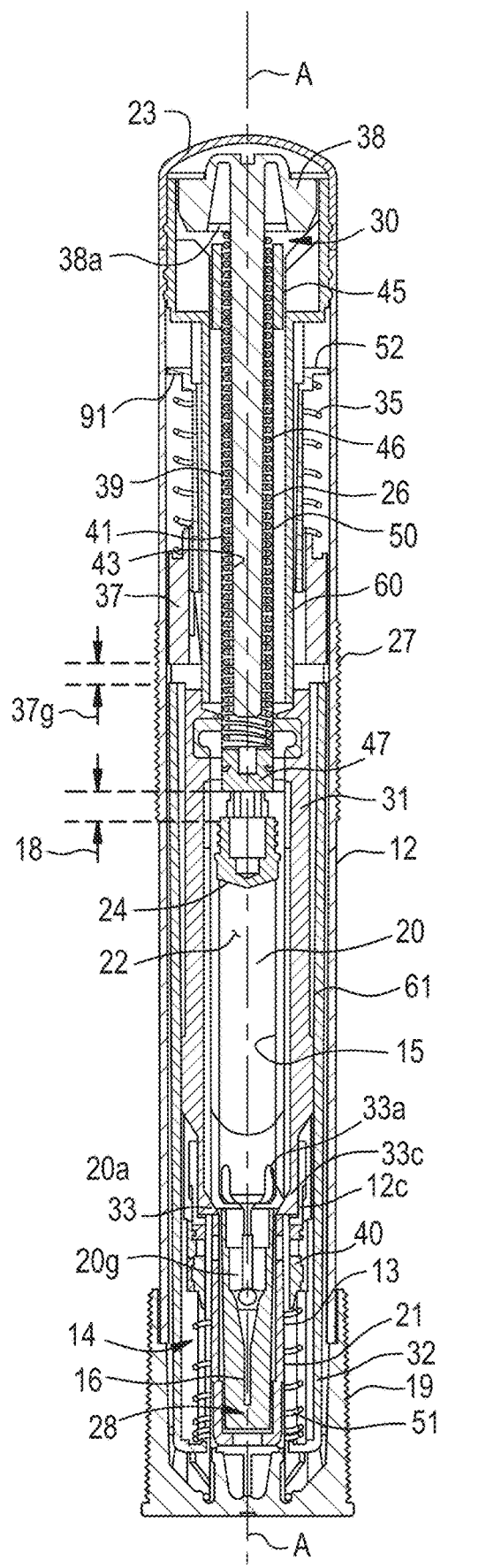
FIG. 2 is cross-sectional view of the drug delivery device in FIG. 1.

FIGS. 1-3 illustrate several views of an embodiment of a drug delivery device 10 for delivering a drug, which may also be referred to herein as a medicament or drug product. The drug may be, but is not limited to, various biologicals such as peptides, peptibodies, or antibodies. The drug may be in a fluid or liquid form, although the disclosure is not limited to a particular state.

Various implementations and configurations of the drug delivery device 10 are possible. The present embodiment of the drug delivery device 10 is configured as a single-use, disposable injector. In other embodiments, the drug delivery device 10 may be configured as multiple-use reusable injector. The drug delivery device 10 is operable for self-administration by a patient or for administration by caregiver or a formally trained healthcare provider (e.g., a doctor or nurse). The exemplary the drug delivery devices shown in the figures may take the form of an autoinjector or pen-type injector, and, as such, may be held in the hand of the user over the duration of drug delivery, but may also or alternatively be suitable for other drug delivery devices and/or configurations.

The configuration of various components included in the drug delivery device 10 may depend on the operational state of the drug delivery device 10. The drug delivery device 10 may have a pre-delivery or storage state, a delivery or dosing state, and a post-delivery state, although fewer or more states are also possible. For example, each state may have several sub-states or stages. The pre-delivery state may correspond to the configuration of the drug delivery device 10 subsequent to assembly and prior to activation by the user. In some embodiments, the pre-delivery state may exist in the time between when the drug delivery device 10 leaves a manufacturing facility and when a patient or user activates a drive mechanism 30 of the drug delivery device 10. This includes the moments in time after the user has removed the drug delivery device 10 from any secondary packaging and prior to positioning the drug delivery device 10 against the injection site. The delivery state may correspond to the configuration of the drug delivery device 10 while drug delivery, also referred to herein as dosing, is in progress. The post-delivery state may correspond to the configuration of the drug delivery device 10 after drug delivery is complete and/or when a stopper is arranged in an end-of-dose position in a drug storage container.

As shown in FIGS. 1A and 1B, the drug delivery device 10 includes an outer casing or housing 12. In some embodiments, the housing 12 may be sized and dimensioned to enable a person to grasp the injector 10 in a single hand. The housing 12 may have a generally elongate shape, such as a cylindrical shape, and extend along a longitudinal axis A between a proximal end and a distal end. An opening 14 (FIG. 3B) may be formed in the distal end to permit an insertion end 28 of a delivery member 16 (FIG. 2) to extend outside of the housing 12. A transparent or semi-transparent inspection window 17 (FIGS. 1A-1B) may be positioned in a wall of the housing 12 to permit a user to view component(s) inside the drug delivery device 10, including a drug storage container 20. Viewing the drug storage container 20 through the window 17 may allow a user to confirm that drug delivery is in progress and/or complete. A removable cap 19 may cover the opening 14 prior to use of the drug delivery device 10, and, in some embodiments, may including a gripper 13 (FIG. 2) configured to assist with removing a sterile barrier 21 (e.g., a rigid needle shield (RNS), a non-rigid needle shield (nRNS), etc.) mounted on the insertion end 28 of the delivery member 16. The gripper 13 may include one or more inwardly protruding barbs or arms that frictionally or otherwise mechanically engage the sterile barrier 21 to pull the sterile barrier 21 with the removable cap 19 when the user separates the removable cap 19 from the housing 12. Thus, removing the removable cap 19 has the effect of removing the sterile barrier 21 from the delivery member 16.

As shown in FIG. 2, the drive mechanism 30 may be disposed partially or entirely within the housing 12. Generally, the drive mechanism 30 may be configured to store energy and, upon or in response to activation of the drive mechanism 30 by the user, release or output that energy to drive the plunger 26 to expel the drug 22 from the drug storage container 20 through the delivery member 16 into the patient. In the present embodiment, the drive mechanism 30 is configured to store mechanical potential energy; however, alternative embodiments of the drive mechanism 30 may be configured differently, for example, with the drive mechanism 30 storing electrical or chemical potential energy. Generally, upon activation of the drive mechanism 30, the drive mechanism 30 may convert the potential energy into kinetic energy for moving the plunger 26. As best illustrated in FIG. 3A, in one embodiment, the drive mechanism 30 includes the plunger biasing member 50, a hollow rod 46 for supporting the plunger biasing member 50, a plunger biasing member seat 38, the releaser member 52, a plunger guide 60, an extender biasing member 35, and a guard extension 37. The plunger biasing member 50 may include a compression spring (e.g., a helical compression spring) which is initially retained in an energized state. In the energized state, the plunger biasing member 50 may be compressed such that its axial length is shorter than it would be in a natural or de-energized state. When released, the plunger biasing member 50 may try to expand to its natural axial length, and as a consequence, exert a biasing force pushing the plunger 26 in the distal direction.

Figure 3B:
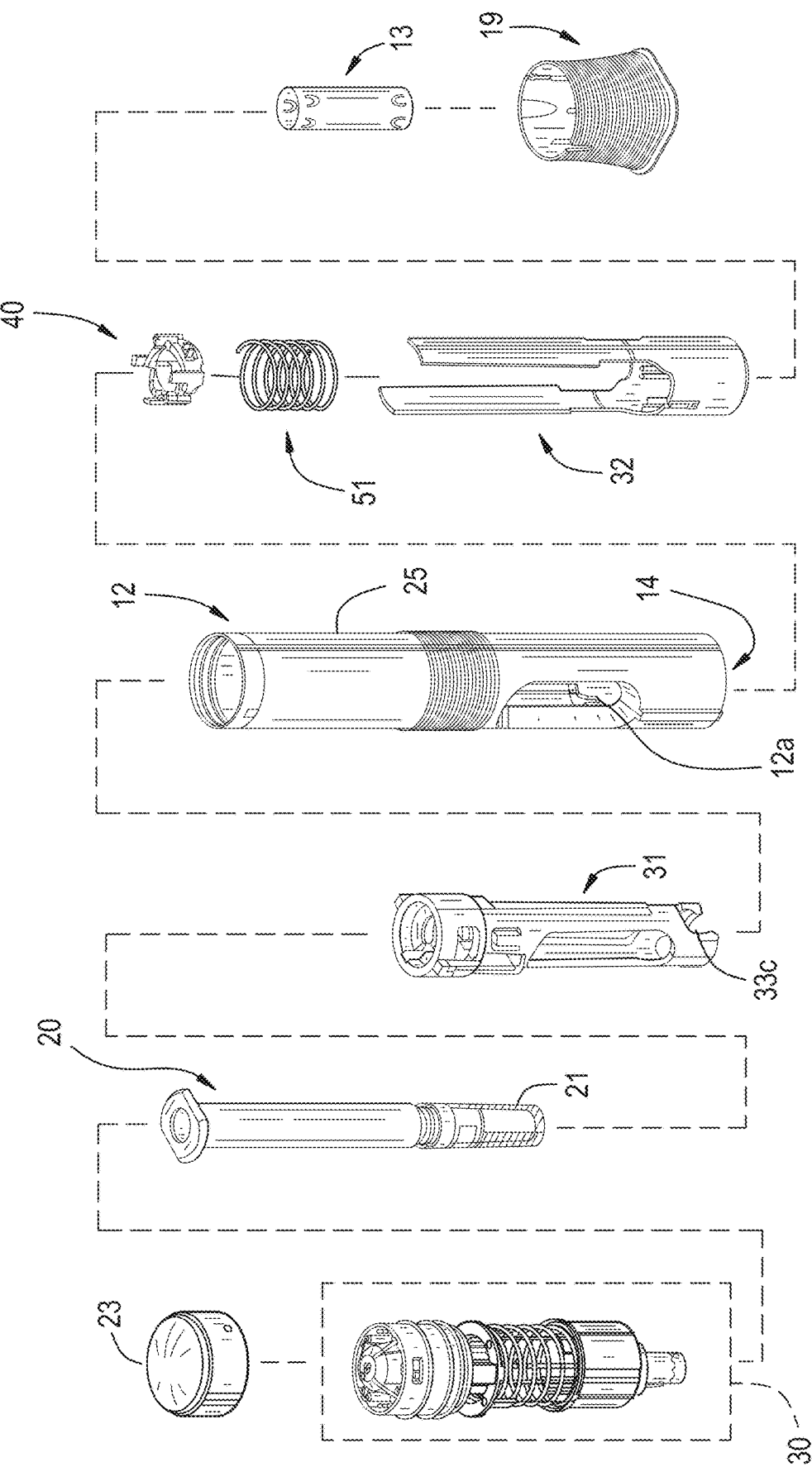
FIG. 3B is an exploded assembly view of the drug delivery device in FIG. 2.

As best shown in FIGS. 2 and 3B, in one embodiment the device 10 include a housing 12 may include two separate and interconnected structures: a rear end cap 23 (e.g., a rear cover) at the proximal end of the drug delivery device 10; and a tubular housing 25 extending substantially completely along the length of the drug delivery device 10 and defining the opening 14. Additionally or alternatively, the housing 12 may include fewer or more components, such as a two-piece tubular housing having front and rear portions. The tubular housing 25 may have a hollow and generally cylindrical or tubular shape, and the rear end cap 23 may have a generally hemispherical shape or a hollow cylindrical shape with an open end and a closed off end. In some embodiments, the rear end cap 23 and the tubular housing 25, and any components to be positioned therein, may be assembled together to define different sub-assemblies, such as the drive mechanism 30 (FIG. 3A). In some embodiments, the different sub-assemblies are assembled independently of each other and then later combined with one another, as well as with the drug storage container 20, to form the fully-assembled drug delivery device 10. In certain such embodiments, some or all of the foregoing phases of assembly may occur in different manufacturing facilities or environments. In alternative embodiments, the housing 12 may be constructed in one piece, such that the housing 12 is defined by a single, monolithic structure that integrates a rear cap and tubular housing in a single component.

The drug storage container 20 is disposed within an interior space of the housing 12 and is configured to contain a drug 22. The drug storage container 20 may be pre-filled and shipped, e.g., by a manufacturer, to a location where the drug storage container 20 is combined with a remainder of the drug delivery device 10. For example, the drug 22 may be distributed and/or provided to patients in more than one use case, such as a as a pre-filled syringe or as an autoinjector including a pre-filled syringe. By utilizing the same or similar syringe components in either case, at least some of above steps such as filling, labeling, packaging, shipping, and distribution may be streamlined or simplified for two different use cases. As a another example, in the event that multiple use cases utilize some or all of the same syringe components, some regulatory pathways to marketing and/or distributing the drug may be streamlined and/or simplified for at least one of the multiple use cases.

The housing 12 may be pre-loaded with the drug storage container 20, e.g., by a manufacturer, or alternatively, loaded with the drug storage container 20 by a user prior to use of the drug delivery device 10. The drug storage container 20 may include a rigid wall defining an internal bore or reservoir. The wall may be made of glass or plastic. A stopper 24 may be moveably disposed in the drug storage container 20 such that it can move in a distal direction along the longitudinal axis A between proximal end and a distal end of the drug storage container 20. The stopper 24 may be constructed of rubber or any other suitable material. The stopper 24 may slidably and sealingly contact an interior surface 15 of the wall of the drug storage container 20 such that the drug 22 is prevented or inhibited from leaking past the stopper 24 when the stopper 24 is in motion. Distal movement of the stopper 24 expels the drug 22 from the reservoir of the drug storage container 20 into the delivery member 16. The proximal end of the drug storage container 20 may be open to allow a plunger 26 to extend into the drug storage container 20 and push the stopper 24 in the distal direction. In the present embodiment, the plunger 26 and the stopper 24 are initially spaced from each other by a gap 18 (FIG. 2). Upon activation of a drive mechanism 30, the plunger 26 moves in the distal direction to close the gap and comes into contact with the stopper 24. Subsequent distal movement of the plunger 26 drives the stopper 24 in the distal direction to expel the drug 22 from the drug storage container 20. In alternative embodiments, the stopper 24 and the plunger 26 may initially be in contact with one another or coupled to one another, e.g., via a threaded coupling, such that they move together jointly from the start of movement of the plunger 26. Once the stopper 24 is in motion, it may continue to move in the distal direction until it contacts a proximally-facing portion of the interior surface 15 of the wall of the drug storage container 20. This position of the stopper 24 may be referred to as the end-of-dose or end-of-delivery position, and may correspond to when delivery of the drug 22 to the patient is complete or substantially complete.

In some embodiments, a volume of the drug 22 included in the reservoir of the drug storage container 20 may be equal to 1 mL, or equal to approximately (e.g., ±10%) 1 mL, or equal to 2.5 mL, or equal to approximately (e.g., ±10%) 2.5 mL, or equal to 3 mL, or equal to approximately (e.g., ±10%) 3 mL, or less than or equal to approximately (e.g., ±10%) 1 mL, or less than or equal to approximately (e.g., ±10%) 2 mL, or less than or equal to approximately (e.g., ±10%) 3 mL, or less than or equal to approximately (e.g., ±10%) 4 mL, or less than approximately (e.g., ±10%) 5 mL, or less than or equal to approximately (e.g., ±10%) 10 mL, or within a range between approximately (e.g., ±10%) 1-10 mL, or within a range between approximately (e.g., ±10%) 1-5 mL, or within a range between approximately (e.g., ±10%) 1-4 mL, or within a range between approximately (e.g., ±10%) 1-3 mL, or within a range between approximately (e.g., ±10%) 1-2.5 mL.

The delivery member 16 is connected or operable to be connected in fluid communication with the reservoir of the drug storage container 20. A distal end of the delivery member 16 may define the insertion end 28 of the delivery member 16. The insertion end 28 may include a sharpened tip of other pointed geometry allowing the insertion end 28 to pierce the patient's skin 5 and subcutaneous tissue during insertion of the delivery member 16. The delivery member 16 may be hollow and have an interior passageway. One or more openings may be formed in the insertion end 28 to allow drug to flow out of the delivery member 16 into the patient.

In one embodiment, the drug storage container 20 may be a pre-filled syringe and has a staked, hollow metal needle for the delivery member 16. Here, the needle is fixed relative to the wall of the drug storage container 20 and may be in permanent fluid communication with the reservoir of the drug storage container 20. In other embodiments, the needle may be coupled to the drug storage container 20 via a Luer Lock or other suitable connection. In yet other embodiments, the drug storage container 20 may be a needle-less cartridge, and, as such, initially may not be in fluid communication with the delivery member 16. In such embodiments, the drug storage container 20 may move toward a proximal end of the delivery member 16, or vice versa, during operation of the drug delivery device 10 such that the proximal end of the delivery member 16 penetrates through a septum covering an opening in the drug storage container 20 thereby establishing fluid communication between the reservoir of the drug storage container 20 and the delivery member 16.

The drug storage container 20 may include a body portion 20g with a distal end 20e and a proximal end 20f. The drug storage container 20 may be fixed relative to the housing 12 such that the drug storage container 20 does not move relative to the housing 12 once installed in the housing 12. As such, the insertion end 28 of the delivery member 16 extends permanently through the opening 14 in the housing 12 in the pre-delivery, delivery, and post-delivery states. For example, as shown in FIG. 2, the delivery member 16 extends beyond a distal end of the housing 12 that defines the opening 14. However, in some configurations, such as the storage configuration shown in FIG. 2, the delivery member 16 is covered/protected by the sterile barrier 21 and a guard member 32 that surrounds the delivery member 16 and protects against or reduces the likelihood of unintended or premature needle stick.

The container holder 31 may have a hollow and generally cylindrical or tubular shape centered about the longitudinal axis A, and the drug storage container 20 may be disposed partially or entirely within the container holder 31. A distal end of the container holder 31 may include an inwardly protruding flange 33 abutting against a shoulder portion 20a of the drug storage container 20, thereby preventing distal movement of the drug storage container 20 during actuation of the plunger 26.

In one embodiment, a container holder 31 secures and/or fixes the position of the drug storage container 20 within the housing 12. For example, the container holder 31 may be configured to support the drug storage container 20 with respect to the housing 12 proximal to at least a portion of the distal end of the body portion of the drug storage container 20 (including, for example, proximal to an entirety of the distal end of the body portion of the drug storage container 20) such that a resultant force acting on the drug storage container 20 from the plunger biasing member 50 is at least substantially completely borne by the distal end of the body portion of the drug storage container 20.

Figure 4A:
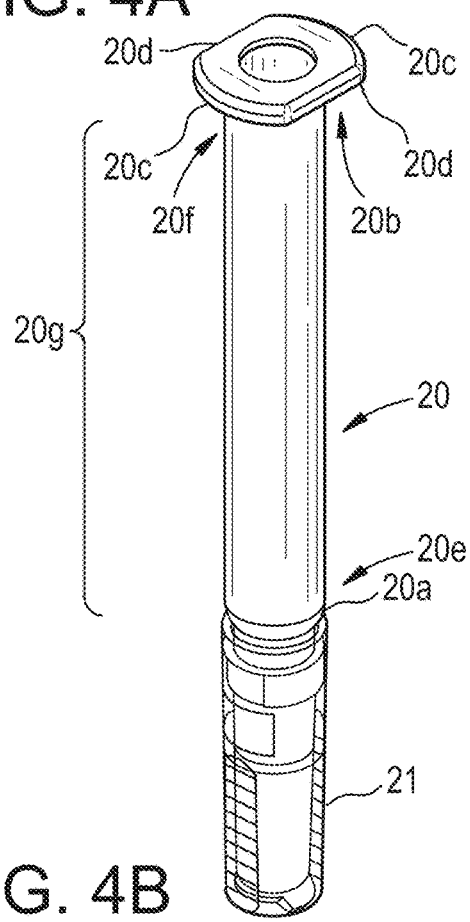
FIG. 4A is a perspective view of an exemplary drug storage container for use with a drug delivery device in accordance with various embodiments.

The term "body portion" of the drug storage container 20 as used herein is the generally cylindrical portion of the drug storage container 20. For example, the body portion 20g of the drug storage container 20 shown in FIG. 4A extends from the distal side of the flange 20c to the proximal side of the shoulder portion 20a. As a more specific example, the body portion 20g of the drug storage container 20 shown in FIG. 4A has a relatively constant inner diameter and/or a relatively constant outer diameter along its length. As shown in FIGS. 4A and 2, proximal to the distal end 20e of the body portion 20g, the drug storage container 20 defines the shoulder portion 20a. The delivery member 16 extends distally from the distal end 20e of the body portion 20g of the drug storage container 20. As a more specific example, the drug storage container 20 further includes a neck portion 20g positioned distally of the shoulder portion 20a and configured to support the delivery member 16 such as a staked needle.

The term "resultant force" refers to force the urging the drug storage container 20 along the axis A upon and due to actuation of the plunger biasing member 50 during and after the injection state. For example, when the plunger 26 is actuated and driven in the distal direction along axis A, it urges the stopper 24 in the distal direction. As a result of this direct contact between the plunger 26 and the stopper 24, as well as frictional forces between the stopper 24 and the drug storage container 20 and the forces required to urge the drug 22 through the relatively small-diameter delivery member 16, the drug storage container 20 is urged in a distal direction even though the plunger 26 may not directly touch, abut, or engage the body portion of the drug storage container 20. As a result, the drug storage container 20 may experience a relatively high resultant force during the injection process, more specifically during the actuation of the plunger 26.

The force concentration of the resultant force acting on the drug storage container 20 during the plunger actuation is highest in the portion of the drug storage container 20 that is resisting distal movement. For example, in the device shown in the figures, the force concentration is highest proximal to at least a portion of the distal end 20e of the body portion 20g of the drug storage container 20. As a more specific example, the force concentration is highest at the shoulder portion 20a where the drug storage container 20 is supported by the container holder 31. As an even more specific example, the force concentration is at least substantially completely borne by the shoulder portion 20a of drug storage container 20. The term "substantially completely" may mean greater than 50%, it may mean greater than 70%, it may mean greater than 75%, it may mean greater than 80%, it may mean greater than 80%, it may mean greater than 85%, it may mean greater than 90%, it may mean greater than 95%, it may mean greater than 98%, or any other suitable number.

The force concentration of the resultant force acting on the drug storage container 20 during the plunger actuation is preferably not significantly borne by the outwardly protruding flange 20d of the drug storage container 20. For example, because the force is substantially completely borne by the distal portion 20e of the body portion 20g of the drug storage container 20, the force concentration in and near the outwardly protruding flange 20d is relatively low. As a more specific example, the percentage of the resultant force acting on the entire drug storage container 20 that is borne by the outwardly protruding flange 20d may be less than 20%, or it may be less than 15%, or it may be less than 10%, or it may be less than 5%, or it may be less than 3%, or it may be less than 2%, or it may be less than 1%, or it may be about 0%.

Figure 4B:
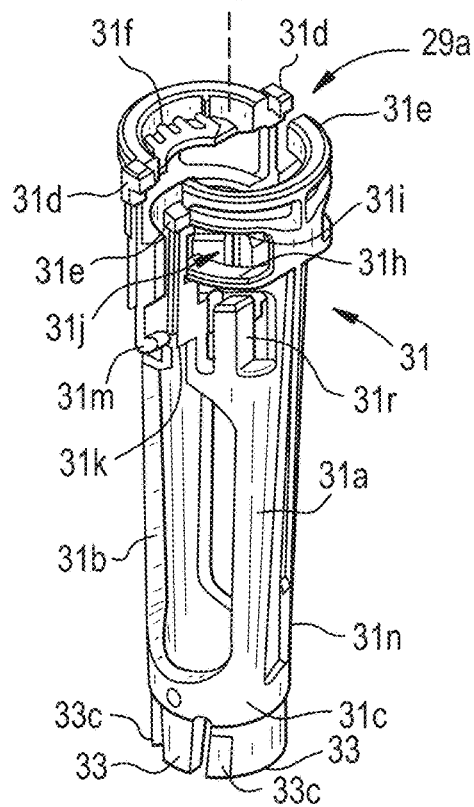
FIG. 4B is a perspective view of an exemplary container holder for use with a drug delivery device in accordance with various embodiments, where the container holder is in an open position.

As shown in FIGS. 2 and 4B, the container holder 31 includes a plurality flanges 33 that each include an arcuate, sloped surface 33a that substantially matches the arcuate shape of the shoulder portion 20a of the drug storage container 20. As a more specific example, when the drug storage container 20 is inserted within the container holder 31, the flanges 33 cooperate to support the shoulder portion 20a and limit the travel of the drug storage container 20 in the distal direction. The flanges 33 are separated from each other by a gap 33b (FIG. 3b) to permit flex of the flanges 33, as will be discussed below in more detail. The container holder 31 shown in FIGS. 4A-4C includes four flanges 33, but any suitable number of flanges may be utilized, as will be discussed below with respect to another exemplary design shown in FIG. 4D.

The container holder 31 may have an open position 29a (FIG. 4B) where it is able to receive the drug storage container 20 during assembly and a closed position 29b (FIG. 4C) where it is able to support or at least partially support the drug storage container 20. As a more specific example, the container holder 31 includes a pair of arms 31a, 31b extending axially from an annular ring 31c such that the arms 31a, 31b can flex away from or towards each other to move between the open position 29a and the closed position 29b. The annular ring 31c in the figures is positioned near the distal end of the container holder 31 so that the proximal portions of the arms 31a, 31b are able to extend away from each other when the container holder 31 is in the open position 29a. The container holder 31 further includes mating connectors 31d, 31e adjacent the top (proximal) portion of the container holder 31 that are configured to snap-fit with each other when the container holder is in the closed position 29b. As a more specific example, when the mating connectors 31d, 31e are engaged with each other, a frictional fit between the respective components holds the container holder 31 in the closed position 29b.

The container holder 31 shown in the figures also includes a pair of inwardly-protruding flanges 31f, 31g positioned adjacent to the proximal end of the container holder 31. When the container holder 31 is in the open position 29a, the inwardly-protruding flanges 31f, 31g are spaced apart from each other such that a radially outwardly-protruding flange 20b on the drug storage container 20 is able to be placed into the container holder 31 (via insertion in the distal direction). In other words, when the container holder 31 is in the open position 29a the outwardly-protruding flange 20b on the drug storage container 20 is able to clear the gap between the inwardly-protruding flanges 31f, 31g. Once the drug storage container 20 is fully inserted within the container holder 31 (e.g., such that the shoulder portion 20a of the drug storage container 20 contacts the inwardly-protruding flanges 33) the container holder arms 31a, 31b are able to be moved into the closed position 29b, in which the inwardly-protruding flanges 31f, 31g prevent the drug storage container 20 from exiting the container holder 31 in the proximal direction. In other words, once the drug storage container 20 is inserted into the container holder 31 and the drug storage container 20 is in the closed position 29b, the drug storage container 20 is held within the container holder 31 by the inwardly protruding flanges 33 near the distal end of the container holder 31 and by the inwardly-protruding flanges 31f, 31g near the proximal end of the container holder 31.

Figure 4C:
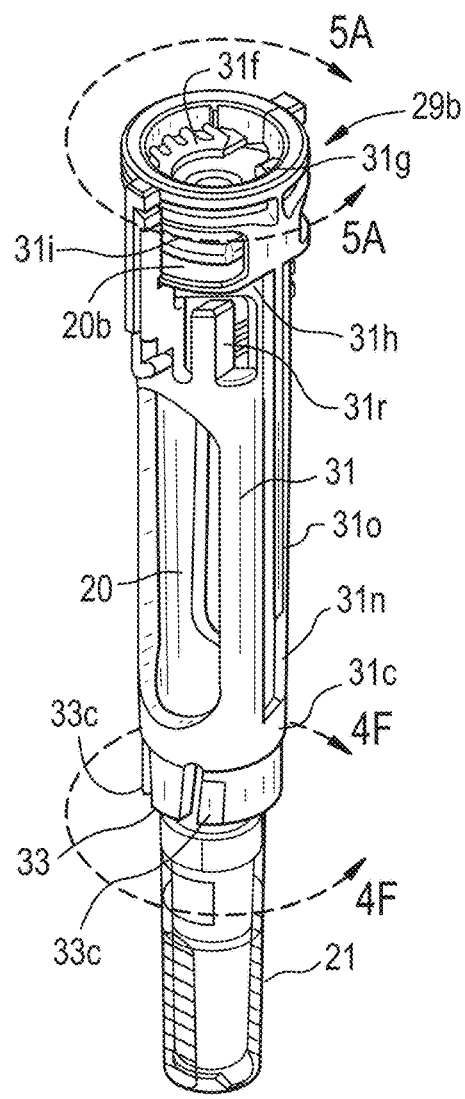
FIG. 4C is a perspective view of the container holder in FIG. 4B coupled with the drug storage container in FIG. 4A, where the container holder is in a closed position.

As shown in FIGS. 4B and 4C, the container holder 31 includes opposing surfaces 31i, 31h defining an opening 31j for receiving the flange 20b of the drug storage container 20. For example, the container holder 31 shown in the figures includes two distally-facing surfaces 31i and two proximally-facing surfaces 31h that respectively cooperate to define two openings 31j that each receive opposing portions of the flange 20b. The opposing surfaces 31h, 31i define the lower and upper boundaries for positioning of the flange 20b when the drug storage container 20 is positioned within the container holder 31 in the closed position 29b. This range from lower and upper boundaries may provide flexibility for drug storage containers 20 of varying lengths and/or for a range of tolerances for the length of the drug storage container 20. However, as discussed in more detail below, additional components of the device 10 may further secure the drug storage container 20 adjacent to the flange 20b when the drug storage container 20/container holder 31 assembly is inside of the housing 12. The openings 31j may also prevent and/or restrict rotational movement of the drug storage container 20. For example, opposing rounded sections 20c of the flange 20b may each extend at least partially through the openings 31j and opposing linear sections 20d of the flange 20b may each abut side walls defining the openings 31j to prevent and/or restrict rotational movement between the respective components 20, 31.

As shown in FIG. 4B, the container holder 31 may include additional mating connectors 31k, 31m, which are distally positioned from the mating connectors 31d, 31e. The respective pairs of mating connectors 31d, 31e; 31k, 31m may work together to create a snap fit between the respective arms 31a, 31b of the container holder 31 to secure the same in the closed position 29b.

It may be desirable for the annular ring 31c to be positioned generally opposite (along axis A) of the mating connectors 31d, 31e to facilitate opening and closing of the container holder arms 31a, 31b. For example, the distance between the annular ring 31c and the inwardly-protruding flanges 31f, 31g may be proportional to the clearance gap between the inwardly-protruding flanges 31f, 31g when the container holder 31 is in the open position 29a. Therefore, to maximize the gap between the inwardly-protruding flanges 31f, 31g when the container holder 31 is in the open position 29a, one can maximize the distance between the annular ring 31c and the inwardly-protruding flanges 31f, 31g (e.g., the effective length of the arms 31a, 31b). Additionally, the thickness, height, and material properties of the annular ring 31c may each affect the flex of the arms 31a, 31b and/or the gap between the inwardly-protruding flanges 31f, 31g when the container holder 31 is in the open position 29a. As discussed above, the gap 33b between the flanges may also facilitate and/or define the amount of flex of the arms 31a, 31b and/or the gap between the inwardly-protruding flanges 31f, 31g when the container holder 31 is moved into the open position 29a. For example, as the arms 31a, 31b flex outwardly, the flanges 33 may move inwardly.

The container holder 31 shown in the drawings may include an alignment ridge 31n that abuts an inner surface of the housing 12, to radially align the container holder 31 within the housing 12 during assembly and to prevent and/or restrict radial movement between the respective components 12, 31. As an example, the housing 12 may include a slot 12a formed on the inner surface of the housing to receive the alignment ridge 31n. The housing 12 may include multiple slots and the container holder 31 may include multiple alignment ridges to radially align the respective components 12, 31. For example, the container holder 31 shown in the figures includes two alignment ridges 31n and the housing 12 includes two slots 12a. The slots 12a are spaced apart from each other and sized such as to receive the respective alignment ridges 31*n* when the container holder 31 is inserted into the housing 12. The slots 12*a* shown in the figures are defined by a generally annular collar 12*d* portion that is integral with the housing 12 (although the collar portion may alternatively be one or more components coupled or fixed to the housing). The annular collar 12*d* may not extend around the entire inner surface of the housing 12 and instead has cut-outs or gaps to permit portions of the guard member 32 to extend between respective portions of the annular collar 12*d*. Alternatively, the annular collar 12*d* may be radially inwardly spaced apart from the inner surface of the housing 12 in at least one or more locations to facilitate portions of the guard member to extend past the collar 12*d*.

The annular collar 12*d* may further define sloped surfaces 12*e* on opposite sides of each of the lock slots 12*c* to further assist with alignment between the container holder 31 and the housing 12.

The components shown in FIGS. 4A, 4B, and 4C includes an alignment ridge 31*n* that is positioned at the distal end of a support ridge 31*o*. For example, the support ridge 31*o* has a smaller height (measured perpendicularly to the outer surface of the container holder 31) than the alignment ridge 31*n* such that only the alignment ridge 31*n* is received within the alignment slot 12*a*, rather than the support ridge 31*o*. Alternatively, the alignment ridge may extend substantially or completely along the axial length of the container holder 31, as will be discussed below with respect to another exemplary design shown in FIG. 4D.

The drug storage container 20 may be further or more securely coupled with the container holder 31 (and as a result, to the housing 12) such that the drug storage container 20 and the container holder 31 are prevented from moving relative to the housing 12 during operation of the drug delivery device 10. For example, as shown in FIGS. 4B and 4C, the container holder 31 may include a plurality of lock ridges 33*c* on the flanges 33 that form a friction-fit with portion(s) of the housing 12. As a more specific example and as shown in FIGS. 2 & 3B, the housing 12 includes a plurality of lock slots 12*c* that each receive respective lock ridges 33*c* of the container holder 31 to prevent and/or restrict relative movement between the respective components 12, 31. As a more specific example, the lock ridges 33*c* each extend radially from the outer surfaces of the flanges 33. The container holder 31 may include any suitable number of lock ridges 33*c*, such as one, two, three, four, or more. The lock slots 12*c* shown in the figures are defined by the annular collar 12*d*, but they may be alternatively defined by another component. The lock slots 12*c* are spaced apart from each other and sized such as to receive the respective lock ridges 33*c* when the drug storage container is positioned within the container holder 31. As a more specific example, the lock ridges 33*c* snap into a friction-fit with the lock slots 12*c* such as to secure the container holder 31 and, as a result, the drug product container 20, within the housing 12. As an even more specific example, when the lock ridges 33*c* snap into the lock slots 12*c*, the flanges 33 may inwardly compress slightly to form a more-secure fit between the container holder 31 and the drug product container 20.

The container holder 31 inner surface may include a compressible component such as an elastomeric component that is positioned between the inner surface of the container holder 31 and the drug product container 20. As a more specific example, the elastomeric component may be a rubber ring. Alternatively or additionally, the natural flex of the flanges 33 may function as the compressible component.

The lock ridges 33*c* may give audible and/or tactile feedback to the user or an assembly worker as they snap into the corresponding lock slots 12*c*, thereby indicating to the assembler(s) that the respective components 12, 31 are positioned as desired. Additionally, the respective components may be sized and positioned such that the feedback only occurs when the drug product container 20 is also positioned as desired. For example, if the drug product container 20 is positioned too far in the distal direction with respect to the container holder 31, such that the main body of the drug product container 20 is aligned with the flanges 33 instead of the shoulder portion 20*a* being aligned with the flanges 33, then the lock ridges 33*c* may not be able to radially compress enough for the lock ridges 33*c* to fit within the lock slots 12*c*. Conversely, if the drug product container 20 is not inserted far enough in the distal direction with respect to the container holder 31, such that the sterile barrier 21 is aligned with the flanges 33 instead of the shoulder portion 20*a* being aligned with the flanges 33, then the lock ridges 33*c* will be able to radially compress inward to an extent that the lock ridges 33*c* will be able to slide radially inward of the lock slots 12*c* or the lock ridges 33*c* will enter the lock slots 12*c* but may not cause enough radially-outward force to generate the audible and/or tactile feedback. While the audible and/or tactile feedback may be advantageous during manual assembly of the container holder 31, assembly of the container holder 31 need not be performed manually and may in some embodiments be performed partially or entirely by manufacturing equipment.

The housing 12, container holder 31, and their respective components as described above offer many advantages. For example, by securely coupling the drug product container 20 with respect to the housing 12 via the shoulder portion 20*a* (as opposed to the flange portion) the device 10 may have reduced incidence of glass breakage or other damage. As a more specific example, drug product containers such as syringes are often have a shoulder portion that is stronger and/or able to handle higher forces than a flange portion. In other words, it may be advantageous for the force concentration on the drug product container to be higher at the shoulder than at the flange because the shoulder may be stronger and more resistant to breakage than the flange.

As another potential advantage to this configuration, by securely coupling the drug product container 20 with respect to the housing 12 via a distal portion (e.g., the shoulder portion 20*a*) the device 10 may have a more predictable, repeatable, and/or consistent injection depth than designs that secure the drug product container 20 via the flange (e.g. a "hanging" design). For example, the distance between the shoulder portion 20*a* and the delivery member 16 for a syringe is typically more predictable and/or has a smaller manufacturing tolerance than the distance between the flange 20*b* and the delivery member 16 because barrel length of a drug product container 20 can vary more widely than the barrel shoulder length. Additionally or alternatively, the distance between the flange 20*b* and the delivery member 16 includes any tolerances/variances in the distance between the shoulder portion 20*a* and the delivery member 16, so any tolerances/variances are "stacked."

Figure 4F:
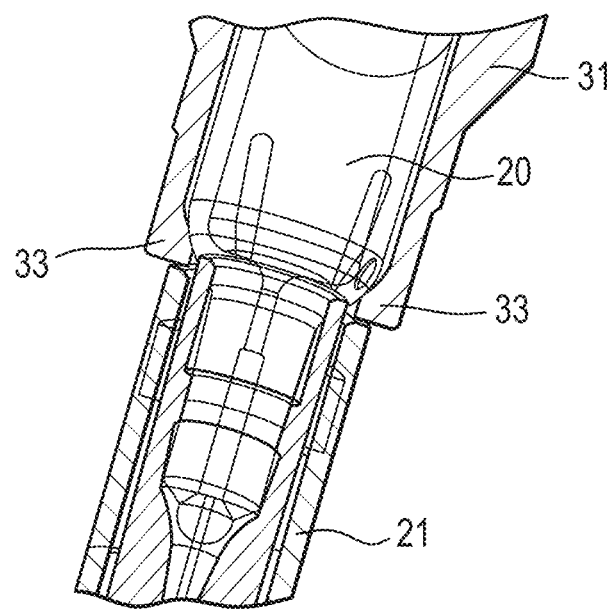
FIG. 4F is a partial cross-sectional view of the container holder and the drug storage container, taken around line 4F-4F in FIG. 4C.

As shown in FIG. 4C, when the drug storage container 20 is inserted into the container holder 31 and the drug storage container 20 is in the closed position 29*b*, a portion of the drug storage container 20 extends past the distal end of the container holder 31. For example, the sterile barrier 21 is positioned substantially or completely outside of the container holder 31 to facilitate removal of the sterile barrier 21 during use of the device 10, as is shown in FIGS. 4C and 4F and as will be discussed in more detail below. Additionally, the delivery member 16 extends past the distal end of the container holder 31 (as discussed above).

FIG. 4D shows another exemplary container holder 131 that has some features which are similar in function to those included in the container holder 31, each of which is assigned with same reference numeral except incremented by 100. For example, the container holder 131 includes a pair of arms 131a, 131b; an annular ring 131c connecting the arms 131a, 131b; respective sets of mating connectors 131d, 131e, 131k, 131m for selectively fixing the arms in a closed position 129b; a pair of inwardly-protruding flanges 131f, 131g; a pair of opposing surfaces 131h, 131i for defining lower and upper limits of travel for the drug storage container flange; and an opening 131j for receiving the drug storage container flange. The container holder 131 also includes a plurality of flanges 133 positioned at a distal end of the container holder 131 and configured to support the drug storage container. For example, the container holder 131 includes two flanges 133, each of which includes an arcuate, sloped surface 133a that substantially matches the arcuate shape of a shoulder portion of the drug storage container. The container holder 131 shown in FIG. 4D has two flanges 133 as opposed to the four flanges 33 shown in the container holder 31 shown in FIGS. 4A-4C; therefore the flanges 133 each preferably have a greater circumference than the flanges 33. The container holder 131 also includes an alignment ridge 131n that is received within an alignment slot 12a formed in the inner surface of the housing 12 to properly align the container holder 131 within the housing 12 during assembly and to prevent and/or restrict rotational movement between the respective components 12, 131. The alignment ridge 131n shown in FIG. 4D extends substantially completely along the axial length of the container holder 131, in contrast to the alignment ridge 31n.

As with the container holder 31 shown in FIGS. 4B-4C, the container holder 131 may include a plurality of lock ridges 133c on the flanges 133 that form a friction-fit with portion(s) of the housing 12. As a more specific example and as shown in FIGS. 4D and 4E, the housing 12 includes a plurality of lock slots 12c that each receive respective lock ridges 133c of the container holder 131 to prevent and/or restrict relative movement between the respective components 12, 131. The lock ridges 133c may also give audible and/or tactile feedback to the user or an assembly worker as they snap into the corresponding lock slots 12c, thereby indicating to the assembler(s) that the respective components 12, 131 are positioned as desired. Additionally, the container holder 131 may provide the same or similar advantages as those described above with respect to the container holder 31.

In yet another exemplary design, the container holder may have a fixed state, rather than having arms that open and closed. As a more specific example, the container holder may have a proximal opening sufficiently sized to permit receipt of the syringe. The container holder may still have distally-located flanges for receiving and securing the shoulder portion of the syringe, particularly when the container holder is coupled with the injector housing.

Figure 5A:
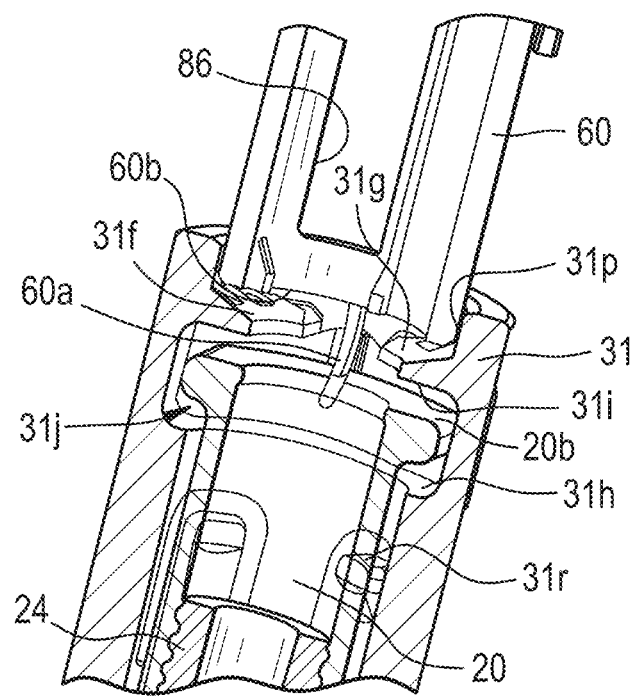
FIG. 5A is a partial cross-sectional view of the container holder, the drug storage container, taken around line 5A-5A in FIG. 4C, as well as a partial cross-sectional view of a distal portion of an exemplary plunger guide coupled with the container holder and the drug storage container.

FIGS. 4F and 5A show distal (FIG. 4F) and proximal (FIG. 5A) portions of the drug product container 20 and its interactions with various other components of the device 10. For example, FIG. 4F shows a partial cross-sectional view of a distal portion of the drug product container 20 positioned within the container holder 31, with the shoulder portion 20a supported by the flanges 33. As another example, FIG. 5A shows a cross-sectional view of a proximal portion of the drug product container 20 positioned within the container holder 31 such that the drug product container flange 20b is positioned between the opposing surfaces 31h, 31i and within the opening 31j. The drug product container 20 shown in FIG. 5A is further supported by the plunger guide 60, such as a flexible arm 60a of the plunger guide 60. As a more specific example, the flexible arm 60a extends generally distally, and slightly radially inwardly, from a distal portion of the plunger guide 60b. As an even more specific example, the plunger guide 60 shown in FIG. 5A includes a distal surface 60b that abuts the inwardly-protruding flanges 31f, 31g of the container holder 31; the flexible arm 60a extends from the distal surface 60b in between the inwardly-protruding flanges 31f, 31g.

The flexible arm 60a may have a size, shape, and material type that promotes and/or permits flexure of the flexible arm 60a. As a more specific example, the flexible arm 60a is preferably flexible in the radial direction, so that when the drug product container 20 and the plunger guide 60 are inserted within the housing, the flexible arm 60a is aligned with the flange 20b and applies at least a gentle radial force (radially inwardly) on the drug product container 20. In this configuration, the drug product container 20 is primarily supported at its distal portion (e.g., the shoulder portion 20a) by the container holder 31 and is also, at least secondarily, supported at its proximal portion (e.g., the flange portion 20b) by the plunger guide 60. As a more specific example, the flexible arm 60a may provide radial support to the flange portion 20b and prevent and/or resist transverse movement of the drug product container 20 with respect to the housing 12. Such a configuration may reduce or eliminate rattling noises from the device 10 and/or may facilitate proper alignment of the drug product container 20 during assembly. As another more specific example, the flexible arm 60a may provide axial support (e.g., in the distal direction) to prevent undesirable axial movement of the drug product container 20 with respect to the housing 12. The device 10 may have any suitable number of flexible arms 60a, such as one, two, three, four, or more.

The container holder 31 may also include at least one support flange 31r that has a size, shape, and material type that promotes and/or permits flexure thereof. As a more specific example, the support flange 31r is preferably flexible in the radial direction, so that when the drug product container 20 and the container holder 31 are inserted within the housing, the support flange 31r is aligned with the body portion 20g of the drug product container and applies at least a gentle radial force (radially inwardly) on the drug product container 20. In this configuration, the drug product container 20 is primarily supported at its distal portion (e.g., the shoulder portion 20a) by the container holder 31 and is also, at least secondarily, supported at a central or proximal region of the body portion 20g by the container holder 31. As a more specific example, the support flange 31r may provide radial support to the drug product container 20 and prevent and/or resist transverse movement of the drug product container 20 with respect to the housing 12. Such a configuration may reduce or eliminate rattling noises from the device 10 and/or may facilitate proper alignment of the drug product container 20 during assembly. As another more specific example, the support flange 31r may but is not required to provide axial support (e.g., in the distal direction) to prevent undesirable axial movement of the drug product container 20 with respect to the housing 12. The device 10 may have any suitable number of support flanges 31r, such as one, two, three, four, or more. The container holder 31 shown in the figures includes four support flanges 31r that are equally spaced about the circumference thereof.

Although the flexible arm 60a and/or the support flanges 31r shown in the figures provides at least some support for the drug storage container 20, the container holder substantially completely supports the drug storage container 20 with respect to the housing 12 by the distal end of the body portion 20g of the drug storage container 20, as discussed above. As a more specific example, the flexible arm 60a and/or the support flanges 31r may provide little or no support along the longitudinal axis A and only provide support in a direction transverse to Axis A. As an even more specific example, the container holder 31 substantially completely supports the drug storage container 20 with respect to the housing 12 by the distal end of the body portion 20g of the drug storage container 20 for forces along the Axis A, such as forces experienced during the injection process.

As indicated above, the plunger guide 60 shown in FIG. 5A includes a distal surface 60b that abuts the inwardly-protruding flanges 31f, 31g of the container holder 31. This configuration may help reduce or prevent radial movement of the container holder 31 within the housing 12. For example, as shown in FIG. 5A, the container holder includes an annular wall 31p that cooperates with the inwardly-protruding flanges 31f, 31g to define an annular seat for the distal surface 60b of the plunger guide 60. The annular wall 31p may center the plunger guide 60 with respect to the container holder 31 and the drug product container 20 so that the plunger 26 is likewise aligned with those components 31, 20. The annular wall 31p may also reduce or prevent radial movement of the plunger guide 60 with respect to the housing 12. This configuration may also help reduce or prevent axial movement of the container holder 31 within the housing 12. For example, as shown in FIG. 2, the plunger guide 60 extends from the rear end cap 23 to a mid-point of the device 10 where it abuts the container holder 31. As a result, the container holder 31 is restricted from moving axially upward in FIG. 2 (i.e., proximally) by the plunger guide 60. Furthermore, the rear end cap 23 may not be able to be installed unless the plunger guide 60 is properly axially and radially aligned with the container holder 31, such as if the distal surface 60b is not abutting the inwardly-protruding flanges 31f, 31g.

Figure 5B:
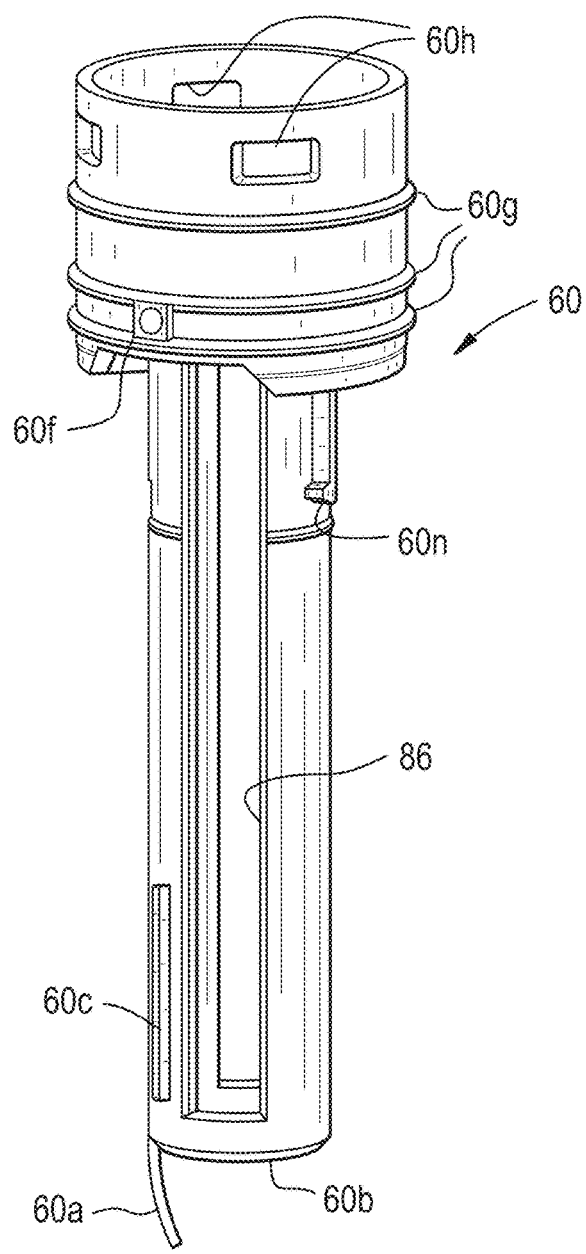
FIG. 5B is a perspective view of an exemplary plunger guide in accordance with various embodiments.
Figure 5C:
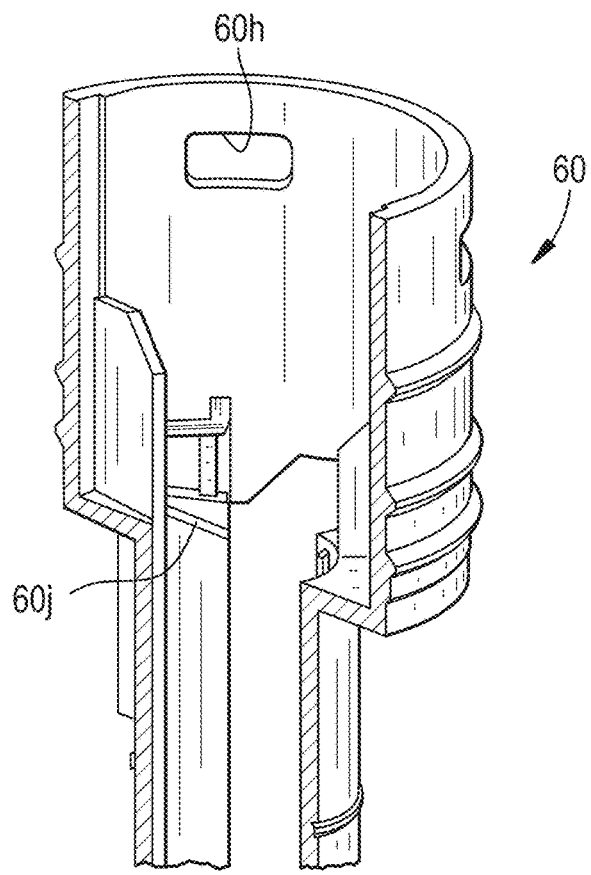
FIG. 5C is a perspective, partial cross-sectional view of the plunger guide in FIG. 5B.

As shown in FIGS. 5B and 5C, the plunger guide 60 may have a hollow and generally cylindrical or tubular shape, and may be centered about the longitudinal axis A. An outer diameter or other outer dimension of a proximal end of the plunger guide 60 may be larger than an outer diameter or other outer dimension of a distal end of the plunger guide 60. At least a portion of the distal end of the plunger guide 60 may be positioned radially between the plunger 26 and the releaser member 52. As such, the plunger 26 may be disposed at least partially within the distal end of the plunger guide 60, and the distal end of the plunger guide 60 may be disposed at least partially within the releaser member 52, as illustrated in FIG. 2. Further features and functions of the plunger guide 60 are discussed below.

As shown in FIG. 2, the plunger guide 60 may be fixedly coupled with the housing such that the plunger guide 60 is substantially and/or generally immovable relative to the housing 12. For example, and as shown in FIGS. 1C and 5B, the plunger guide includes a lock tab 60f that is sized, shaped, and aligned to be received within a lock key 12f formed within the housing 12. As a more specific example, the plunger guide 60 and housing 12 each include a pair of respective components 60f, 12f that cooperate to prevent relative rotation between the plunger guide 60 and the housing 12. Additionally or alternatively, annular ridges 60g formed on an outer surface of the plunger guide 60 may form a friction fit with the inner surface of the housing to resist or prevent rotation between the respective components 12, 60.

The plunger 26 (as best illustrated in FIGS. 2, 3A) may have a hollow and generally cylindrical or tubular shape. The plunger 26 may include an annular wall 39 with an outer surface 41 and an inner surface 43. The inner surface 43 may define an interior space sized to receive a plunger biasing member 50 therein. It is generally desirable to minimize a thickness of the annular wall 39, to the extent possible and without compromising the integrity of the plunger 26, so as to maximize an inner diameter of the plunger 26. This allows a larger diameter plunger biasing member 50 to fit within the interior space of the plunger 26, which, in turn, allows for a more powerful plunger biasing member 50. As a more specific example, the thickness of the annular wall 39 may be less than 2 mm. As another more specific example, the thickness of the annular wall may be less than 1 mm. As another more specific example, the thickness of the annular wall may be less than 0.6 mm. As another more specific example, the thickness of the annular wall may be less than 0.3 mm. As another more specific example, the thickness of the annular wall may be less than 0.2 mm. As another more specific example, the thickness of the annular wall may be less than 0.1 mm. As another more specific example, the thickness of the annular wall may be less than 0.05 mm. The annular wall 39 may be made of any suitable material, such as metal or plastic. It may be advantageous for the annular wall 39 to be made of metal, such as steel or aluminum, for the purposes of minimizing the thickness of the annular wall 39. For example, a metal annular wall 39 may have sufficient axial strength and/or buckle resistance for use in the device if the annular wall 39 thickness is greater than 0.05 mm. Conversely, a plastic annular wall 39 may have sufficient axial strength and/or buckle resistance for use in the device if the annular wall 39 thickness is greater than 1 mm.

The hollow rod 46 may additionally or alternatively facilitate and/or provide more flexibility in spring design. For example, it may be desirable or advantageous to use the device with different springs depending on the characteristics of the drug and/or the desired drug delivery profile. For example, a higher viscosity drug may require a spring with a higher spring rate and/or spring force and it thus may be desirable or advantageous to have flexibility in physical characteristics of the spring. As a more specific example, various physical characteristics of a spring may affect the spring rate, and thus the spring force, such as wire diameter of the spring (typically increasing the wire diameter increases the spring rate), mean diameter of the spring (typically increasing the mean diameter decreases the spring rate), the number of spring coils (typically increasing the number of coils increases the spring rate), and the spring material. These physical characteristics may be adjusted to deliver different spring rates, while also potentially adjusting the thickness of the hollow rod 46, to maintain a constant or relatively constant outer diameter of the overall plunger 26 so as to keep constant the remaining parts of the device, such as the plunger guide 60 and the stopper 24. The hollow rod 46 may additionally or alternatively facilitate and/or provide more longitudinal stability for the plunger biasing member 50, such as by preventing or reducing buckling or other transverse movement.

The plunger biasing member 50 shown in the figures may include the following dimensions: 0.65 mm wire diameter, 5.40 mm outer diameter of the spring, and 80 to 86 number of coils (depending on pitch), but other suitable spring characteristics may be utilized. The plunger biasing member 50 shown in the figures may be formed of stainless steel strength 2300 n/mm, but other suitable materials may be utilized. The hollow rod 46 shown in the figures may include the following dimensions and materials: 63 mm length, 6 mm outer diameter, 0.20 mm wall thickness, and stainless steel strength 600 to 750 n/mm material, but other suitable dimensions and materials may be utilized.

As described below in more detail, the plunger 26 may be configured to selectively rotate relative to the housing 12 and translate linearly relative to the housing 12 during operation of the drug delivery device 10.

The plunger 26 may be constructed of multiple, interconnected pieces, or alternatively, have a one-piece construction. In the present embodiment, the plunger 26 is constructed of three separate and interconnected structures: a top ring 45 defining a proximal end of the plunger 26; a base 47 defining a distal end of the plunger 26; and a hollow rod 46 positioned between and rigidly connecting the top ring 45 and the base 47. The positions of the top ring 45, the hollow rod 46, and the base 47 may be fixed relative to each other such that these components are immoveable relative to each other. The top ring 45, the hollow rod 46, and the base 47 may each have an annular construction and be centered about the longitudinal axis A. The top ring 45 and the hollow rod 46 may each have a respective central opening extending from end to end of the component to define an axial chamber; whereas, the base 47 may have a central opening extending through the proximal end of the base 47 but which is closed off at the distal end of the base 47. The closed off end of the base 47 may define seat or abutment surface for the plunger biasing member 50. In alternative embodiments, the central opening may extend through the base 47 from end to end. In such alternative embodiments, an inner diameter of the central opening of the base 47 may be smaller than an outer diameter of the plunger biasing member 50 such that the base 47 retains a distal end of the plunger biasing member 50 within the plunger 26. When the drive mechanism 30 is activated, the base 47 may be the portion of the plunger 46 that comes into contact with the stopper 24 to push the stopper 24 in the distal direction.

The top ring 45 may include one or more flanges or projections 48 which extend radially outwardly from a central portion of the top ring 45. Each of the projections 48 may include a distally facing camming surface 49. As described below in more detail, the distally facing camming surface 49 may interact with a counterpart camming surface on a plunger guide 60 in order to release the plunger biasing member 50. In some embodiments, the distally facing camming surface 49 may arranged at angle relative to, or is otherwise non-parallel to, an imaginary plane perpendicular to the longitudinal axis A.

In some embodiments, the top ring 45 and/or the base 47 may be constructed of a different material than the hollow rod 46. In some embodiments, the top ring 45 and/or the base 47 made be constructed of plastic whereas the hollow rod 46 may be constructed of metal. So configured, the plastic material used for the top ring 45 may facilitate the camming action described below by providing a relatively low coefficient of friction, the plastic material used for the base 47 may help absorb or attenuate any shock or vibrations associated with base 47 striking the stopper 24. The metal material used for the hollow rod 46 may provide sufficient rigidity to avoid buckling under the biasing force exerted by the plunger biasing member 50. In alternative embodiments, the top ring 45, hollow rod 46, and/or base 47 may be made of the same material, including, for example, metal or plastic. In certain such embodiments, the top ring 45, hollow rod 46, and base 47 may be integrally formed in one piece so as to define single, monolithic structure.

The drug delivery device 10 may further include a guard mechanism for preventing contact with the insertion end 28 of the delivery member 16 when the drug delivery device 10 is not being used to administer an injection. The guard mechanism may include a guard member 32 moveably disposed at or near the distal end of the housing 12 adjacent to the opening 14. The guard member 32 may have a hollow and generally tubular-shaped or cylindrical portion 32a centered about the longitudinal axis A, and may have a pair of arms 32b extending proximally from the cylindrical portion 32a. The guard member 32 further includes a distal end 32c that may generally include the cylindrical portion 32a and a proximal end 32d that may be defined by the arms 32b. The arms 32b may be substantially or completely received within the housing 12 such that no part thereof extends from the housing 12. The cylindrical portion 32a may be at least partially and/or selectively received within the housing 12. For example, the guard member 32 may be configured to move relative to the housing 12 such that portions of the guard member 32 are received within the housing 12 in some stages/states and are extending from the housing 12 in other stages/states, as is discussed below in more detail.

Figure 6A:
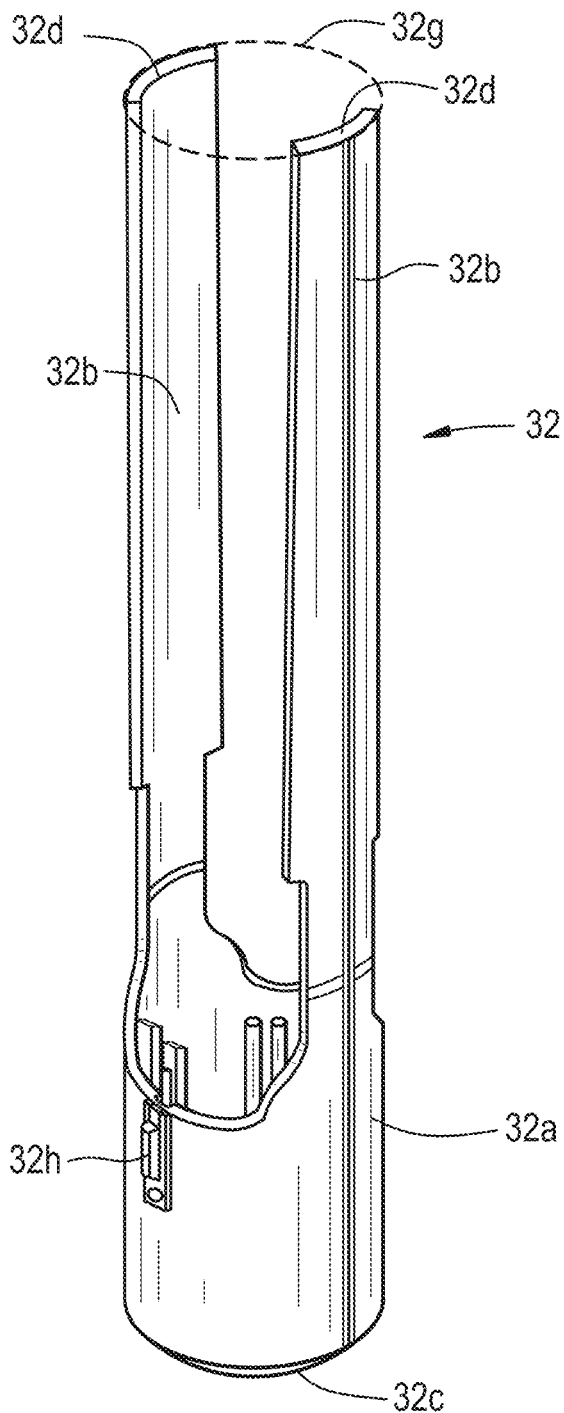
FIG. 6A is a perspective view of an exemplary guard member in accordance with various embodiments.

As one exemplary configuration, shown in FIGS. 2, 4E, and 6, the arms 32b of the guide member 32 are radially spaced apart from each other along a circumference 32g of the guard 32 such that the arms 32b are able to slide between protruding sections of the annular collar 12d formed on the inner surface of the housing 12. For example, that the length of the arc between respective edges of the arms 32b is at least slightly larger than an arcuate length of a protruding section of the annular collar 12d so that the arms are able to axially slide between the protruding sections of the annular collar 12d without contacting the collar.

As indicated above, the guard member 32 may be configured to move relative to the housing 12 between an extended position wherein at least a portion of the cylindrical portion 32a of the guard member 32 extends through the opening 14 in the housing 12 and a retracted position wherein a shorter length of the cylindrical portion 32a or no part of the cylindrical portion 32a extends through the opening 14 in the housing 12. In other words, in the extended position, a length X of the cylindrical portion 32a extends from through the opening 14 in the housing 12 and in the retracted position, a length Y of the cylindrical portion 32a extends through the opening 14 in the housing 12, wherein X is a value greater than Y. The length X may be any suitable number such as 10 mm, 8 mm, 6 mm, 4 mm, 2 mm, 1 mm, or another value. The length Y may be any suitable number that is less than X, such as 3 mm, 2 mm, 1 mm, 0.5 mm, 0 mm, or another value. FIGS. 1C and 1D illustrate an exemplary pre-injected configuration (FIG. 1C) where the guard member 32 is an extended position 32e and the length of the exposed portion X of the guard member 32 may be approximately 5 mm to 11 mm and an injection configuration (FIG. 1D) where the guard member 32 is in a retracted position 32f and the length of the exposed portion Y of the guard member 32 is approximately 0 mm to 2 mm (such that the distal end 32c of the guard member 32 is flush with the opening 14 of the housing 12). In one embodiment, the distance Y is greater than 0 (e.g. 1 mm) to help ensure the device 10 is able to be activated before the guard member is flush with the housing 12.

The guard member 32 may also be configured to move in the opposite direction, namely from the retracted position to the extended position. When moving from the extended position to the retracted position, the guard member 32 may translate linearly in the proximal direction; and when moving from the retracted position to the extended position, the guard member 32 may translate linearly in the distal direction. In at least the extended position, the guard member 32 may extend beyond and surround the insertion end 28 of the delivery member 16. As a further illustration, FIGS. 1C and 2 show the guard member 32 in the extended position (and covered by the removable cap 19 in FIG. 2). As discussed above, moving the guard member 32 from the extended position to the retracted position, e.g., by pressing the distal end of the guard member 32 against the patient's skin at the injection site, may result in the insertion end 28 of the delivery member 16 being inserted into the patient's skin.

During the injection process the guard member 32 may remain stationary with respect to the user's skin 5 while the housing 12 and several components disposed therein are moving with respect to the guard member 32 and the skin 5. Nonetheless, this disclosure refers to moving, retracting, translating, and depressing the guard member 32. These references and descriptions may be considered to refer to relative movement between the guard member 32 and the housing 12, regardless of which component (guard member 32 or housing 12) is moving with respect to the user's skin 5.

The delivery device 10 may utilize inertial-driven design, rather than a spring-driven design, to insert the needle into the patient's subcutaneous tissue. As a more specific example, when the patient presses the distal end of the guard member 32 against the patient's skin at the injection site, the delivery device 10 housing 12 may advance toward the injection site. As the patient presses down a predetermined distance or with a predetermined force, the delivery device 10 achieves a quick release to harness the energy stored in the patient's muscles while compressing the needle cover and its spring to a defined release point. The release mechanism is designed such that the resulting needle insertion speed exceeds the patient's reaction speed, and the combination of this speed and the device's mass cause the needle to quickly and fully penetrate the skin to the subcutaneous depth. Compared to known injectors, where the entire primary container is moved forward with respect to the housing, this embodiment prevents relative movement between the drug storage container 20 and the housing and therefore may provide a simplified, more robust design.

In alternative embodiments, the drug storage container 20 may be moveably coupled to the housing 12 such that the drug storage container 20 is able to move relative to the housing 12 during operation of the drug delivery device 10. In certain such alternative embodiments, the insertion end 28 of the delivery member 16 may be retracted within the opening 14 in the housing 12 in the pre-delivery state. Subsequently, during operation of the injection device 10, the insertion end 28 of the delivery member 16 may be deployed through the opening 14 in the housing 12 for insertion into the patient. This motion may, in some embodiments, be the result of the drug storage container 20 having been driven in the distal direction relative to the housing 12.

In some embodiments, the guard member 32 may be rotationally fixed or rotationally restricted relative to the housing 12. Therefore, although the guard member 32 may able to translate linearly relative to the housing 12, the guard member 32 may be substantially or completely prevented from rotating relative to the housing 12. As a more specific example, the cylindrical portion 32a of the guard member 32 may include a protrusion extending therefrom, for example a ridge 32h, that aligns with a corresponding feature on the inner surface of the housing 12. For example, the inner surface of the housing, adjacent to the distal end of the housing 12 may include a slot, a pair of adjacent ridges, or another component or set of components that cooperate with the ridge 32h to substantially or completely prevent rotation of the guard member 32. This arrangement may also help align the respective components 32, 12 with each other during assembly.

The device 10 may further include an extender biasing member 35 and a guard extension 37. The guard extension 37 may be positioned proximal to the guard member 32; and the extender biasing member 35 shown in the figures is positioned proximal to the guard extension 37. The guard extension 37 may have a hollow and generally cylindrical or tubular shape centered about the longitudinal axis A. As a more specific example, the guard extension 37 may include a generally cylindrical body 37a. The guard extension 37 may also include arms 37b for receiving, supporting, and/or retaining a distal portion of the extender biasing member 35. Furthermore, the guard extension 37 may be moveable in a linear direction along the longitudinal axis A relative to the housing 12. In the present embodiment, the guard extension 37 is a separate structure from the guard member 32. However, in alternative embodiments, the guard extension 37 and the guard member 32 may be integrally formed in one piece to define a single, monolithic structure. In such alternative embodiments, the proximal end of the guard member 32 may correspond to the guard extension 37.

Similar to the guard member 32, the guard extension 37 may be rotationally fixed relative to the housing 12. Therefore, although the guard extension 37 may able to translate linearly relative to the housing 12, the guard extension 37 may be prevented from rotating relative to the housing 12. To achieve this effect, in some embodiments the guard extension 37 may cooperate with the plunger guide 60 to restrict or prevent rotation between the respective components 37, 60. As a result, and because the plunger guide 60 is fixedly connected with the housing 12, the guard extension 37 may be rotationally fixed to the housing 12 through the plunger guide 60. For example, the plunger guide 60 may include a longitudinal ridge 60c near a distal portion of the plunger guide 60. The ridge may be received within a longitudinal channel on the inside surface of the guard extension 37 and/or a pair or corresponding features that cooperate to receive the ridge 60c. In alternative embodiments, the ridge-and-slot arrangement may be reversed, such that the guard extension 37 has one or more radially inwardly extending ridges and plunger guide has one or more slots or other recesses to matingly or snugly receive the one or more ridges. As yet another alternative, the guard extension 37 may include an anti-rotation feature that mates with a corresponding feature on the inner surface of the housing 12.

Figure 6B:
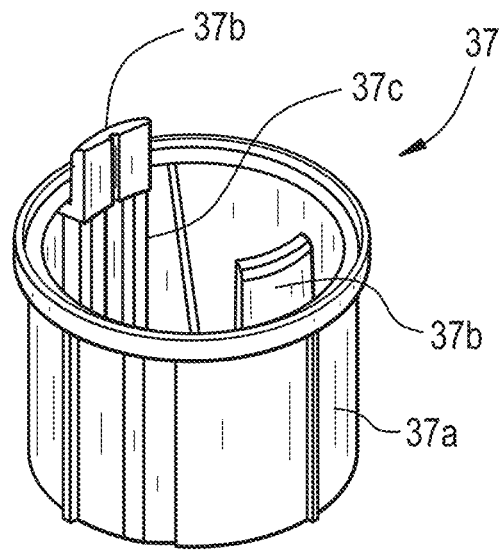
FIG. 6B is a perspective view of an exemplary guard extension in accordance with various embodiments.
Figure 6C:
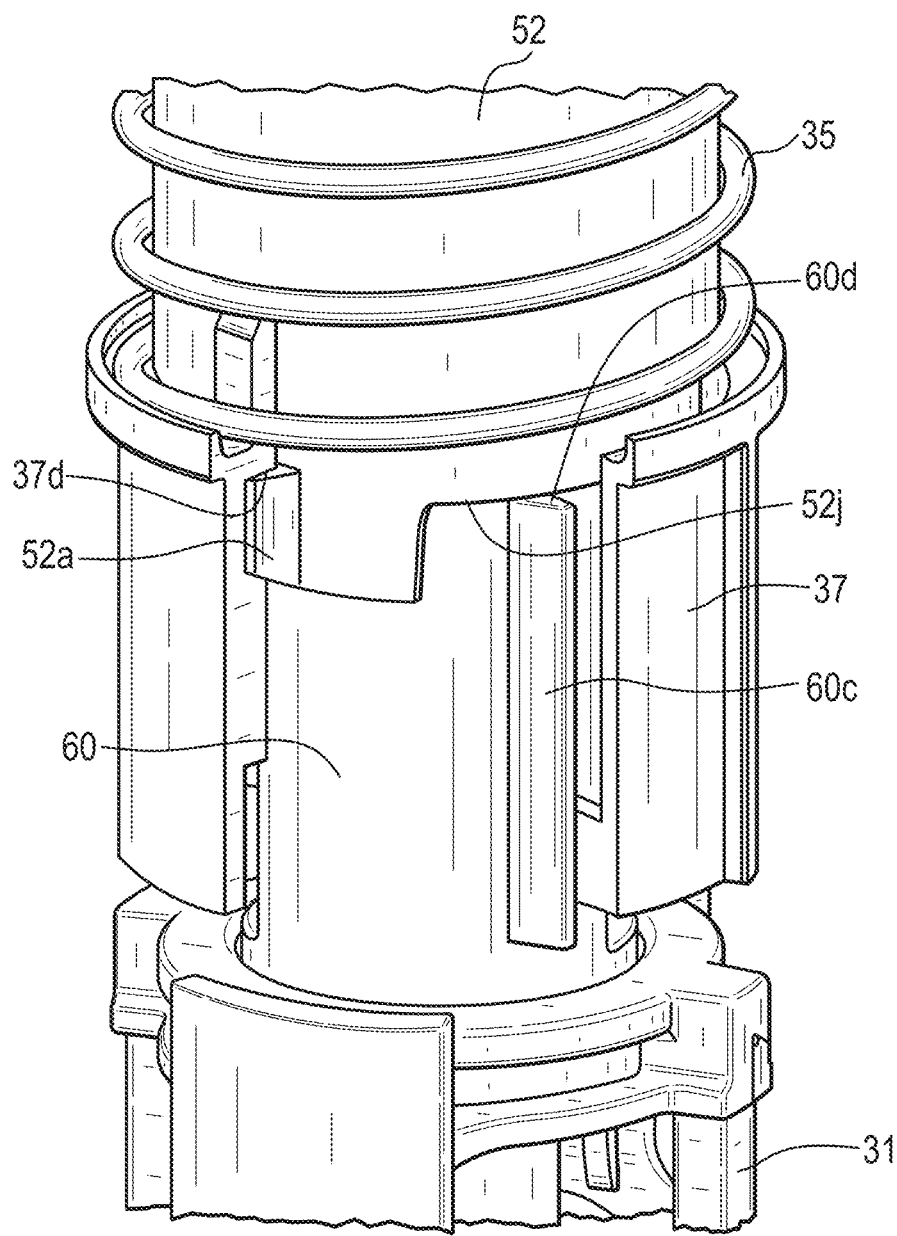
FIG. 6C is a perspective, partial cross-sectional, view of the guard extension, the releaser, and the plunger guide, wherein the components are in a pre-injection position.

The guard extension 37 and/or the releaser member 52 may have axial travel limits that limit the distance they are able to travel in the distal direction. For example, as illustrated in FIG. 6C, the plunger guide 60 may include and axial ridge 60c formed on the outer surface and positioned adjacent to a distal portion of the plunger guide 60. A distally facing surface 52j of the releaser member 52 may abut a proximally facing surface 60d defined by the axial ridge 60c, thereby defining the distal-most point of travel for the releaser member 52. The releaser member 52 also may include the locking flange 52a that in turn limits the distal travel of the guard extension 37. For example, the locking ridge 52a may abut an annular collar 37d of the guard extension 37 to define the distal-most point of travel for the guard extension 37. The axial ridge 60c and the locking ridge 52a shown in the figures do not necessarily limit travel of the releaser member 52 and the guard extension 37 in the proximal direction, just the distal direction.

As is best illustrated in FIG. 2, the extender biasing member 35 is positioned between and in contact with the guard extension 37 and a releaser member 52. The extender biasing member 35 may be configured to bias or urge the guard extension 37 in the distal direction and/or bias or urge the releaser member 52 in the proximal direction. In the device 10 shown in FIG. 2, which is in the pre-delivery or storage state, the extender biasing member 35 is initially in an energized state (e.g., compressed). In other words, when the device 10 is in the pre-delivery state, as shown in FIG. 2, the extender biasing member 35 exerts a distal direction (downward) biasing force on the guard extension 37 and a proximal direction (upward) biasing force on the releaser member 52.

During operation of the device, a user may cause the guard member 32 to translate (with respect to the housing 12) in the proximal direction by pressing the guard member 32 against the injection site. In doing so, the guard member 32 will move towards the guard extension 37 and close the gap 37g therebetween (FIG. 2). Once the gap 37g is eliminated, the guard member 32 and the guard extension 37 move jointly in the proximal direction until, for example, the guard member 32 reaches the retracted position 32f. When the injection is complete and the drug delivery device 10 is lifted off of the injection site, the extender biasing member 35 may urge the guard extension 37 so that the guard extension 37 and the guard member 32 move jointly in the distal direction. This motion (and/or a biasing force from lock ring biasing member 51) returns the guard member 32 to the extended position 32e, which has the effect of covering the insertion end 28 of the delivery member 16. In some embodiments, the extender biasing member 35 may include a compression spring (e.g., a helical compression spring). Furthermore, in embodiments where the plunger biasing member 50 also includes a compression spring, the extender biasing member 35 may disposed around and/or have a larger diameter than the plunger biasing member 50.

However, in some alternative embodiments, the extender biasing member 35 may be in non-energized (natural) state when the device is in a pre-delivery state. In these embodiments, the biasing member 35 may become compressed or energized upon deflection of the guard member 32 in the proximal direction.

After drug delivery is complete and the guard member 32 has been re-deployed to the extended position, it may be desirable to lock the guard member 32 in the extended position to prevent subsequent user contact with the insertion end 28 of the delivery member 16 and/or to prevent re-use of the drug delivery device 10. Pursuant to these ends, some embodiments of the drug delivery device 10 may include a lock ring 40 configured to selectively rotate, depending on the axial position of the guard member 32, in order to lock the guard member 32 in the extended position once the guard member 32 has moved from the retracted position to the extended position, as will be discussed in more detail below.

As discussed above, the plunger biasing member 50 may be disposed at least partially within the plunger 26, and may have a distal end abutting against a proximally facing inner surface of the plunger 26 and/or may be fixedly attached to an inner surface of the plunger 26. So that the plunger biasing member 50 may be received within the plunger 26, an outer diameter or other dimension of the plunger biasing member 50 may be equal to or less than an inner diameter of the top ring 45 and/or equal to or less than an inner diameter of the hollow rod 46. In some embodiments, the distal end of the plunger biasing member 50 may abut against a proximally facing inner surface of the base 47 of the plunger 26. Furthermore, as best illustrated in FIGS. 2 and 3A, a proximal end 50a of the plunger biasing member 50 may abut against a distally facing surface 38a of the plunger biasing member seat 38. The plunger biasing member seat 38 may be fixedly attached to the rear housing 27 such that the plunger biasing member seat 38 provides a stationary surface for the plunger biasing member 50 to push off of. For example, as shown in FIGS. 3A and 5B, the plunger seat 38 may include flanges 38b that are received within openings 60h formed in a proximal portion of the plunger guide, thereby fixedly coupling the plunger seat to the plunger guide 60. So configured, the plunger biasing member 50, when released from the energized state, may expand in length with distal end of the plunger biasing member 50 moving in the distal direction away from the stationary proximal end of the plunger biasing member 50. This motion may push the plunger 26 is the distal direction, which, in turn, may push the stopper 24 in the distal direction to expel the drug 22 from the drug storage container 20 into the delivery member 16 and thereafter into the patient. However, in the embodiment shown in the figures, neither the release of the plunger biasing member 50 nor any other biasing members cause the delivery member 16 to drive downward with respect to the housing 12. On the contrary, the drug product container 20, and a as a result the delivery member 16, is substantially or completely fixedly coupled with respect to the housing 12. Rather, the delivery member 16 is driven into the patients skin 5 by inertial force generated by a downward force by the patient (or a health care provider or other person administering the dose).

Figure 7A:
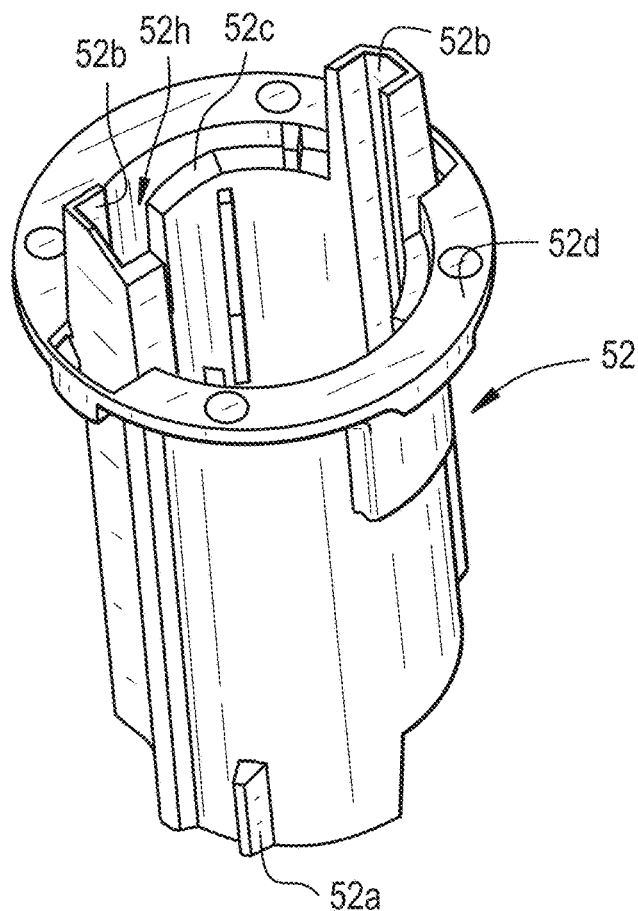
FIG. 7A is a perspective view of an exemplary releaser member in accordance with various embodiments.
Figure 7B:
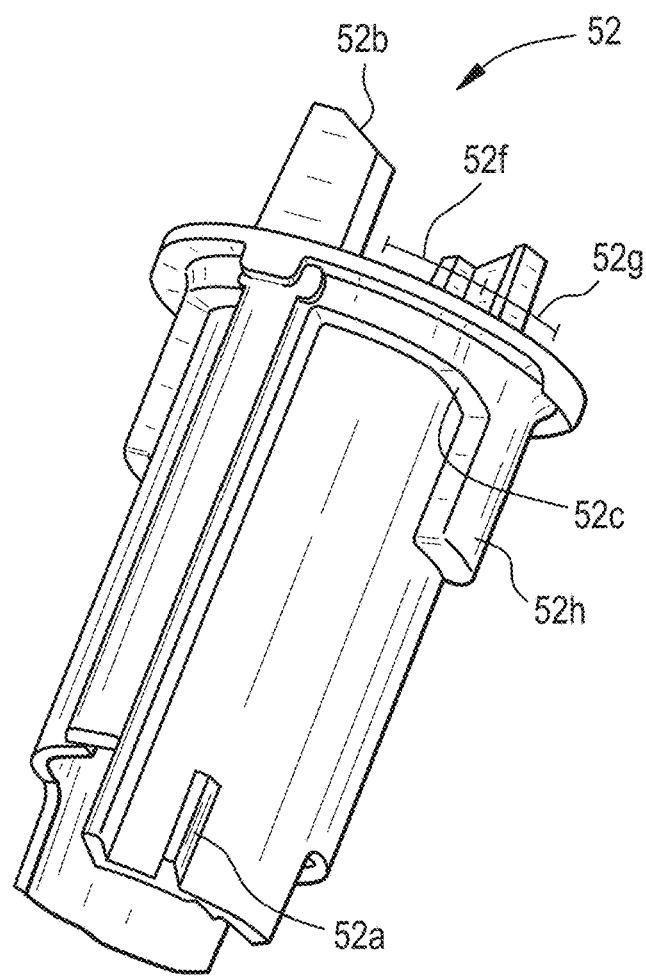
FIG. 7B is another perspective view of the releaser member in FIG. 7A.
Figure 8:
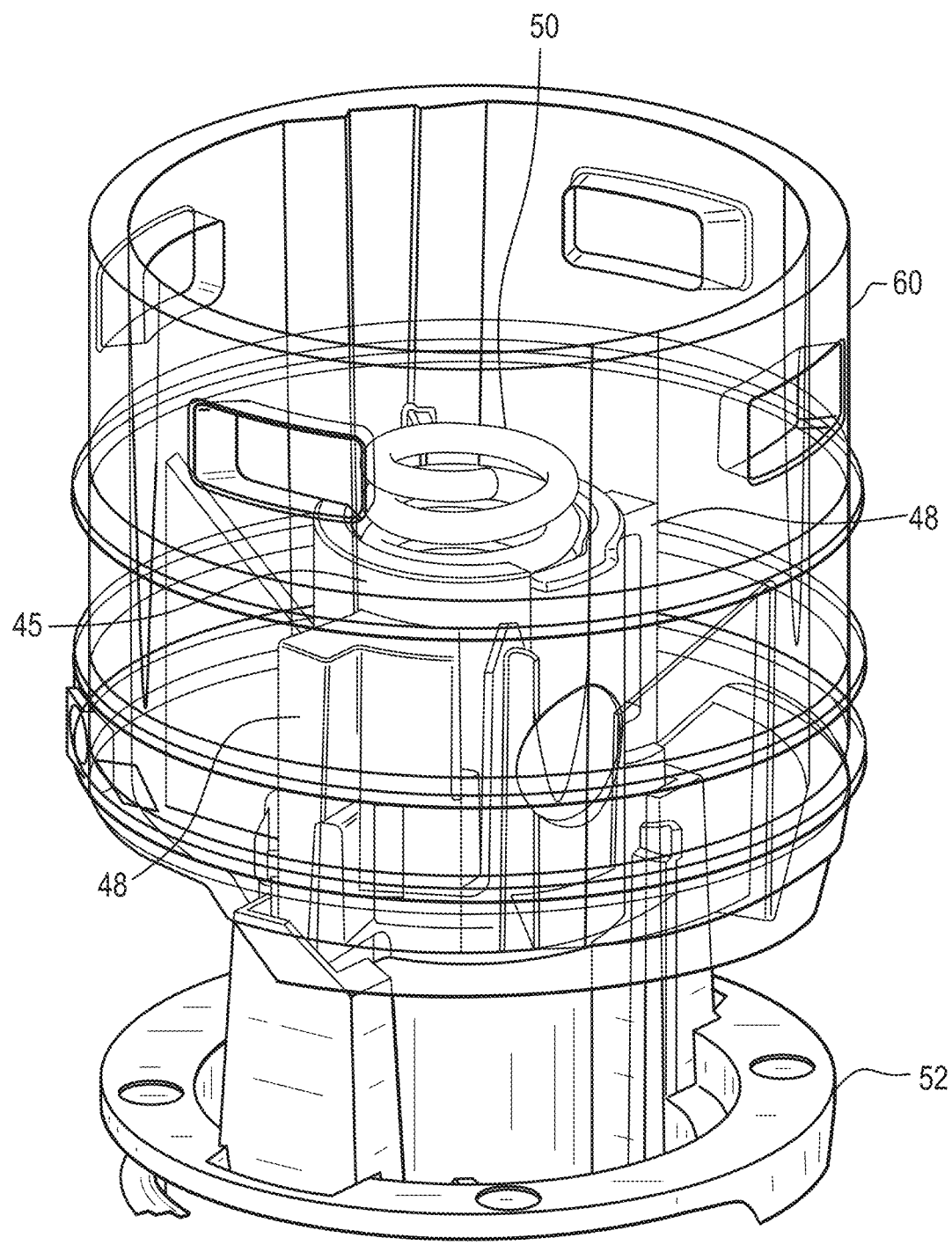
FIG. 8 is a perspective view of the plunger guide from FIG. 5B, the releaser member from FIG. 7A, and the plunger 26 shown in FIG. 2, wherein the guide member is shown in translucent form for illustrative purposes.

Referring to FIGS. 7A and 7B, of the releaser member 52 may have a hollow and generally cylindrical or tubular shape, and may be centered about the longitudinal axis A. As illustrated in FIG. 2, the releaser member 52 may be radially positioned between the plunger guide 60 and the guard extension 37. As also illustrated in FIG. 2, the releaser member 52 is also radially positioned between the guard extension 37 and the plunger guide 60. Furthermore, the extender biasing member 35 may be axially positioned between the releaser member 52 and the guard extension 37 and may be radially arranged around the releaser member 52. Generally, the releaser member 52 is configured to: (1) operably couple the guard member 32 and the plunger 26 in an activation sequence and (2) generate an audible signal indicating the end of drug delivery. So configured, the releaser member 52 is exploited to perform two separate functions, and thus reduces the number of moving parts required by the drug delivery device 10.

Figure 10A:
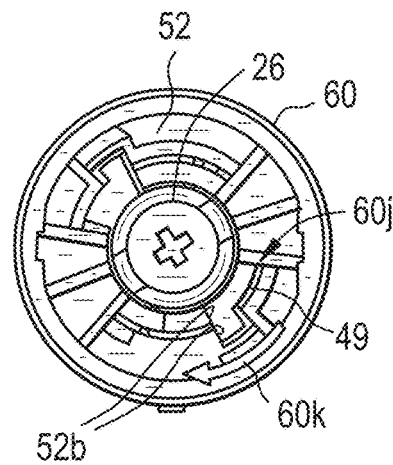
FIG. 10A is a top view of the components in FIG. 9A, wherein the drug delivery device is in the pre-injection position.

The channel surfaces 52b are each configured to receive the projections 48 of the top ring 45 and permit axial movement of the plunger 26 with respect to the releaser member 52 but to resist or prevent rotational movement between the plunger 26 and the releaser member 52. As shown in the figures, although the channel surface 52 extends adjacent to the inner surface of the releaser member 52, the channel surface 52 does not have an arcuate shape and instead has a generally squared-off shape (as best illustrated in FIGS. 7B and 10A).

The releaser member 52 includes a channel surface 52b that extends proximally past the proximal-most (e.g., top) surface of the tubular body of the releaser member 52. For example, the releaser member 52 includes a proximally facing contact surface 52d for end-of-dose notification, which will be described in more detail below, and the channel surfaces 52b each extend past the contact surface 52 so as to provide a continuous path with respect for the top ring 45 while also permitting a sufficient gap between the proximally facing contact surface 52d and the corresponding surface involved in end-of-dose notification.

The releaser member 52 may be configured to rotate relative to the housing 12 and/or translate linearly relative to the housing 12, depending on the stage of operation of the drug delivery device 10. Initial rotation of the releaser member 52 associated with activation may be powered by the plunger biasing member 50 and/or the extender biasing member 35; whereas later rotation of the releaser member 52 associated with generation of the end-of-dose signal may be powered solely by the extender biasing member 35. Any linear translation of the releaser member 52 without rotation may be powered solely by the extender biasing member 35. In some embodiments, the releaser member 52 may translate linearly only in the proximal direction; however, alternative embodiments may permit linear translation of the releaser member 52 in both the proximal and distal directions.

Having described the general configuration of the drug delivery device 10, a method of using the drug delivery device 10 to perform an injection will now be described with reference to FIGS. 9A-12C. As a preliminary step, the user may remove the drug delivery device 10 from any secondary packaging, such as a plastic bag and/or cardboard box. Also, as a preliminary step, the user may prepare the injection site, e.g., by rubbing the patient's skin with an alcohol wipe. Next, the user may pull and detach the removable cap 19 from the front housing 25. As a result of this motion, the gripper 13 may pull and detach the sterile barrier 21 from the drug storage container 20. This may uncover the insertion end 28 of the delivery member 16. Nevertheless, the insertion end 28 of the delivery member 16 will remain surrounded by the guard member 32 at this stage because the guard member 32 is arranged in the extended position. Next, the user may position the drug delivery device 10 over the injection site and then push the distal end of the guard member 32 against the injection site. The force applied by the user will overcome the biasing force of the extender biasing member 35 and the biasing force of the lock ring biasing member 51, thereby causing the guard member 32 to retract into the opening 14 moving from the extended position to the retracted position in the proximal direction. The delivery member 16 remains stationary relative to the housing 12 during the retracting movement of the guard member 32.

Several of the device components include various features, surfaces, and openings for interacting with and controlling the release movement of the plunger 26 (e.g. the injection sequence). Generally, the injection sequence begins with retraction/axial movement of the guard member 32 in the proximal direction (upward in FIG. 2), which causes axial movement of the guard extension 37, which unlocks the releaser member 52. Once the releaser member 52 is unlocked (e.g. first stage of travel), the plunger 26 and the plunger biasing member 50 urge the releaser member 52 to rotate clockwise and permit axial movement of the plunger 26 (in the distal direction, downward in FIG. 2). The plunger then urges the stopper 24 in the distal direction, thereby urging the drug 22 from the drug product container 20 and out of the delivery member 16. Once the plunger has reached a certain point along the axial length of the device, movement of the releaser member 52 is further unlocked (e.g. second stage of travel) and the releaser travels in the proximal direction (upward in FIG. 2) and into contact with the plunger guide 60, thereby generating an end-of-dose indication (such as an audible click). The injection sequence will now be described in more detail.

The pre-injection stage is shown in FIGS. 2, 9A, 10, and 11A. Movement of the guard member 32 from the extended position to the retracted position may cause several actions to occur. Because the delivery member 16 remains stationary relative to the housing 12 during retraction of the guard member 32, the insertion end 28 of the delivery member 16 is caused to extend through an opening in the distal end of the guard member 32, thereby piercing the patients skin at the injection site and penetrating into the patient's subcutaneous tissue. In addition, retraction of the guard member 32 may also activate the drive mechanism 30 to expel the drug 22 from the drug storage container 20, as described below in more detail.

Figure 9A:
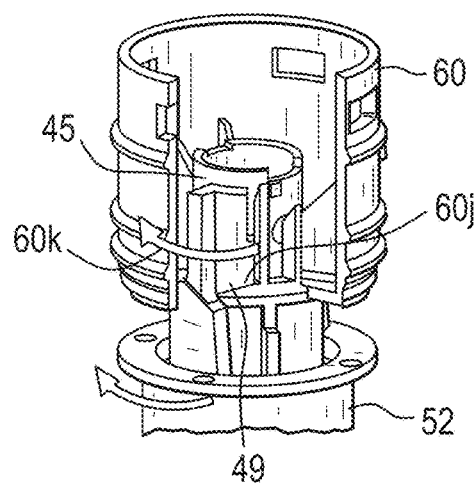
FIG. 9A is a perspective view of an exemplary plunger guide, an exemplary releaser member, and an exemplary plunger, wherein a portion of the guide member is shown in cut-away form for illustrative purposes, and wherein the drug delivery device is in a pre-injection position.

In the pre-delivery state prior to retraction of the needle guard 32, the plunger 26 and the releaser member 52 each may be arranged in a respective initial rotational position, as illustrated in FIGS. 9A, 10, and 11A. The plunger biasing member 50 may be in an energized state. As a consequence, the plunger biasing member 50 may exert a distally directed biasing force on the plunger 26 which urges the distally facing camming surface 49 against the proximally facing camming surface 60j. A resulting camming action may urge the plunger 26 to rotate in the clockwise direction. Despite these biasing force(s), neither the releaser member 52 nor the plunger 26 rotates in the pre-delivery state. This is because the releaser member 52 and the plunger are rotationally fixed in the pre-injection state. Accordingly, the releaser member 52, the plunger guide 60, the guard extension 37, and the housing 12 work in conjunction with one another to retain the plunger biasing member 50 in the energized state prior to retraction of the guard member 32, as is now described in more detail.

As best shown in FIG. 2, as the guard member 32 travels in the proximal direction (upward in FIG. 2), the proximal end 32d of the guard member 32 contacts a distally-facing surface of the guard extension 37 and urges the guard extension in the proximal direction. As shown in FIGS. 6B and 7A the inner surface of the guard extension 37 annular wall includes a locking flange 37c and the outer annular surface of the releaser member 52 a corresponding locking flange 52a. When the device is in the pre-injection stage, as shown in FIGS. 2, 9A, 10A, and 11A, the guard extension 37 locking flange 37c engages the releaser member 52 locking flange 52a, thereby rotationally locking the releaser member 52 (as best illustrated in FIG. 11A). At this point in the sequence, the distally facing camming surface 49 of top ring 45 of the plunger 26 is abutting against a proximally facing camming surface 60j of the plunger guide 60 such that the plunger 26 is restrained from axial travel due to this interaction (best illustrated in FIGS. 9A and 10A). The distally facing camming surface 49 and/or the proximally facing camming surface 60j includes a sloped surface to promote relative movement of the plunger 26 top ring 45 in the direction of arrow 60k in FIGS. 9A and 10A (clockwise). For example, the distally facing camming surface 49 has a slope 60m of approximately 10 degrees (best illustrates in FIGS. 9B and 9C) but may have any suitable slope such as 9 to 11 degrees, 8 to 12 degrees, 7 to 13 degrees, 6 to 14 degrees, 5 to 15 degrees, 4 to 16 degrees, or any other suitable slope. Additionally or alternatively, the distally facing camming surface 49 of top ring 45 may have a slope 49*a* of approximately 10 degrees but may have any suitable slope such as 9 to 11 degrees, 8 to 12 degrees, 7 to 13 degrees, 6 to 14 degrees, 5 to 15 degrees, 4 to 16 degrees, or any other suitable slope. The slope(s) on one or more of the respective surfaces 60*j*, 49 causes the axial force from the plunger biasing member 50 to generate a force in the transverse direction, thereby urging the plunger 26 top ring 45 in the clockwise direction 60*k*. However, as discussed above, the releaser member 52 resists or prevents rotational movement between the releaser member 52 and the plunger while the top ring 45 is positioned within and/or contacting the channel surface 52*b*. As a result, as long as the guard extension 37 is rotationally locking the releaser member 52 (as shown in FIGS. 2, 9A, 10A, and 11A), then the top ring 45 will remain rotationally locked by the channel surface 52*b* and axially locked by the proximally facing camming surface 60*j*.

The unlocking stage is shown in FIG. 11B, where the guard extension 37 translates in the proximal direction until the guard extension 37 locking flange 37*c* no longer engages the releaser member 52 locking flange 52*a* and the releaser is no longer rotationally locked. At this stage in the injection sequence, two things happen simultaneously or near simultaneously: (1) the guard biasing member 35 urges the releaser member 52 in the clockwise direction (shown in FIG. 9B) and upward due to a camming surface on one or both of the inner surface of the releaser member 52 (generally aligned with numeral 52*c* labeled in FIGS. 9C and 7B, but on the inner surface of the releaser member 52 rather than the outer surface as indicated by 52*c*) or the outer surface of the plunger guide 60 (such as rib 60*n*, FIG. 5B) that translates the axial force from the guard biasing member 35 into a transverse (clockwise) force and causes the releaser member 52 to rotate clockwise and move upward (proximally) and (2) the plunger biasing member 50 urges the top ring 45 in the clockwise direction and downward (distally) due to the camming action between surfaces 49, 60*j* of the plunger 26 and the plunger guide 60 thereby causing the plunger 26 to move clockwise and slightly downward along ramped surface 60*j*. In other words, the releaser member 52 and the plunger 26 top ring 45 are both rotating clockwise at the same time or substantially the same time, due to forces from respective biasing members 35, 50. This sliding motion between surfaces 49, 60*j* of the plunger 26 and the plunger guide 60 results in rotation, as well as linear translation (not unlike a spiral pathway). Accordingly, the plunger guide 60 may function as a cam and the plunger rod 26 the cam follower.

Figure 9B:
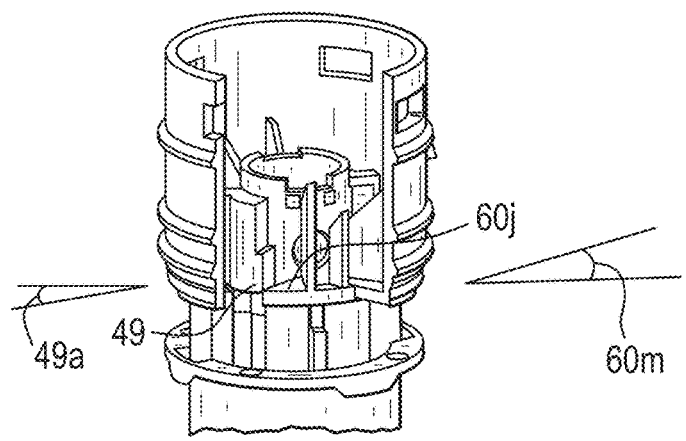
FIG. 9B is a perspective view of the components from FIG. 9A, wherein the plunger is in a released position before axial travel by the plunger.
Figure 10B:
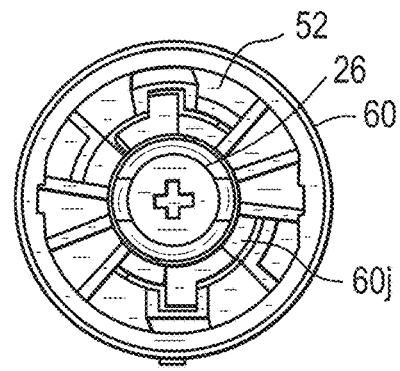
FIG. 10B is a top view of the components in FIG. 9B, wherein the plunger is in the released position before axial travel by the plunger.

The unlocked stage is shown in FIGS. 9B, 10B, and 11C. In this stage, the distally facing camming surface 49 of the top ring 45 has cleared the proximally facing camming surface 60*j* of the plunger guide 60 such that the top ring 45 (and thus the plunger 26) is no longer axially restrained by the plunger guide 60. As a result, the plunger biasing member 50 urges the plunger 26 axially in the distal direction.

Figure 9C:
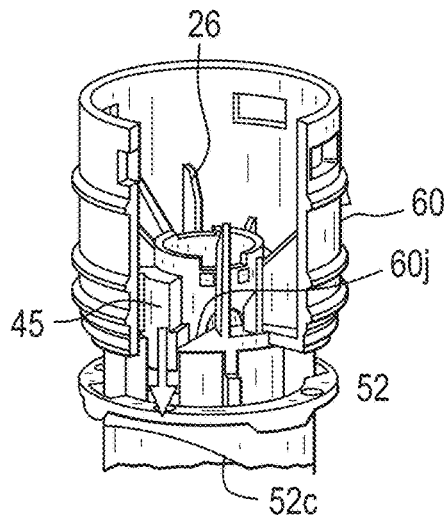
FIG. 9C is a perspective view of the components from FIG. 9A, wherein the plunger is in the released position after the start of axial travel by the plunger.
Figure 10C:
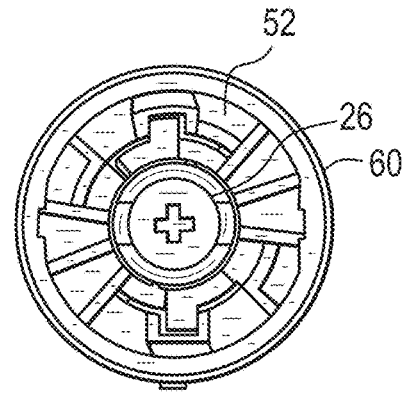
FIG. 10C is a top view of the components in FIG. 9C, wherein the plunger is in the released position after the start of axial travel by the plunger.
Figure 12A:
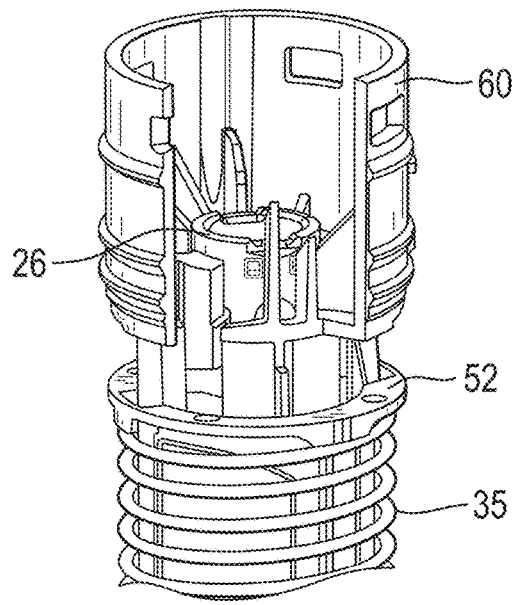
FIG. 12A is a perspective view of the components in FIG. 9A, plus an exemplary guard biasing member, where the plunger is in the released position after the start of axial travel by the plunger, where some of the components are shown in cut-away form for illustrative purposes.

The downward stroke stage is shown in FIGS. 9C, 10C, and 12A. At this point in FIGS. 9C, 10C, and 12A, the top ring 45 is still visible near the proximal portion of the plunger guide 60, but it will quickly travel along a longitudinal slot 86 formed in the plunger guide 60 and the channel surface 52*b*. During this stage, the plunger 26 top ring 45 is traveling along both the channel surface 52*b* of the releaser member 52 and the longitudinal slot 86 of the plunger guide 60, thereby preventing rotation between any of the three components (26, 52, 60). As a more specific example, because the plunger guide 60 is rotationally fixed with respect to the housing 12, while the top ring 45 is positioned within both the channel surface 52*b* and the longitudinal slot 86, the releaser member 52 is unable to rotate. Also during this stage, as the plunger 26 travels distally, the gap 18 between the base 47 of the plunger 26 and the stopper 24 shrinks and the base 47 contacts the stopper 24. The device 10 is designed such that plunger 26 is traveling with a force sufficient to drive the stopper 24 in the distal direction and urge the drug 22 from the delivery member 16. At the same time, the device 10 is also designed such as to reduce or eliminate the likelihood of glass breakage, undesirable forces acting on the patient, and/or undesirable impact vibration or sound due to interaction between the base 47 and the stopper 24. For example, the plunger biasing member 50 design parameters may be designed to meet these two sets of design goals. As another example, a damping component may be positioned between the base 47 and the stopper 24 or in another location in the device 10 to dampen the forces between the base 47 and the stopper 24. For example, the base 47 may include an elastomeric component, section, or other damping feature. Additionally or alternatively, the stopper 24 may be formed of an elastomeric material that includes inherent damping properties. Additionally or alternatively, the stopper 24 may include an additional elastomeric component, section, or other damping feature.

In some embodiments, the camming action between the distally facing camming surface 49 on the projection 48 and the proximally facing camming surface 60*j* of the plunger guide 60 may provide a damping effect. More particularly, a sliding friction between these two surfaces may be selected to slow initial expansion of the plunger biasing member 50. As a consequence, the velocity of the plunger 26 may be reduced during the initial expansion of the plunger biasing member 50, as compared to free uninhibited expansion of the plunger biasing member 50. The reduced velocity of the plunger 26 may cause the plunger 26 to strike the stopper 24 with less force, which reduces the chances of structural damage to the drug storage container 20 and/or facilitates a more comfortable injection for the user.

Figure 12B:
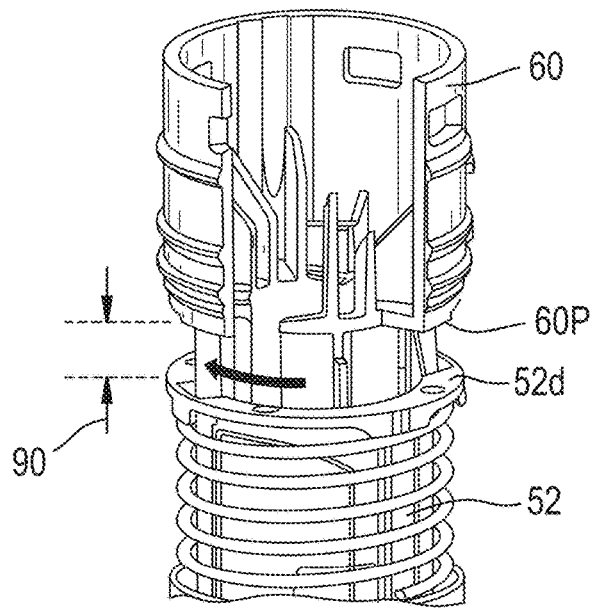
FIG. 12B is a perspective view of the components of FIG. 12A, plus a more distal view of the device, where the plunger is at or near an end-of-dose release position but the releaser member is not yet at an end-of-dose position, and where the guard extension member and the guard biasing member are removed for illustrative purposes.
Figure 12C:
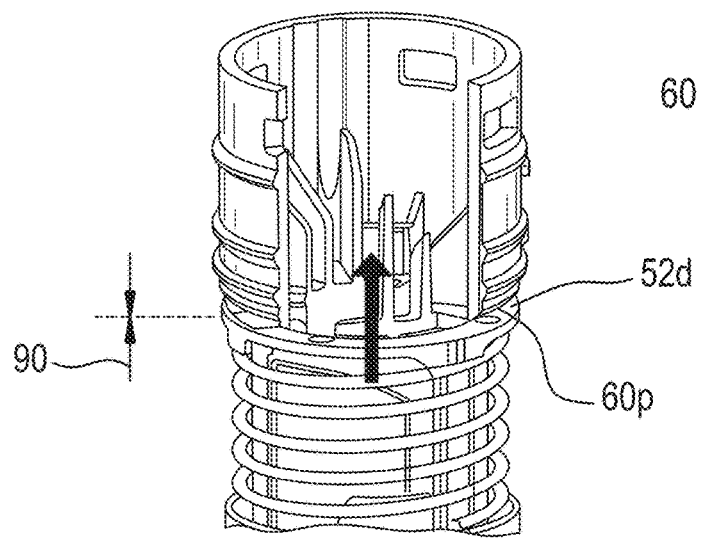
FIG. 12C is a perspective view of the components of FIG. 12A, where the releaser member is at the end-of-dose position.

The end-of-dose stage is shown in FIGS. 12B and 12C. As discussed above, during the downward stroke stage, while the top ring 45 is positioned within the channel surface 52*b* and the longitudinal slot 86, the releaser member 52 is unable to rotate with respect to the plunger guide 60. However, in the end-of-dose initiation stage shown in FIG. 12B, the top ring 45 in some embodiments may clear the distal end of the releaser member 52 and no longer restricts or prevents rotation of the releaser member 52. As a more specific example, as shown in the bottom portion of FIG. 12B, as the top ring 45 exits the channel surface 52*b* and/or a distal surface 52*d* of the releaser, the releaser member 52 is no longer rotationally constrained by the top ring 45 and the releaser member 52 is urged upward by the guard biasing member 35. As a result of the upward force of the guard biasing member 35 and camming surfaces, the releaser member 52 rotates clockwise while it moves upward in a spiral like path and a proximal facing surface 52*d* of the releaser member 52 contacts a distal facing surface 60*p* of the plunger guide 60, thereby making an audible click sound. As a more specific example, FIG. 12B shows a gap 90 between the respective surfaces 52*d*, 60*p*, but that gap 90 is then eliminated when the releaser member 52 travels proximally, as shown in FIG. 12C. The length of the channel surface 52*b* and plunger 26 may be designed so that the top ring 45 exits the channel surface 52b as the stopper 24 reaches a desired point of travel within the drug storage container 20, such as its end of travel near the distal end of the drug storage container 20.

As a more specific example of the camming surface arrangement between the releaser member 52 and the plunger guide 60, and as discussed above, the rib 60n of the plunger guide 60 is aligned with the inner surface of the releaser member 52 that is indicated by 52c in FIG. 7A and in FIG. 7B (but on the inner surface rather than the outer surface as indicated by 52c). The rib 60n has a sloped surface to help facilitate and/or promote relative rotation between the components 52, 60. More specifically, the urging force of the guard biasing member 35, combined with the sloped surface of the rib 60n, creates a rotational force (e.g., torque) and causes the releaser member 52 to rotate with respect to the plunger guide 60. During the first stage of releaser member 52 rotation (e.g., the unlocking stage shown in FIG. 11B), the rib 60n travels along a first section of the inner camming surface 52c of the releaser member 52, such as the first section 52f shown in FIG. 7B. During the second stage of releaser member 52 rotation (e.g., the end-of-dose stage shown in FIGS. 12B and 12C), the rib 60n travels along a second section of the inner camming surface 52c of the releaser member 52 such as the second section 52g shown in FIG. 7B. As is visible in FIG. 7B, the second section 52g includes a pocket 52h that is able to receive the rib 60n and permit the releaser member 52 to quickly move proximally towards the plunger guide 60 and cause the end-of-dose audible click. In summary, during the end-of-dose stage, the top ring 45 clears the channel surface 52b of the releaser member 52 and the guard biasing member 35 and the rib 60n cause the releaser member 52 to rotate and move upwards, ending with a quick upward (proximal) movement of the releaser member 52 into contact with the plunger guide 60 as the rib 60n moves into the pocket 52h.

Once the patient and/or health care provider hears the audible sound, he/she/they may be notified that the dose is complete. In some embodiments, the user may be informed of the significance of the audible signal by way of instructions provided with the drug delivery device 10. In some embodiments, these instructions may take the form of an Instructions for Use (IFU) pamphlet packaged together with the drug delivery device 10. In some embodiments, the user may obtain additional confirmation that drug delivery is complete by watching movement of the stopper 24 and/or plunger 26 through the window 17. In some embodiments, the audible signal may be accompanied by a vibration or other tactile feedback produced as a result of the releaser member 52 striking the plunger guide 60. The audible notification may be in the form of a click or slap sound, or any other suitable audible signal that is perceptible to the user. The audible signal may be generated simultaneously, or substantially simultaneously, with the stopper 24 reaching the end-of-dose position.

As described above, in addition to its retaining function, the releaser member 52 may also be used to generate an audible signal indicating to the user that drug delivery or dosing is complete. This dual-function role may reduce part quantity and/or design complexity. Alternatively, the releaser member 52 does not need to have this indicator function. In alternative embodiments, the indicator may be defined by a structure that is separate from but rigidly attached to the releaser member 52.

While the foregoing descriptions may utilize the extender biasing member 35 to provide the actuation energy needed generating the end-of-dose signal, alternative embodiments may utilize a biasing member that is separate from extender biasing member 35 for this purpose. In certain such embodiments, this additional biasing member may have a distal end fixed relative to the housing 12 and a proximal end abutting against a distally facing surface of the releaser member 52. As such, the biasing member may push off of the housing 12 to exert a biasing force in the proximal direction against the releaser member 52. Furthermore, this biasing member may operate independently of the plunger biasing member 50 and the extender biasing member 35.

In any case, once the user receives some assurance that drug delivery is complete, the user may then lift the drug delivery deice 10 off of the injection site. With nothing to resist it, the extender biasing member 35 may push the guard member 32 from the retracted position to the extended position to cover the insertion end 28 of the delivery member 16. In some embodiments, this movement of the guard member 32 may cause the lock ring 40 to rotate to a position where it prevents subsequent retraction of the guard member 32.

For example, as discussed above, in some embodiments of the drug delivery device 10 may include a lock ring 40 configured to lock the guard member 32 in the extended position once the guard member 32 has moved from the retracted position to the extended position In the present embodiment, the lock ring 40 is centered and rotates about the longitudinal axis A. As illustrated in FIG. 2, a proximal end of the lock ring 40 may be in contact with the a portion of the housing 12 and the distal end of the lock ring 40 may be disposed at least partially within the guard member 32. The lock ring biasing member 51 may be positioned in the axial direction between a distally facing surface of the lock ring 40 and a proximally facing surface of the guard member 32. The lock ring biasing member 51 may initially be in a compressed or energized state such that it biases the lock ring 40 and the guard member 32 away from each other. As such, the lock ring biasing member 51 may exert a biasing force urging the guard member 32 toward the extended position, as well as exert a biasing force urging the proximal end of the lock ring 40 against a portion of the housing 12, such as the annular collar 12d. In some embodiments, the lock ring biasing member 51 may include a compression spring (e.g., a helical compression spring).

The lock ring 40 may also serve to provide an initial resistance to movement of the guard member 32. As discussed above, the device 10 may be inserted into the patient by utilizing, harness, or otherwise taking advantage of inertial forces. The lock ring 40 and/or other components may provide an initial resistance to movement of the guard member 32 to build-up the user inputted force, as is discussed in more detail below.

Figure 13:
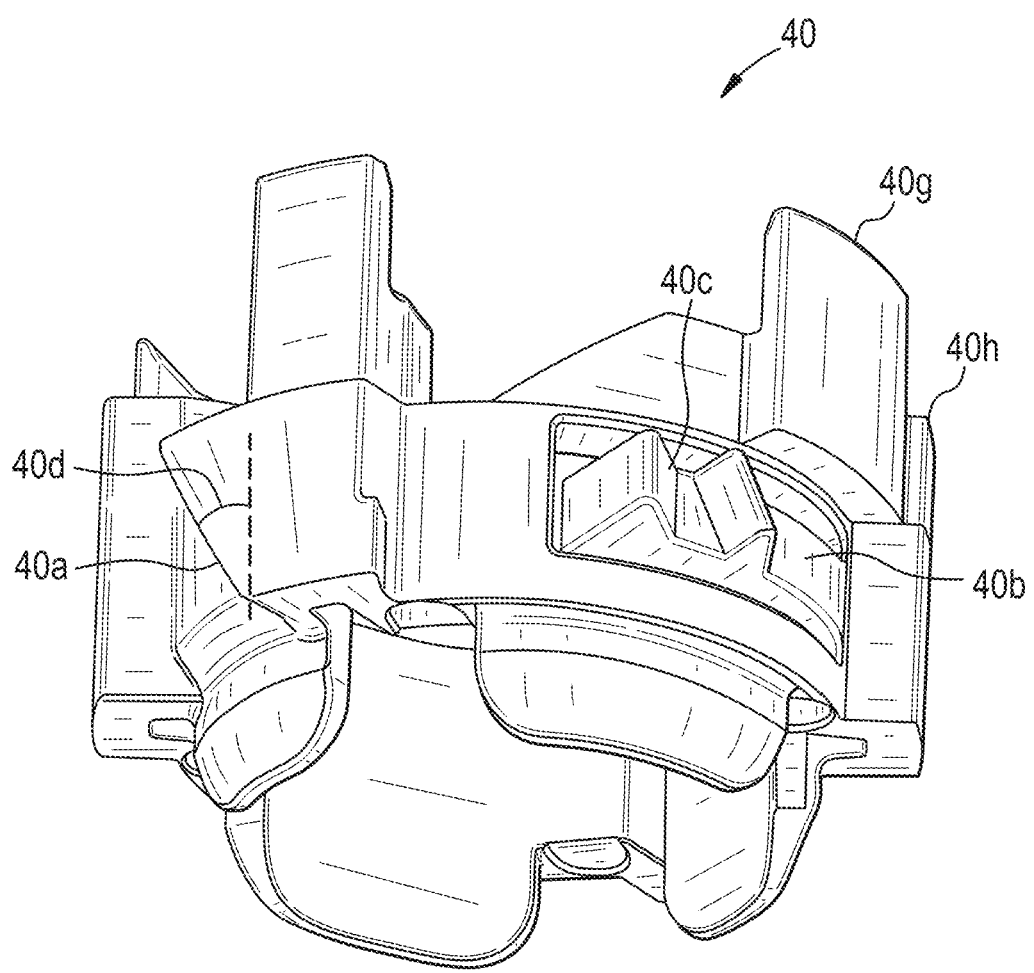
FIG. 13 is a perspective view of an exemplary lock ring in accordance with various embodiments.

FIG. 13 shows a perspective view of the lock ring 40. In the example shown in FIG. 13, the lock ring 40 includes a camming surface 40a that is non-parallel to the axis A and configured to convert translational movement of the shield guard 32 into rotational movement of the lock ring 40. As a more specific example, the camming surface 40a shown in FIG. 13 is at an angle 40d to the axis A of approximately −30 degrees. Any suitable angle may be utilized, such as −10 to −80 degrees, −20 to −70 degrees, −20 to −60 degrees, −20 to −50 degrees, −20 to −40 degrees, −25 to −35 degrees, or any other suitable angle. The angle 40d may be a positive number as well (such that the angled surface is flipped around the axis A), but such as configuration would cause the lock ring 40 to rotate in the opposite direction. In such a case, any suitable angle may be utilized, such as 10 to 80 degrees, 20 to 70 degrees, 20 to 60 degrees, 20 to 50 degrees, 20 to 40 degrees, 25 to 35 degrees, or any other suitable angle.

In the example shown in FIG. 13, the lock ring 40 includes a locking arm 40b that may be a generally cantilevered arm extending (along a circumference of the lock ring 40) from a body portion of the lock ring 40. The locking arm 40b may include a ridge 40c extending transversely to the body portion of the lock ring 40 (i.e. outwardly and non-parallel to the axis A).

Figure 14:
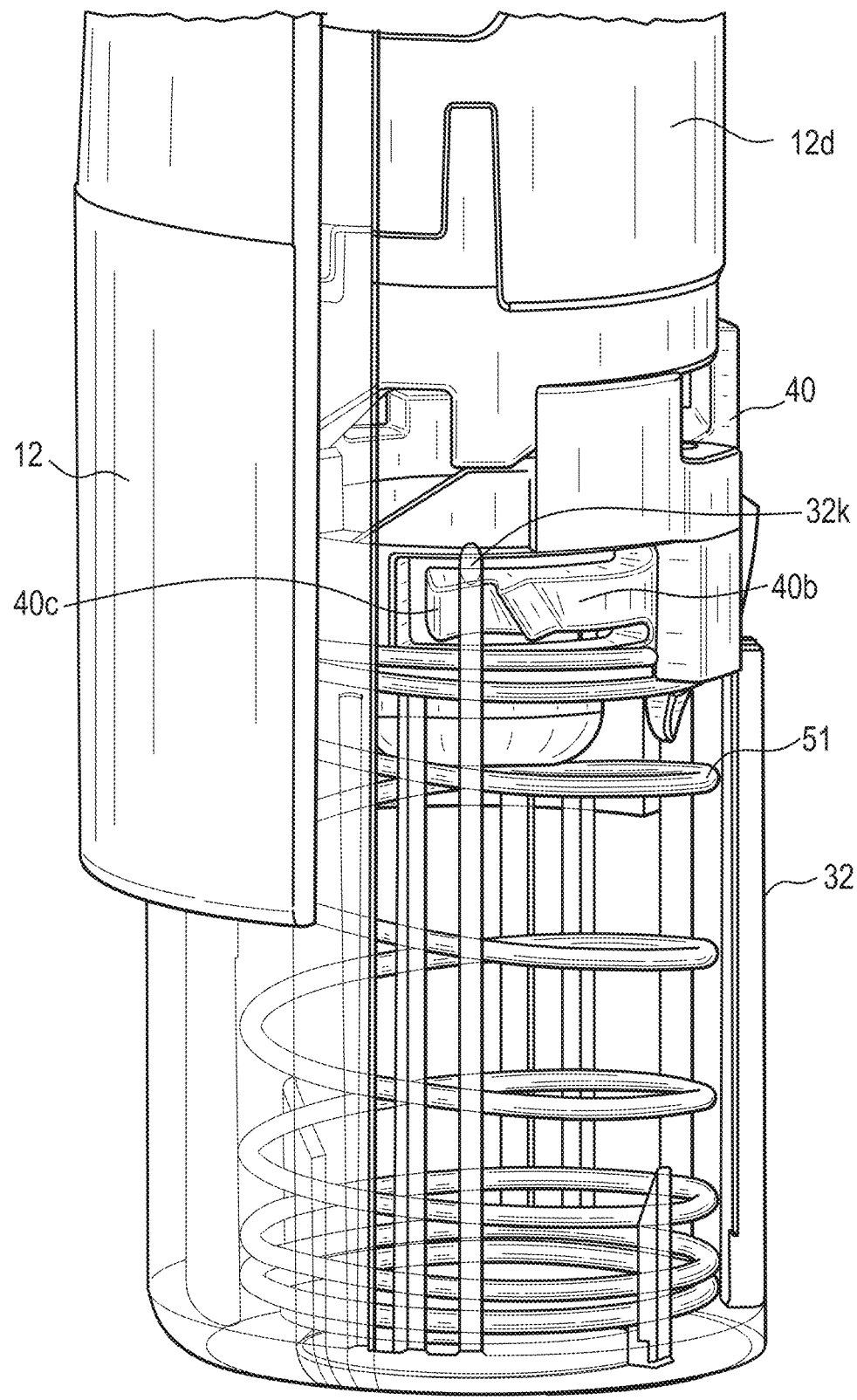
FIG. 14 is a perspective view of a distal portion of an exemplary device in accordance with various embodiments when a guard member is in a pre-injection, pre-deflection state, and wherein portions of the housing are shown in cut-away form for illustrative purposes.

FIG. 14 shows the lock ring 40 along with other various components of the device in a pre-deflection stage (e.g., before the guard member 32 has deflected axially in the proximal direction). For example, FIG. 14 shows a distal portion of the housing 12 that is in partial cross-sectional view for illustrative purposes, the guard member 32 in translucent form and partially cut-away for illustrative purposes, the lock ring 40, and a portion of the housing inner collar 12d. The guard member 32 includes a plurality of ribs formed on the annular inner surface thereof. These ribs are shown in FIG. 14, but portions of the annular surface itself have been cut away for illustrative purposes. Similarly, although portions of the housing 12 have been cut away for illustrative purposes, the annular collar 12d formed on the inner surface of the housing 12 is visible in FIG. 14. When the device 10 is in the pre-deflection stage (as shown in FIG. 14), the ridge 40c is adjacent to an inertial rib 32k formed on the inner annular surface of the guard member 32. As a more specific example, when the device 10 is in the pre-deflection stage, the ridge 40c is disposed to the left of the inertial rib 32k such that the lock ring 40 generally resists rotation (and thereby resists axial deflection of the guard member 32) until the ridge 40c is able to move past the inertial rib 32k (i.e. to clear the inertial rib 32k). This arrangement is discussed in more detail below.

FIGS. 15A and 15B show views from different angles (approximately a 90 degrees apart from each other) when the device is in the initial deflection stage just after the guard member 32 has been released from engagement with the locking arm 40b. As a more specific example, the lock ring 40 has rotated such that the ridge 40c has just cleared locking rib 32k, thereby allowing the guard member 32 to more freely deflect (in the proximal direction). At this point in the sequence, the injection sequence likely has not been activated. For example, the plunger biasing member 50 likely has not yet been released, as the housing 12 has not yet traveled distally enough for the delivery member 16 to pierce the user's tissue.

In order for the components of the device to move from the stage shown in FIG. 14 to the stage shown in FIGS. 15A and 15B, two main events have occurred generally simultaneously with each other: initial rotation of the lock ring 40 and release from the locking arm 40b. With respect to the initial rotation, as shown in FIG. 15B, the lock ring camming surface 40a is generally aligned with camming rib 32j to convert translational movement of the shield guard 32 into rotational movement of the lock ring 40. As a more specific example, as the shield guard is retracted the proximally facing top surface of the camming rib 32j applies an axial upward force on the camming surface 40a. As a more specific example, the angle of the camming surface 40a with respect to the axis A causes the upward force from the camming rib 32j to have an axial component (along axis A) as well as a rotational component (transverse to axis A), thereby rotating the lock ring 40. In other words, in both the stage shown in FIG. 14 and the stage shown in FIGS. 15A and 15B, deflection (retraction) of the guard member 32 causes rotation of the lock ring 40. At the same time that camming rib 32j is urging the lock ring 40 to rotate to the right (i.e. counter-clockwise when viewed from the top of FIG. 15B), the locking arm 40b may be generally resisting such movement. For example, when the guard member 32 is depressed, it moves from the position shown in FIG. 14 to the position shown in FIGS. 15A and 15B. As a more specific example, when the device 10 is in position shown in FIG. 14, the ridge 40c is disposed to the left of the inertial rib 32k such that the lock ring 40 is unable to rotate past a certain point until the ridge 40c is able to clear the inertial rib 32k. The ridge 40c may be able to clear the inertial rib 32k via radially inward deflection of the locking arm 40b, as is shown in FIG. 15A. In such a design, the flex of the locking arm 40b at least partially determines the force required for the ridge 40c to clear the inertial rib 32k. In other words, the flex of the locking arm 40b at least partially determines the force required to deflect the guard member 32 sufficiently to activate the injection process. The angle of the ridge 40c with respect to the circumference of the lock ring 40 may also, in part, determine the force required to deflect the guard member 32 sufficiently to activate the injection process. Additionally, the degree of rotation that the lock ring 40 must undergo for the ridge 40c to clear the inertial rib 32k at least partially determines the distance that the guard member 32 will translate (axially) before the locking arm 40b "releases" the guard member 32.

During operation, when the patient presses the distal end of the guard member 32 against the patient's skin at the injection site, the delivery device 10 housing 12 may advance toward the injection site by a relatively small distance (e.g. 2-4 mm). The patient may then feel resistance between the inertial rib 32k and the ridge 40c. As the patient presses down with more force, the ridge 40c will clear the inertial rib 32k and the delivery device 10 will achieve a quick release to harness the energy stored in the patient's muscles while compressing the needle cover and its spring to a defined release point. The release mechanism, such as the above-described flex of the locking arm 40b, the degree of rotation required to clear the inertial rib 32, and other parameters, may be designed such that when the ridge 40c clears the inertial rib 32k, the resulting needle insertion speed exceeds the patient's reaction speed, and the combination of this speed and the device's mass cause the needle to quickly and fully penetrate the skin to the subcutaneous depth. In other words, once the guard member 32 reaches the position shown in FIGS. 15A and 15B, the resistance to depressing the guard member drops significantly so that the needle is inserted before the patient is able to halt the insertion process. As a more specific example, at this stage in the insertion process, the primary resistance to deflection of the guard member 32 that is attributable to the components in the distal portion of the device is from the lock ring biasing member 51, but that resistance is significantly lower than that provided by the locking arm 40b. Also, of note, the user may still feel resistance against deflection of the guard member 32 that is attributable to other subcomponents in the device, such as activation of the drive mechanism 30. Even though the insertion process occurs very quickly from this point forward, the subsequent stages will be examined in detail in the figures and the below text.

Figure 16A:
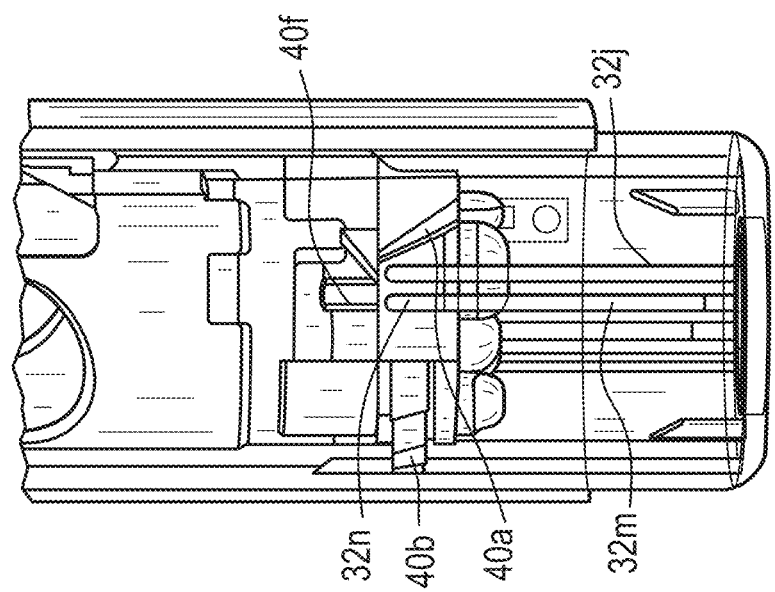
FIG. 16A is a perspective view of the distal portion of the device shown in FIG. 14, where the guard member further deflected distally from the stage shown in FIG. 15A.
Figure 16B:
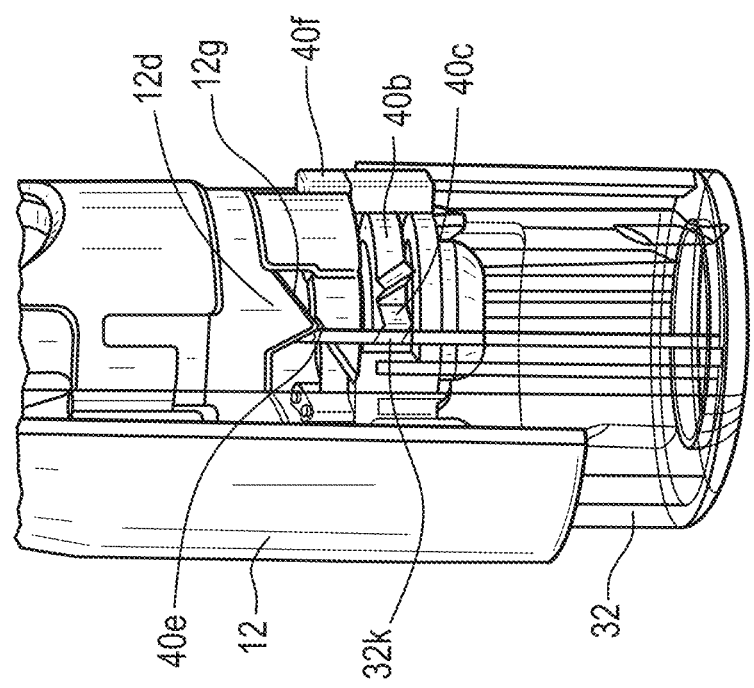
FIG. 16B is a perspective view of the same device and the same stage as FIG. 16A, from a view that is approximately 90 degrees from that shown in FIG. 16A.

FIGS. 16A and 16B show views from different angles (approximately a 90 degrees apart from each other) when the device is in the continued downward travel stage (a later point in time than FIGS. 15A and 15B, where the housing has moved further in the distal direction and the guard member 32 has been further retracted). At the point in the sequence shown in FIGS. 16A and 16B, the injection sequence may or may not have begun, depending on the desired release parameters such as needle length, desired insertion depth, distance between the guard member 32 and the tip of the needle.

Figure 25:
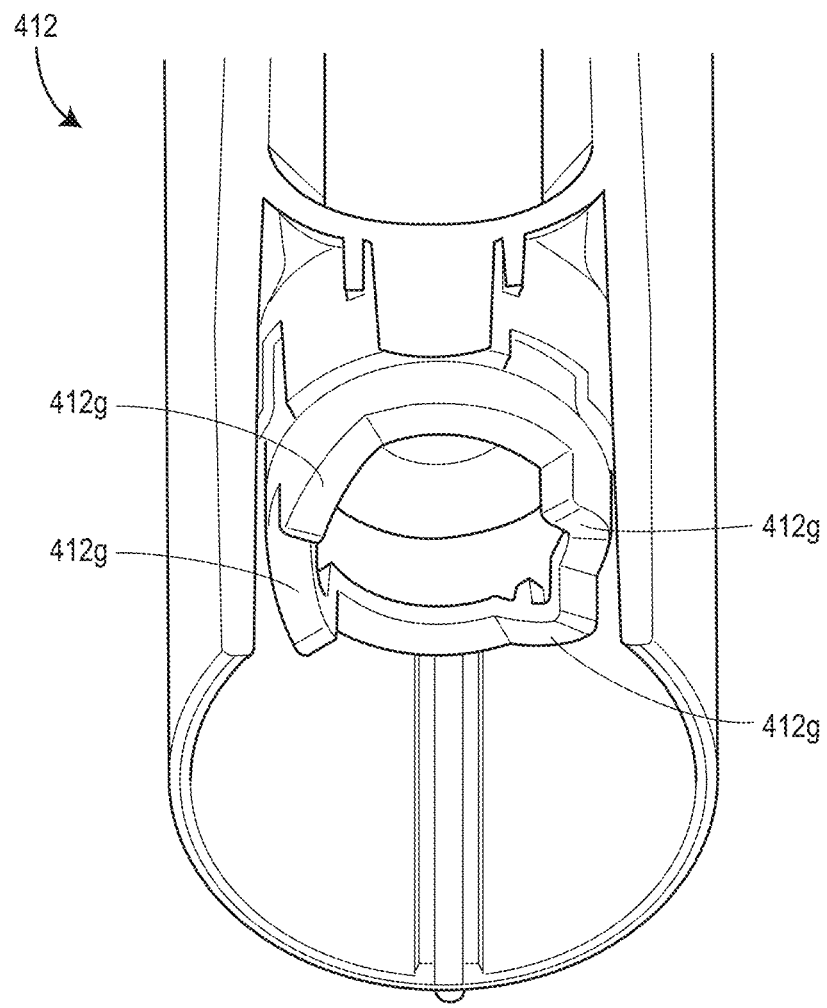
FIG. 25 illustrates a perspective view of an exemplary housing in accordance with various embodiments.

As shown in FIG. 16A, at this point in the sequence, the camming rib 32*j* of the guard member 32 clears or is about to clear the camming surface 40*a* so that the guard member 32 is able to deflect without rotating the lock ring 40. Additionally or alternatively, a ramped surface 40*e* of the lock ring 40 may engage a ramped surface 12*g* of the housing 12 (that may be defined by the annular collar 12*d*, similar or the same as the ramped surface 412*g* in FIG. 25); this interaction between the respective surfaces 40*e*, 12*g* may also promote rotation of the lock ring 40 until it reaches the point shown in FIGS. 16A and 16B. Additionally or alternatively, at this stage of the insertion, a stop ridge 40*f* of the lock ring 40 engages a stop rib 32*n* and limits rotation of the lock ring 40. However, as discussed above, at this stage the guard member 32 is able to deflect without requiring or causing further rotation of the lock ring 40. More specifically, as shown in FIGS. 16B and 17, the adjacent ribs (the stop rib 32*n* and the camming rib 32*j*) extend between the adjacent components of the lock ring 40 (the stop ridge 40*f* and the camming surface 40*a*) so that the guard member 32 is able to deflect with respect to the housing 12.

Figure 17:
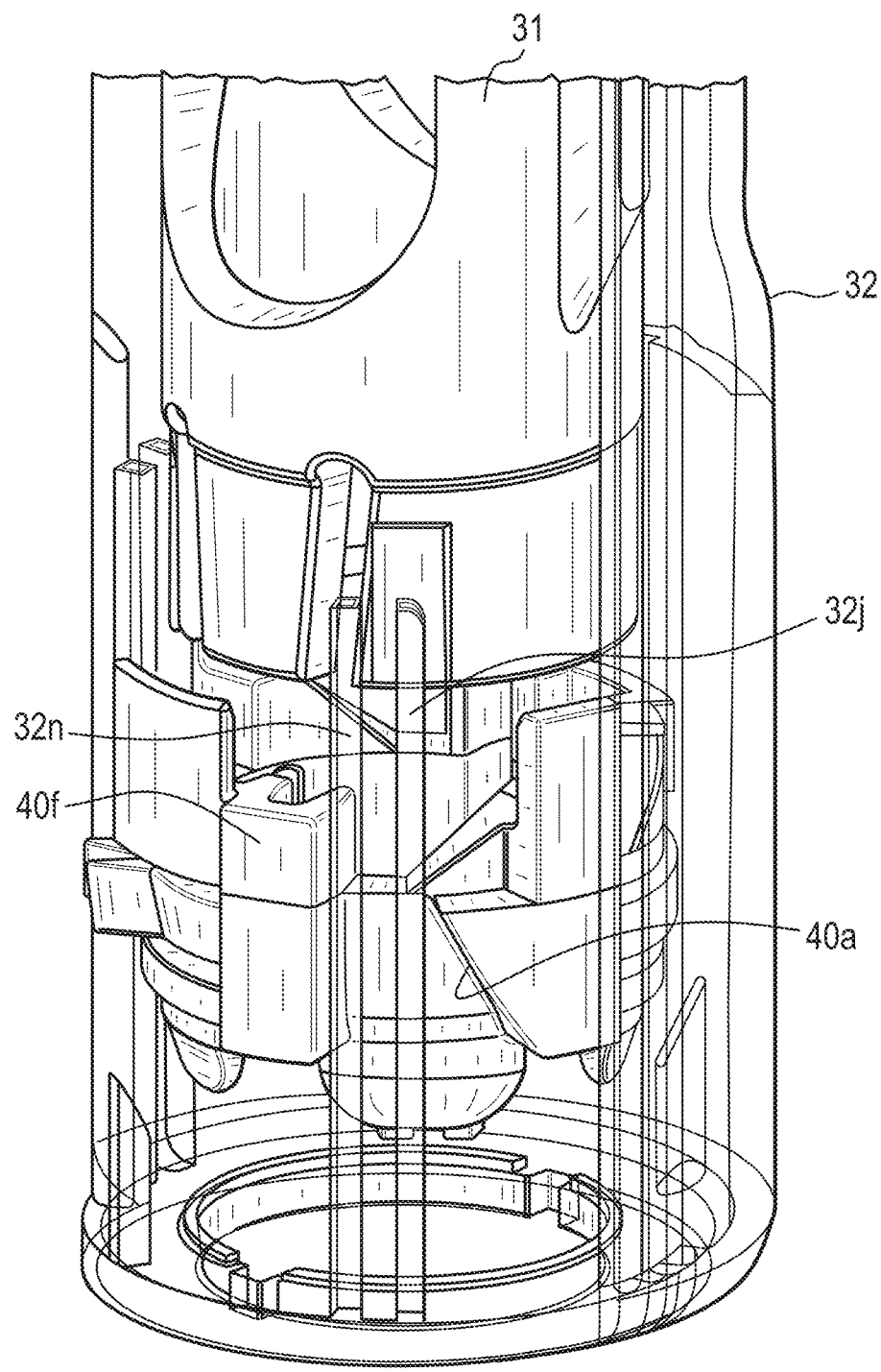
FIG. 17 is a perspective view of the distal portion of the device shown in FIG. 14, where the guard member is in a fully-deflected or near fully-deflected position with respect to the housing, such as during an injection stage.

FIG. 17 shows a view when the device is in the final insertion stage, when the guard member is fully or nearly fully retracted. At this point in the sequence, the injection sequence likely has been activated. For example, the plunger biasing member 50 likely has been released and the delivery member 16 has been inserted into the user's tissue. Additionally, at this point in the sequence, the guard member 32 is at or near its fully retracted position with respect to the housing 12 and the device 10 is still being held against the patients skin. The user will preferably hold the device 10 in this position until at least the time when the drug delivery process is complete (i.e., when the full dose of the drug 22 has been delivered to the patient) and the end-of-dose notification indicates that the dose is complete. Of note, for illustrative purposed, the guard member 32 shown in FIG. 17 has portions cut-away and FIG. 17 does not show the housing 12 (including the annular collar) or the drug storage container 20.

FIGS. 18A and 18B shows the device 10 in a locked-out configuration, when the guard member 32 is in the fully extended position (FIG. 18A) or near-fully extended position (FIG. 18B). As a more specific example, the stop rib 32*n* and the camming rib 32*j* of the guard member 32 are aligned with the stop ridge 40*f* to limit and/or prevent deflection of the guard member 32 in the proximal direction. As another more specific example, the guard member 32 is only able to travel in the proximal direction by the distance shown by gap 91 in FIG. 18A so that the guard member 32 is unable to be moved axially in the proximal direction by a distance sufficient to expose the delivery member 16. In other words, the guard member 32 is locked in a guarded position annularly surrounding the needle and minimizing or preventing inadvertent needle sticks.

In some embodiments, prior to removal of the removable cap 19, the gripper 13 may be configured to prevent deflection of the locking arm 40*b*. As an example, an outer surface of the gripper 13 may be configured to abut against an inner surface of the locking arm 40*b* to prevent radially inward deflection of the locking arm 40*b* prior to removal of the removable cap 19. This configuration may reduce the possibility of unintended lockout caused by vibrations or sudden movements during transport or storage of the drug delivery device 10 prior to use. When the removable cap 19 with the gripper 13 is removed, the locking arm 40*b* may be allowed to deflect in the manner described above.

The lock ring 40 and the housing 12 have respective stop surfaces that abut each other and prevent rotation therebetween. For example, the lock ring 40 may have stop surfaces 40*g* and 40*h* (FIGS. 18A, 13) that abut stop surfaces 12*j*, 12*k* (FIG. 18A) of the annular collar 12*d*. The respective stop surfaces 40*g*, 40*h* of the lock ring 40 and the respective stop surfaces 12*j*, 12*k* of the annular collar 12*d* may be stepped surfaces to prevent or resist rotation between the lock ring 40 and the housing 12. The lock ring biasing member 51 may urge the lock ring 40 in the proximal direction and/or the guard member 32 in the distal direction to retain the lock ring 40 in place as shown in FIGS. 18A and 18B, namely abutting the annular collar 12*d*.

The circular cross-section of the housing 12 may make it prone to rolling across a surface when placed on its side. To inhibit or prevent such rolling, a portion or the entirety of the removable cap 19 may have a non-circular cross-section. In the embodiment illustrated in the figures, the removable cap 19 has a distal end with a non-circular cross-section and a proximal end with a circular cross-section. As such, the cross-section of the removable cap 19 gradually transitions from a circular cross-section to a non-circular cross-section when moving from the proximal end of the removable cap 19 to the distal end of the removable cap 19. In the illustrated embodiment, the non-circular cross-section of the distal end of the removable cap 19 generally takes the form of a square. In other embodiments, the non-circular cross-section may be rectangular, triangular, or any other polygonal or partially polygonal shape, so long one or more sides removable cap 19 are flat or substantially flat to inhibit or prevent rolling. Furthermore, the non-circular cross-section of the distal end of the removable cap 19 may gradually increase in size moving in the distal direction, such that the distal-most portion of the distal end of the removable cap 19 has a larger cross-sectional area than a proximal-most portion of the distal end of the removable cap 19. This configuration gives the distal end of the removable cap 19 a flared shape, which, in turn, may help a user grip and pull the removable cap 19 off of the housing 12.

In some embodiments, the housing 12 and the removable cap 19 may each include a respective anti-rotation feature. These anti-rotation features may engage each other to prevent or inhibit the removable cap 19 from rotating relative to the housing 12 when the removable cap 19 is in a storage position. In some embodiments, the anti-rotation feature of the housing 12 may be adjacent to and generally in-line with the anti-rotation feature of the removable cap 19 when the removable cap 19 is in the storage position. For example, a radial protrusion 9 shown in FIG. 1A is positioned adjacent to the distal end of the housing 112. As shown in FIG. 1B, the removable cap 19 includes an opening 8 may be sized to matingly receive the radial protrusion 9 when the removable cap 19 is in the storage position. As a consequence of this mating engagement, the removable cap 19 may be unable to rotate relative to the housing 12. This may be beneficial if a user attempts to twist the removable cap 19 when pulling the removable cap 19 off of the housing 12. In certain cases, rotation of the removable cap 19 may cause a sterile barrier such as an RNS or FNS to rotate, which, in turn, may cause a tip of a needle to core into a seal member within the RNS or FNS. Thus, having the radial protrusion 9 disposed within the opening 8 at least during the initial moments of cap removal may prevent coring of the needle. In alternative embodiments, the opening 8 may be formed in the wall of the housing 12 and the radial protrusion 9 may extend in the proximal direction from a proximal end of the removable cap 19.

In other embodiments, the removable cap may be permitted and/or intended to rotate with respect to the housing. For example, the removable cap may include feature(s) that translate rotational movement of the removable cap into an axial assist force that helps urge the cap away from the housing. As a more specific example, the removable cap and/or the housing may have a camming surface, such as a wave-shaped surface, that converts rotational movement of the removable cap with respect to the housing into distal axial movement of the removable cap with respect to the housing. The axial assist force provided by such an arrangement may benefit various users including those having limited dexterity and/or strength due to, for example, an illness.

Figure 19A:
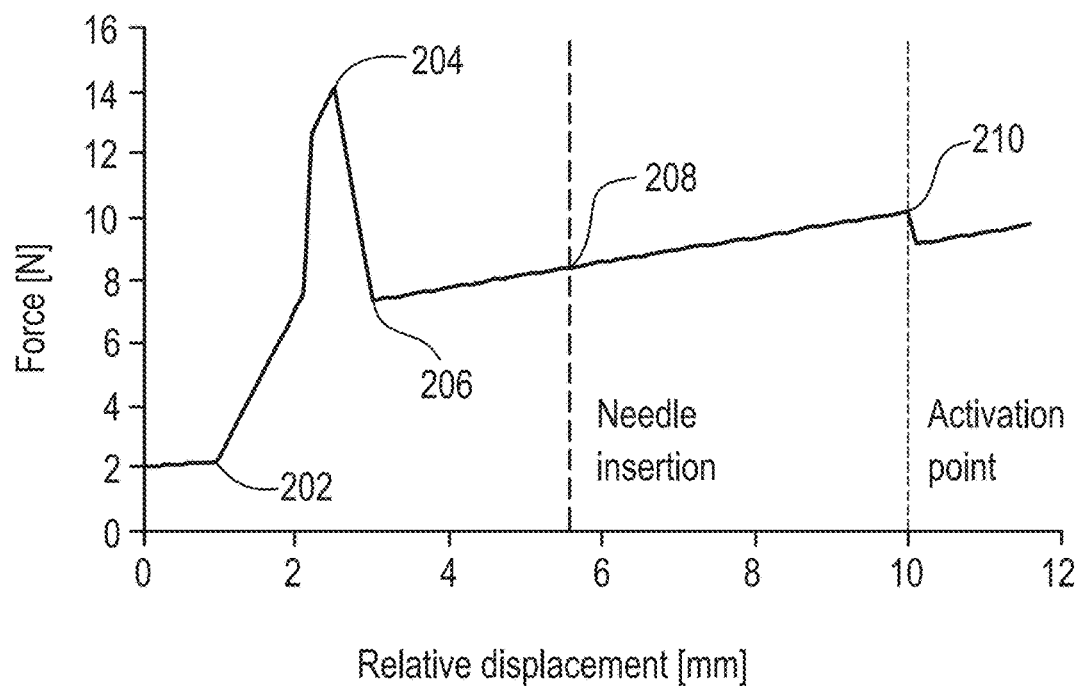
FIG. 19A is a graph showing an exemplary force profile during the injection process of an exemplary drug delivery device, where relative displacement between the device housing and the guard member is plotted along the x-axis (in millimeters) and resistance is plotted along the y-axis (Newtons)
Figure 19B:
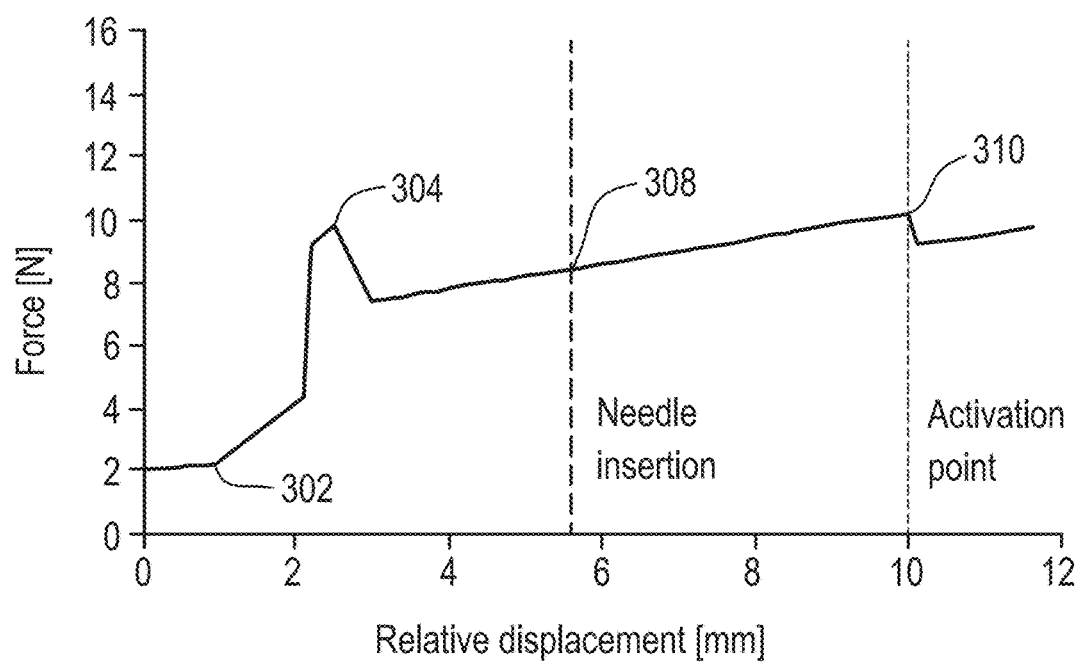
FIG. 19B is another exemplary force profile during the injection process of an exemplary drug delivery device, similar to that in FIG. 19A.

FIGS. 19A-19B each show an exemplary force profile during the injection process of an exemplary drug delivery device, where relative displacement between the device housing and the guard member is plotted along the x-axis (in millimeters) and resistance is plotted along the y-axis (Newtons). For example, the displacement (along the x-axis) shows the relative axial displacement along axis A between the guard member 32 and the housing 12. As discussed above, this relative axial displacement may be understood to refer to translational movement of the housing 12 with respect to the guard member 32 (such as in the case where a user urges the housing in the distal direction towards the user's injection site while the user's tissue prevents the guard member 32 from moving in the same direction) or it may be understood to refer to translational movement of the guard member 32 with respect to the housing (such as in the case where the housing 12 is held in place and a user pushes on the guard member 32 in the proximal direction). In any event, the x-axis (horizontal) of the graph in FIG. 19 shows relative displacement between the guard member 32 and the housing 12. The y-axis (vertical) of the graph in FIG. 19 shows the resistance force during the various points of relative displacement between the guard member 32 and the housing 12. For example, at the point where the guard member 32 and housing 12 have experienced approximately 2 mm of relative displacement, the resistance force experienced by the user is approximately 7.75N for the force profile shown in FIG. 19A. As an even more specific example, the resistance force may refer to the force experienced by a user due to mechanical interactions between components of the device. For example, when first urging the housing 12 towards the injection site during the pre-injection state shown in FIG. 14, the resistance force is generally equal to the force required to compress spring 51 as well as the force required to urge the inertial rib 32k past the ridge 40c. The force profile in FIGS. 19A-19B show several exemplary, potential desired force and displacement values, and thus it is understood that these values may vary depending on the design of the previously-noted interactions.

Nonetheless, as shown in the exemplary force profile in FIG. 19A, the initial resistance force is relatively low for the first approximately 1 mm of travel between the guard member 32 and the housing, whereupon at point 202 the resistance force quickly increases (primarily due to the force required to urge the inertial rib 32k past the ridge 40c) to a peak resistance force at point 204. Once the inertial rib 32k has cleared the ridge 40c (FIG. 15A), the resistance force quickly decreases to point 206, where the resistance force is primarily due to forces required to compress spring 51 (FIG. 14), forces required to compress spring 35 (FIG. 11B), and frictional forces between various moving components within the device. At point 208 the needle is inserted into the user's tissue and at point 210 the injection stage commences and the drug 22 is injected into the user's tissue. Once the user overcomes the peak resistance force at point 204, the user's inertia may drive the housing and the drug storage container toward the injection site, prompting the needle insertion. This stage of the injection (between point 204 and 208) may occur over a relatively short period of time, due to the user's inertia, to increase the likelihood that the needle is fully inserted rather than partially inserted and to decrease the likelihood that the user stops movement of the device before or during partial needle insertion. In other words, once the user clears the peak resistance force at point 204, the user may have "committed" to the needle insertion and/or the injection process.

FIG. 19B shows another exemplary force profile, where the peak force (point 304) is lower than the corresponding point (204) in FIG. 19A so as to require a lower initial force for the user to commit to the insertion. This force profile may make the user less likely to stop the process during the initial depression (point 302), such as prematurely removing the device from the tissue. However, it may be desirable to have the peak force 304 high enough to reduce the likelihood that the user stops the injection between the peak force 304 and the needle insertion 308. In other words, the vertical distance (along the y-axis) between points 304 and 308 should be large enough to cause this stage of the injection to occur over a relatively short period of time.

Figure 20A:
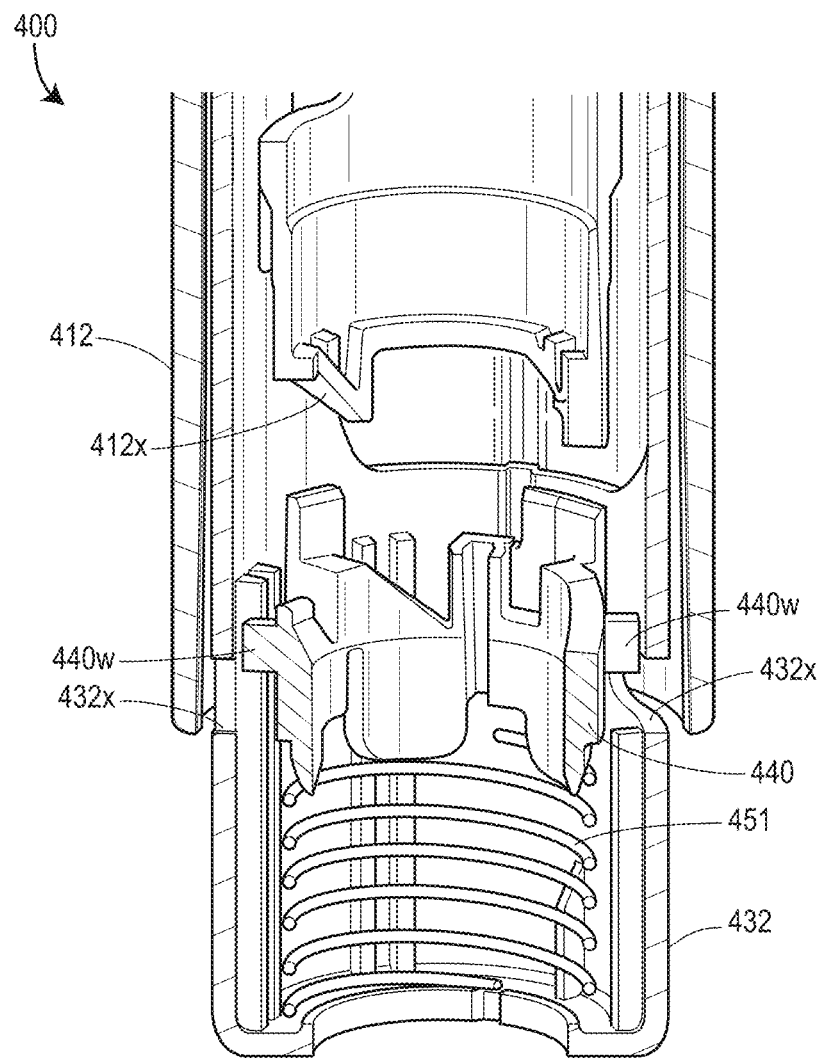
FIGS. 20A-20G show another exemplary drug delivery device in accordance with various embodiments.
Figure 20B:
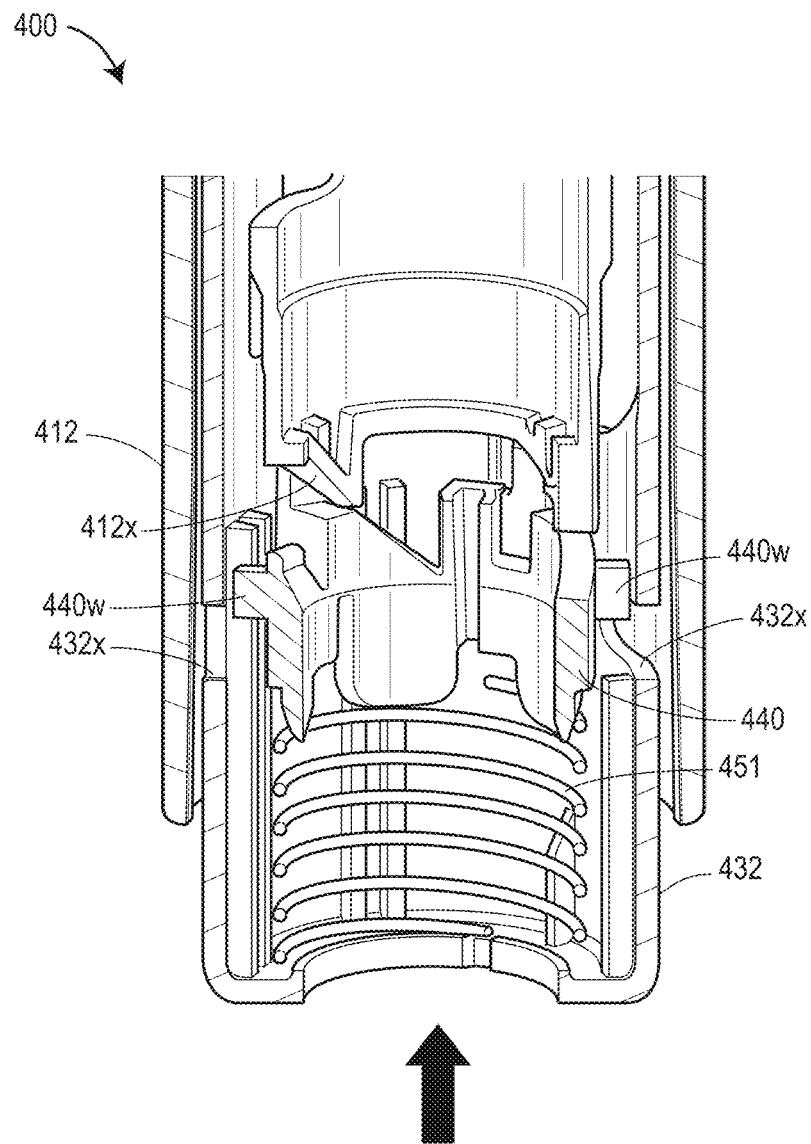
Figure 20C:
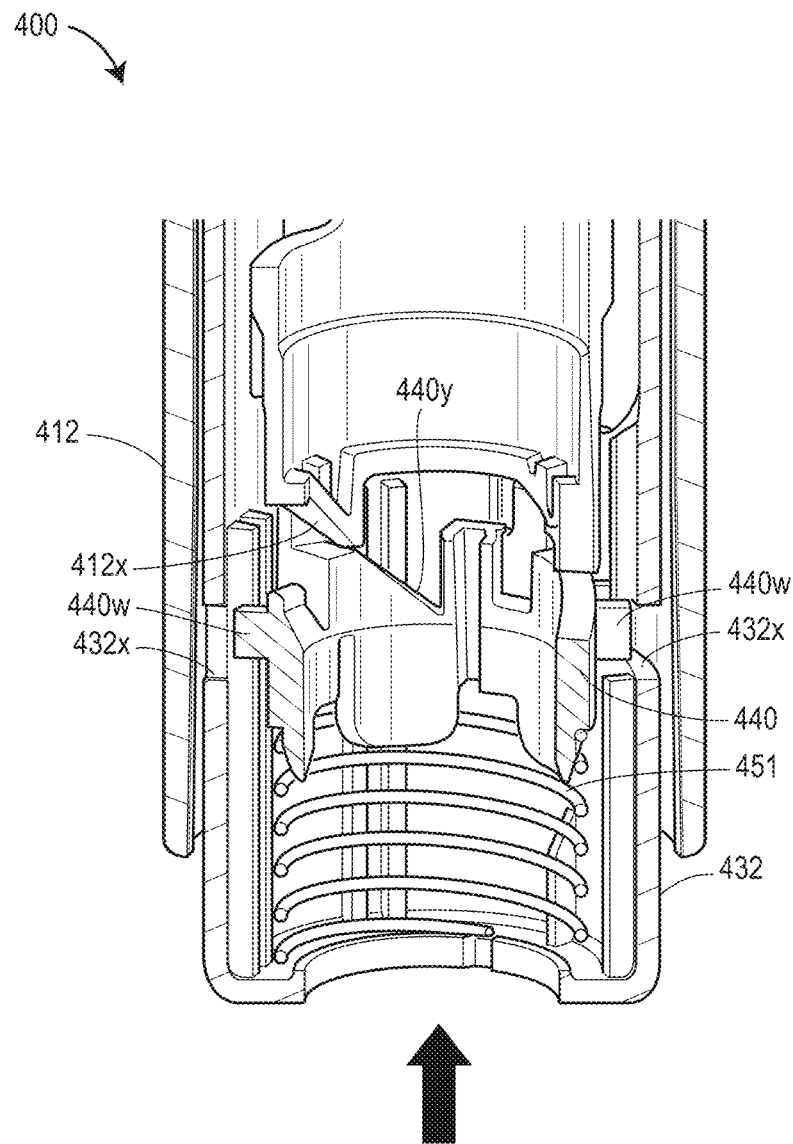
Figure 20D:
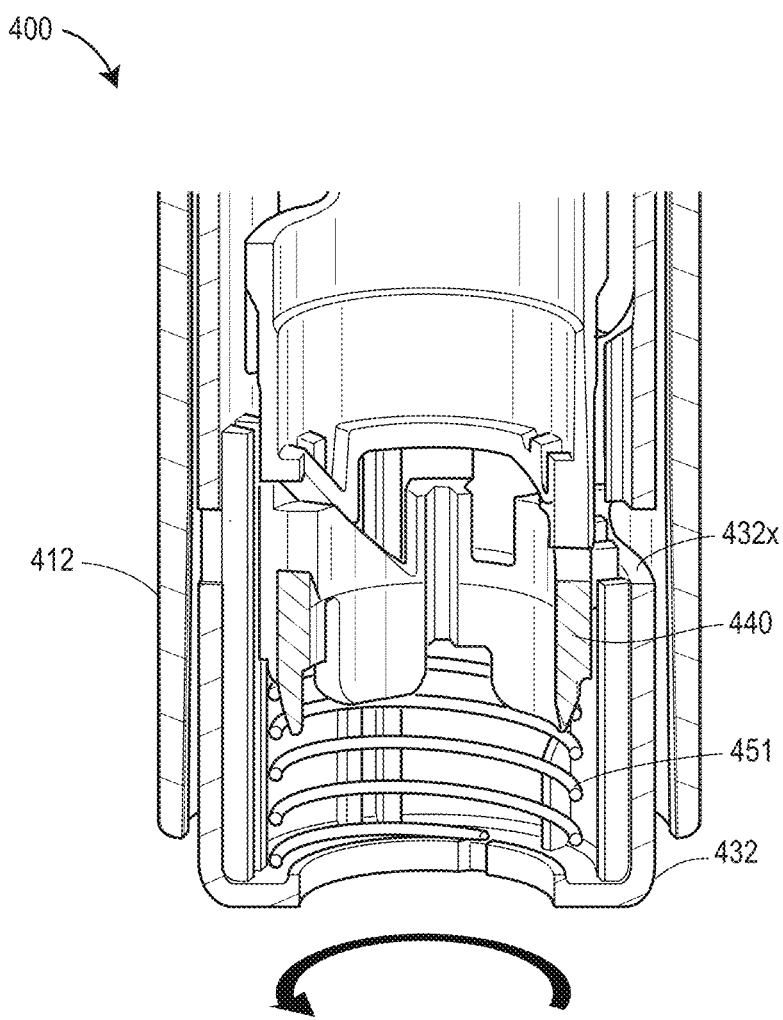
Figure 20E:
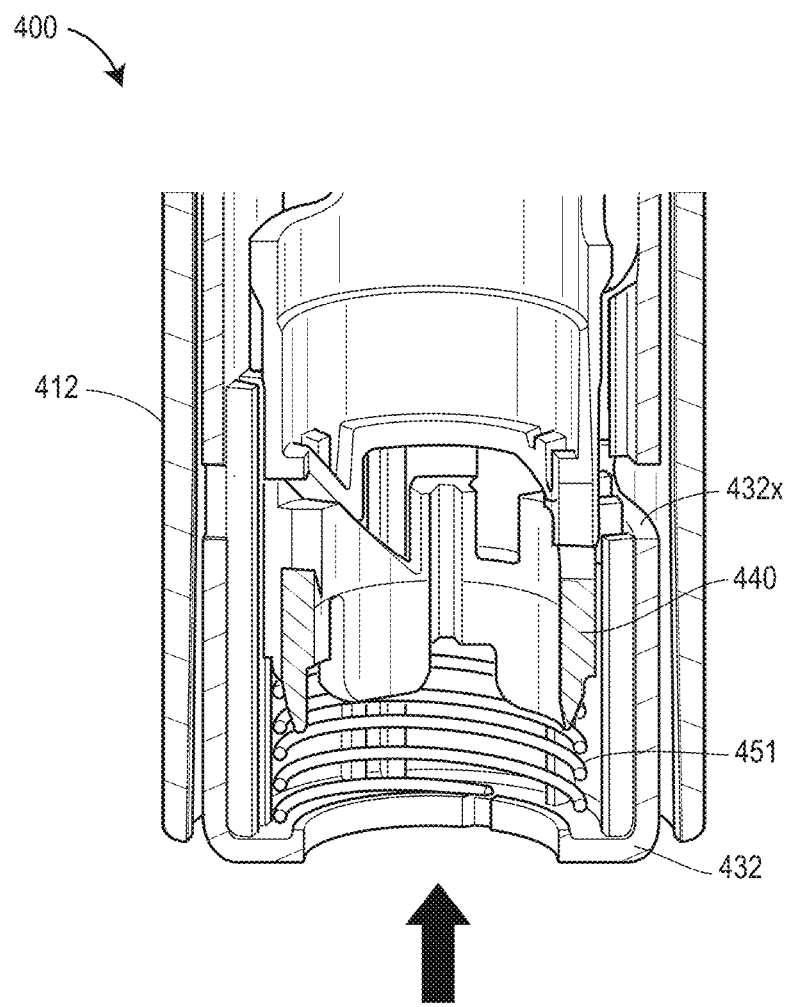
Figure 20F:
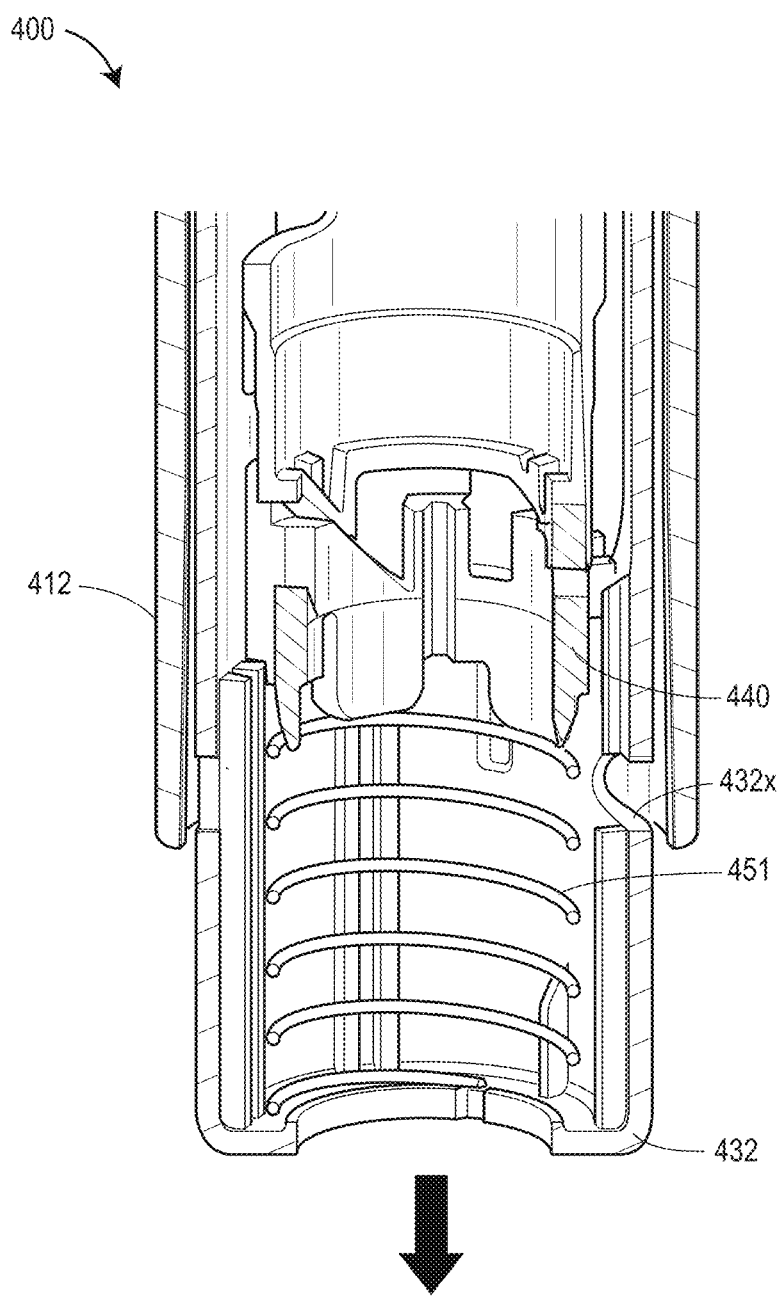
Figure 20G:
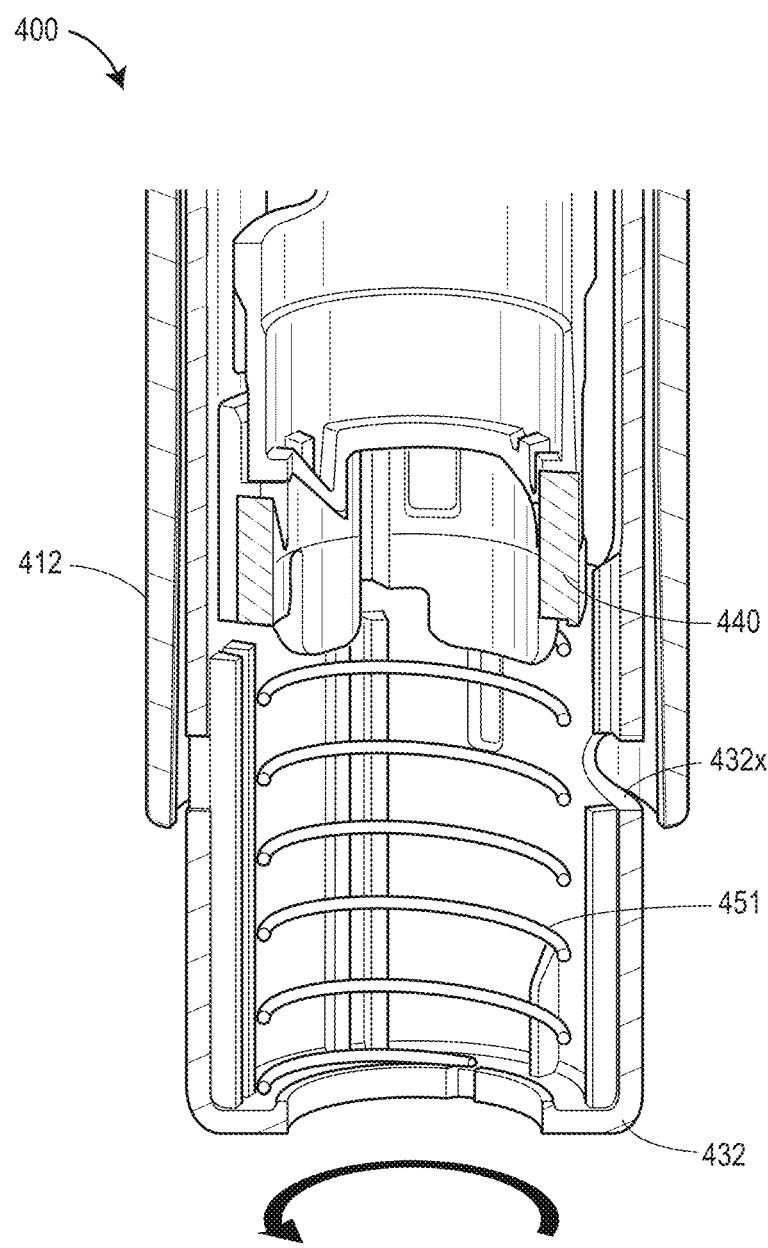
Figure 22:
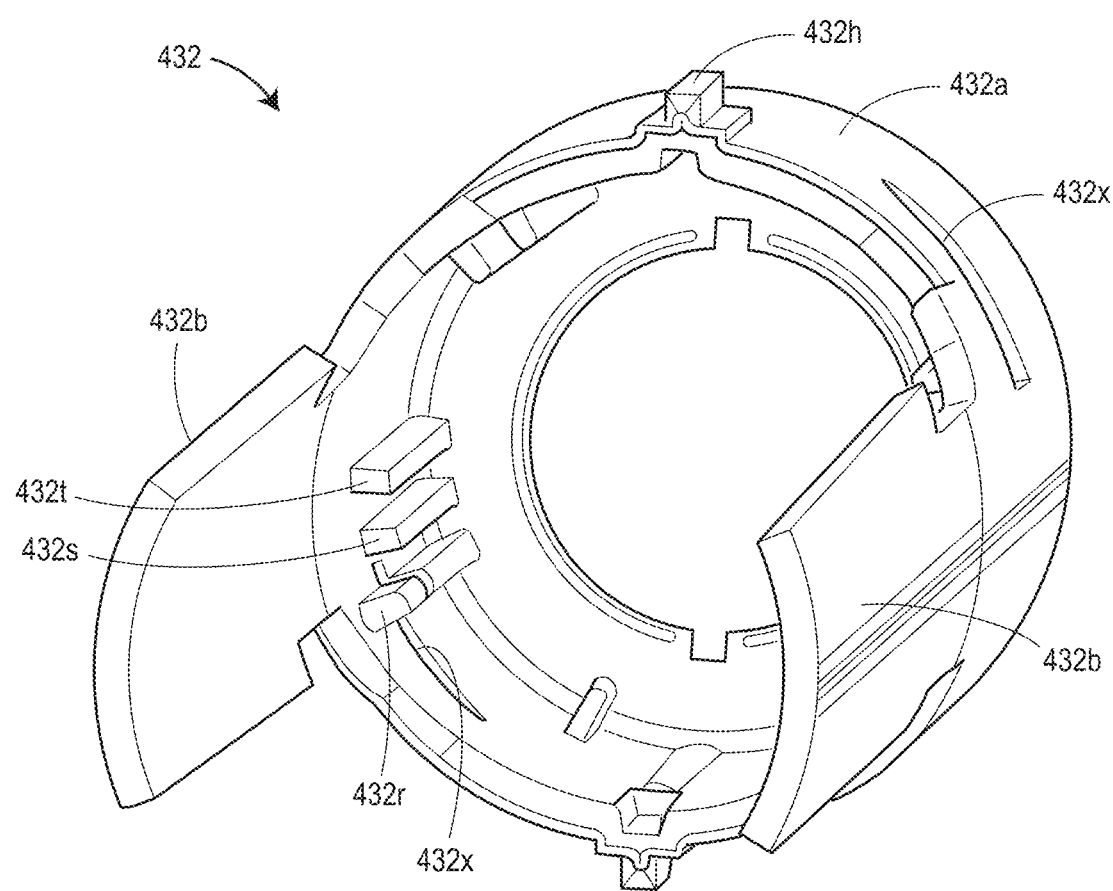
FIG. 22 shows the guard member shown in FIGS. 20A-20G and FIGS. 21A-21F.
Figure 23:
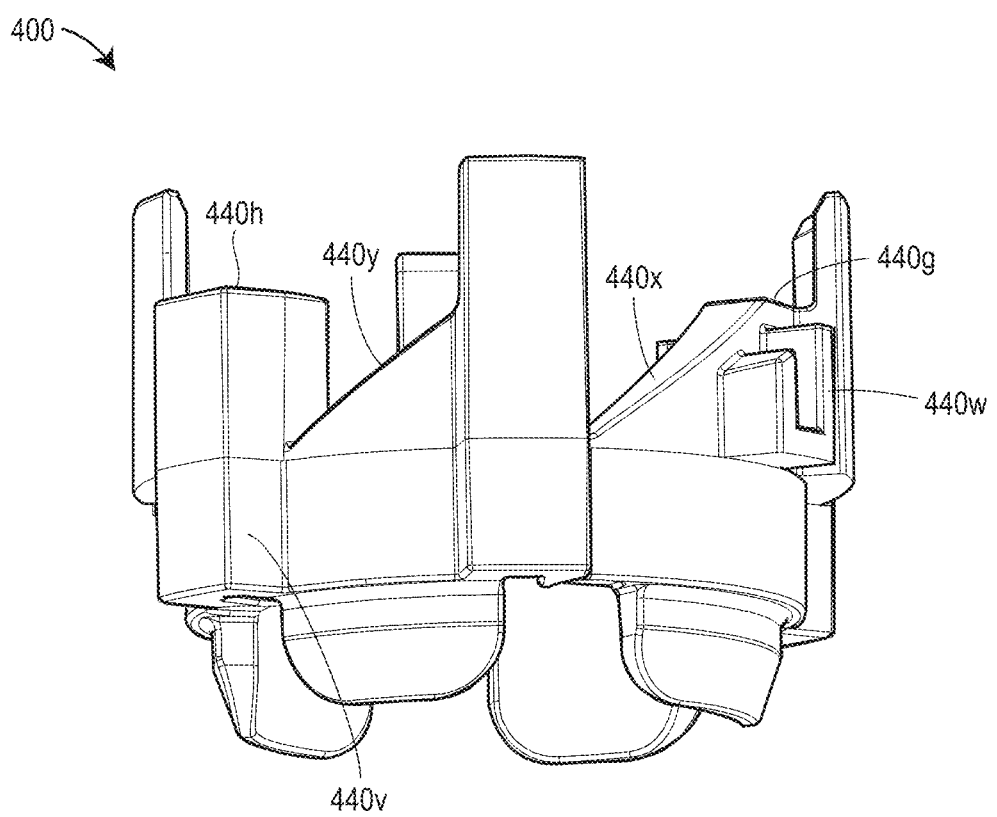
FIG. 23 shows the lock ring shown in FIGS. 20A-20G.

FIGS. 20A through 20G show a distal portion of an alternative design of a device 400, primarily showing a housing 412, a guard member 432, a lock ring 440, and a lock ring biasing member 451. As shown in FIG. 20A and FIG. 22, the guard member 432 includes an annular base portion 432a, a pair of longitudinally-extending arms 432b, a ridge 432h, a plurality of inner ribs (discussed in more detail below), and at least one opening 432x (also referred to as a hole in the annotations to some of the figures) formed through at least one of the ribs and a wall of the guard member. The opening 432x need not be an opening formed through the entire wall of the guard member 432. For example, the opening may be merely a disconnection in the long rib or a protrusion section with a shorter height rather than a cut-out of the wall of the guard member 432 and a portion of the rib. The inner ribs of the guard member 432 include a first rib that is preferably longer than the other ribs (a.k.a. the long rib 432r), and a pair of shorter ribs 432s, 432t. The opening 432x is formed through the long rib 432r and is aligned with and sized such as to selectively receive a component of the lock ring 440, as will be discussed further below. As shown in FIG. 20A and FIG. 23, the lock ring 440 includes a plurality of stop surfaces 440g, 440h, a U-shaped projection 440w (configured to be received within the opening 432x), and plurality of proximally-facing cam surfaces 440x, 440y. However, the lock ring 440 shown in FIGS. 20A and 23 does not have distally-facing cam surfaces corresponding to surface 40a in the design shown in FIG. 13. As shown in FIG. 20A, during a pre-injection, non-deflection state of the device 400, each of the two U-shaped projections 440w are not initially received within the openings 432x. Rather, at this point, the proximal portion of the long rib 432r (i.e. the portion of the long rib that is proximal of the opening 432x) is received within the U-shaped projection 440w such as to prevent the lock ring from moving upwards (proximal direction) with respect to the guard member. As the housing 412 moves downward (distally) and/or the guard member 432 moves upward (proximally), as shown in FIG. 20B, the lock ring 440 is able to move upward (proximally) from the spring 451, thereby causing cam surfaces on the housing 412 to contact the lock ring camming surfaces 440x, 440y and rotationally urge the lock ring. At the stage shown in FIG. 20B, the lock ring 440 is unable to rotate due to the proximal portion of the long rib 432r being aligned with/received within the U-shaped projection 440w. Also as shown in FIG. 20B, the housing cam surface 412x engages the lock ring cam surface 440y. However, as the relative movement between the guard member and the housing progresses to the state shown in FIG. 20C, the engagement between the housing cam surface 412x and the lock ring cam surface 440y, combined with further relative movement between the guard member and the housing cause the following: (1) the engagement between the housing cam surface 412x and the lock ring cam surface 440y halts upward movement of the lock ring so that the proximal portion of the long rib 432r is able to move out of alignment with/engagement with the U-shaped projection 440 such that the U-shaped projection 440w is now aligned with the opening 432x and (2) the respective cam surface engagement 412x, 440y causes the lock ring 440 to rotate. As shown in FIG. 20D, the lock ring rotates to a point (roughly two-thirds of its total rotation) where it is now rotationally constrained by the short ribs 432s, 432t in the guard member (more specifically, a stop surface 440v shown in FIG. 23 engages the short ribs 432s, 432t). In the state shown in FIG. 20E, the guard member arms 432b sufficiently move relative to the housing 412 such that the injection sequence initiates. As shown in FIG. 20F, once the user releases pressure on the housing and permits relative proximal movement of the housing and/or distal movement of the guard member, the lock ring is rotationally constrained until stop surface 440v clears the short ribs 432s, 432t and the lock ring rotates into a lock out configuration shown in FIG. 20G.

Figure 26A:
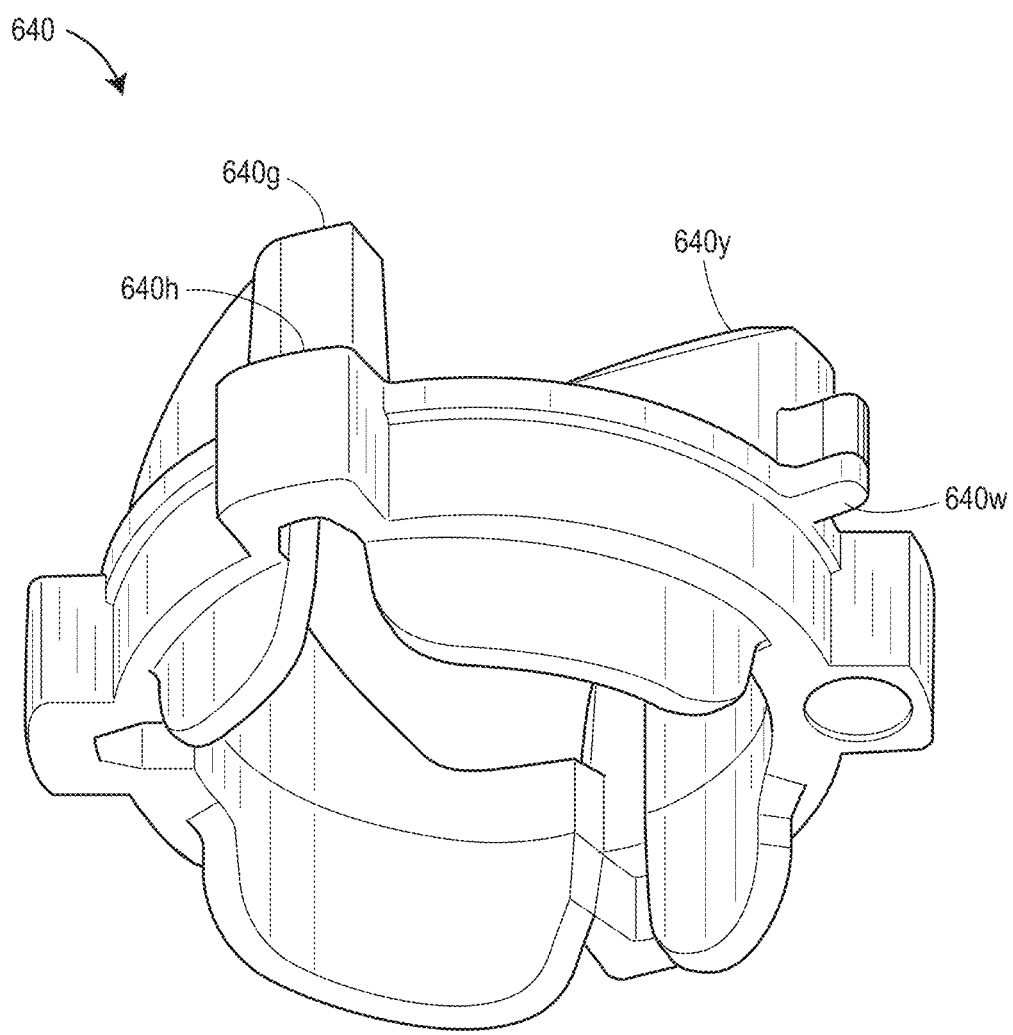
FIGS. 26A-26D depict another exemplary drug delivery device in accordance with various embodiments, with FIGS. 26A and 26B illustrating different perspective views of a lock ring of the drug delivery device, FIG. 26C illustrating a perspective view of a guard member of the drug delivery device, and FIG. 26D illustrating a cutaway view of a portion of the drug delivery device.
Figures 26B, 26C:
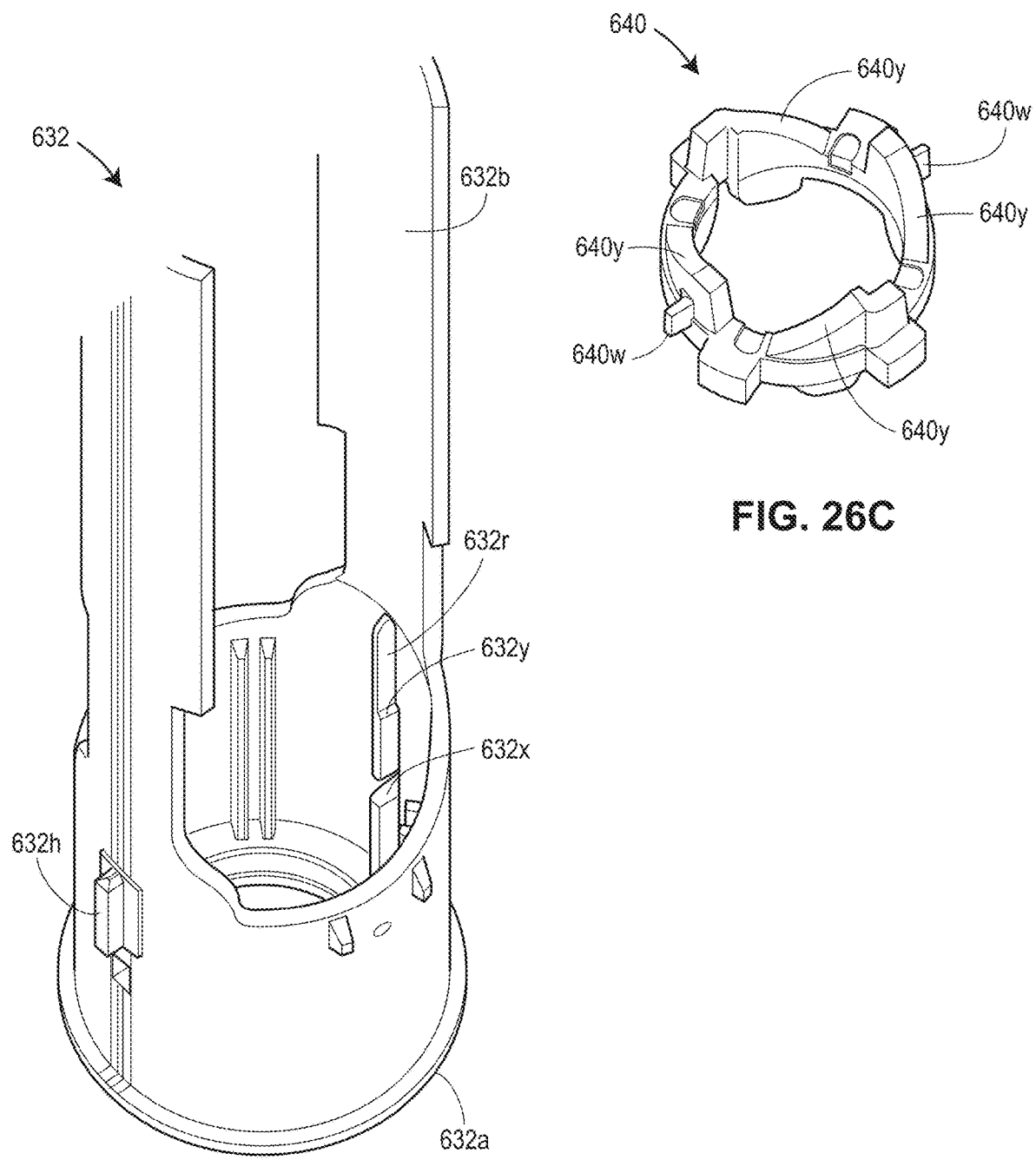
Figure 26D:
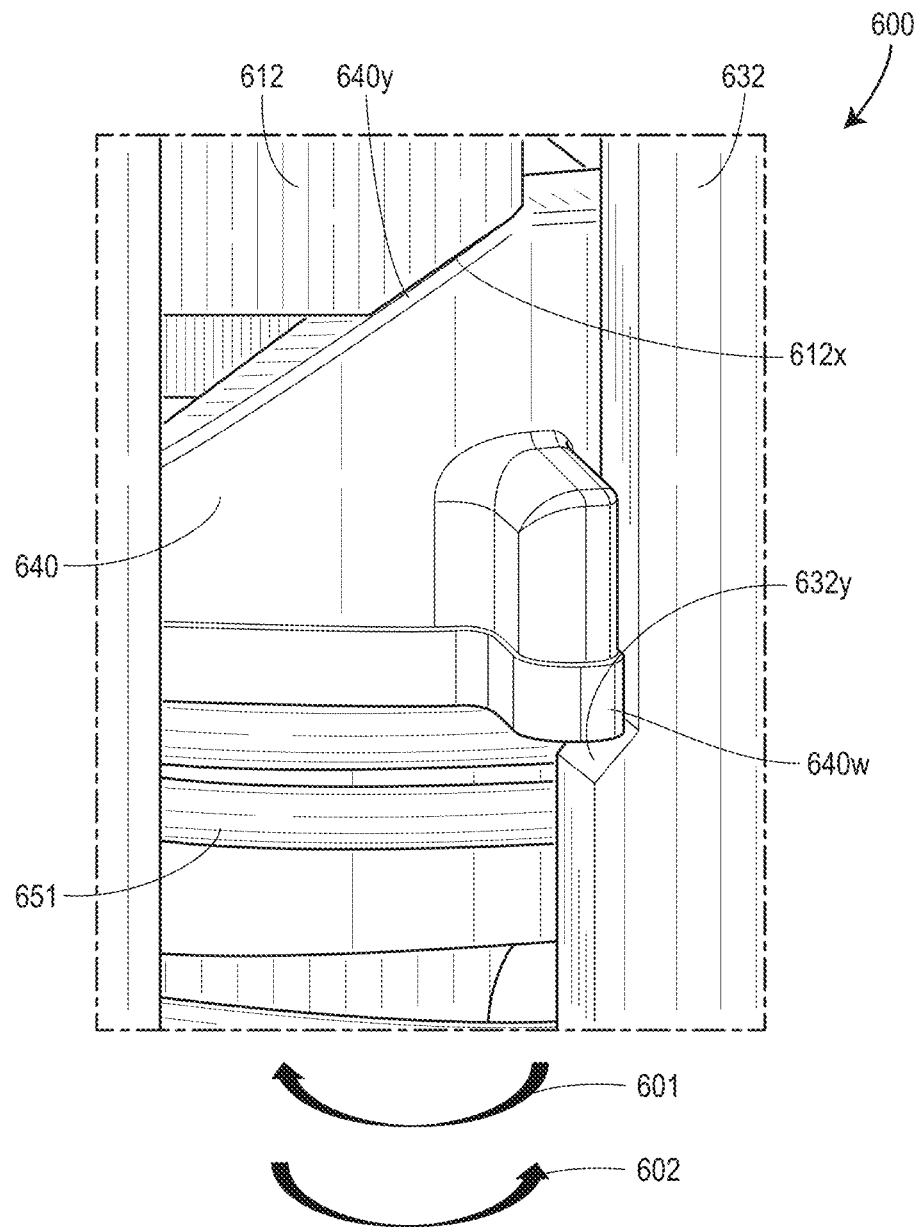

FIGS. 26A through 26D show another alternative design of a device 600, primarily showing a housing 612, a guard member 632, a lock ring 640, and a lock ring biasing member 651. As shown in 26C, the guard member 632 includes an annular base portion 632a, a pair of longitudinally-extending arms 632b, a ridge 632h, a plurality of inner ribs (discussed in more detail below), and at least one opening 632x (also referred to as a hole herein) formed through at least one of the ribs and a wall of the guard member. Each of the ribs of the guard member 632 may be configured as a radially inwardly extending protrusion. The opening 632x need not be an opening formed through the entire wall of the guard member 632. For example, the opening 632x may be merely a disconnection in the long rib or a protrusion section with a shorter height rather than a cut-out of the wall of the guard member 632 and a portion of the rib. The opening 632x is formed through rib 632r and is aligned with and sized such as to selectively receive a component of the lock ring 640, as will be discussed further below. As shown in FIGS. 26A, 26B, and 26D, the lock ring 640 includes a plurality of stop surfaces 640g, 640h, at least one tab-shaped projection 640w (configured to be received within the opening 632x), and plurality of proximally-facing camming surfaces 640y. As illustrated in FIG. 26A, each tab-shaped projection 640w may be configured as a radially outwardly extending protrusion and may include proximally-facing camming surface 640z. As shown in FIG. 26D, during a pre-injection, partial-deflection state of the device 600, each of the two tab-shaped projections 640w are not initially received within the openings 632x. Rather, at this point, a proximally-facing camming surface 612x of housing 612 engages the distally-facing camming surface 640y of the lock ring 640 to prevent or resist the lock ring 640 from moving upwards (proximal direction) with respect to the guard member 632. At the same time, the tab-shaped projections 640w are each respectively engaged with a pair of ramp surfaces 632y (also referred to herein as proximally-facing camming surfaces 632y). At this stage of the injection, the guard member 632 has been partially deflected (such as in FIG. 20B) but the lock ring 640 has not yet rotated and the guard member 632 has not yet moved upwards a distance sufficient to initiate the injection sequence. At this point, the user will feel a resistance to further movement of the injector housing 612, due to the respective engagements described above, namely the proximally-facing camming surface 612x of the housing 612 with the distally-facing camming surface 640y of the lock ring 640 and the proximally-facing camming surface 640z of the tab-shaped projection 640w of the lock ring 640 with the guard member ramp surface 632y. This resistance may or likely will prompt the user to press down on the injector with a force sufficient to overcome the resistance (i.e. the peak resistance of the injector). The peak resistance is caused by the aforementioned interactions (the distally-facing camming surface 612x of the housing 612 with the proximally-facing camming surface 640y of the lock ring 640 and the distally-facing camming surface 640z of the tab-shaped projection 640w of the lock ring 640 with the guard member ramp surface 632y) and it is overcome (i.e. released) when the user's force is sufficient such that the tab-shaped projection 640w of the lock ring 640 slides along the guard member ramped surface 632y and the proximally-facing camming surface 640y of the lock ring 640 will slide along the distally-facing camming surface 612x of the housing 612 (to the left in FIG. 26D). In other words, the lock ring 640 will rotate in the direction of arrow 601 and will travel slightly downward (distally) shown in FIG. 26D. Once the lock ring 640 rotates enough so that the lock ring tab-shaped projection 640w has cleared the guard member ramped surface 632y, the guard member 632 will be able to move axially upward (proximally). At this point, two things will happen: (1) the guard member 632 will translate in the proximal direction a sufficient distance such as to initiate the injection sequence and (2) the lock ring tab-shaped projection 640w will become axially aligned with guard member opening 632x (FIG. 26C) and thereby allow the lock ring 640 to rotate in the direction of arrow 602 (FIG. 26D) and slightly upwards (proximal direction) due to the interaction between the proximally-facing camming surface 640y of the lock ring 640 and the distally-facing camming surface 612x of the housing 612. After the injection is initiated, the lock ring 640 will be in a position where it can lock-out the shield, similar to the other embodiments described above. The injector 600 may be designed such that events (1) and (2) occur simultaneously, so that once the guard member translates a distance sufficient to initiate the injection, the lock ring will rotate an angle sufficient to initiate the lock-out sequence. This may be desirable to substantially or completely prevent a user from attempting to perform multiple injections. This may also be desirable to substantially or completely prevent the lock-out sequence from initiating without the injection sequence also initiating. In other words, the above configuration may reduce the likelihood that a user has a locked-out injector with an undelivered dose.

To facilitate rotation of the lock ring 640 relative to the housing 612 and/or the guard member 632, any two or combination of the following may be parallel to each other: the distally-facing camming surface(s) 612x of the housing 612, the proximally-facing camming surface(s) 632y of the guard member 632, the distally-facing camming surface(s) 640z of the lock ring 640, and the proximally-facing camming surface(s) 640y of the lock ring 640.

Figure 21A:
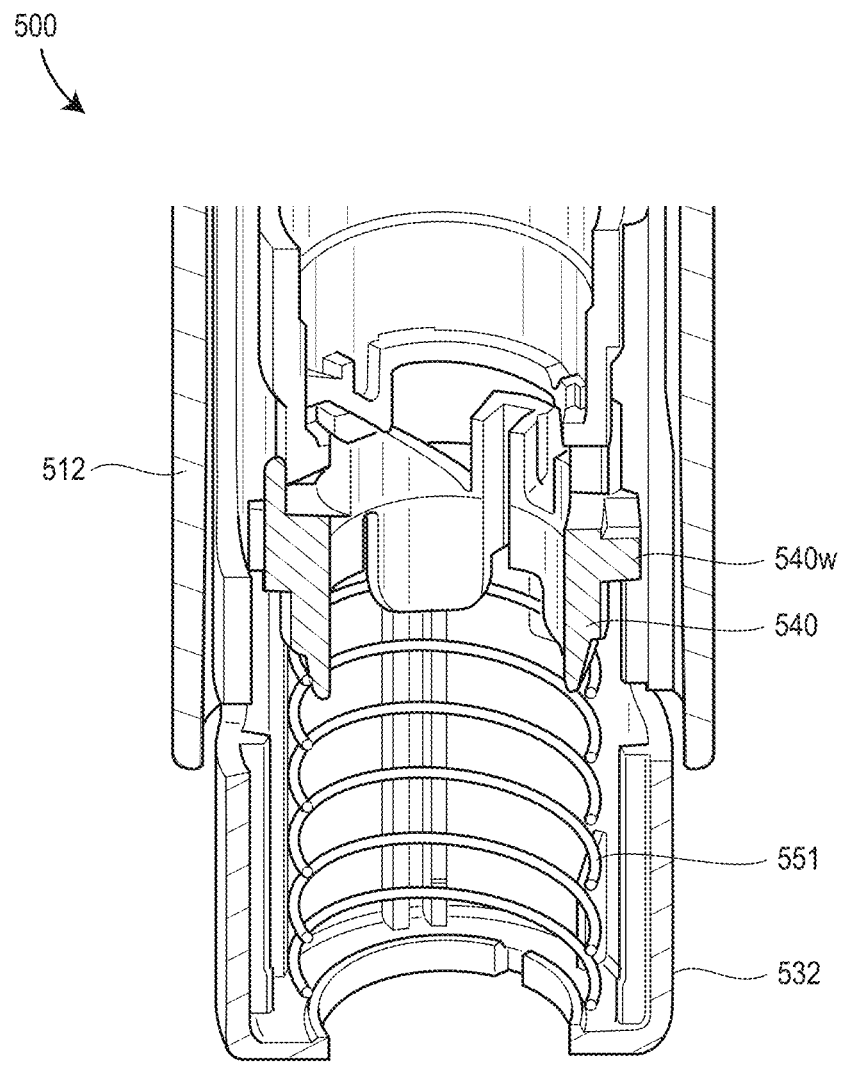
FIGS. 21A-21F show yet another exemplary drug delivery device in accordance with various embodiments.
Figure 21B:
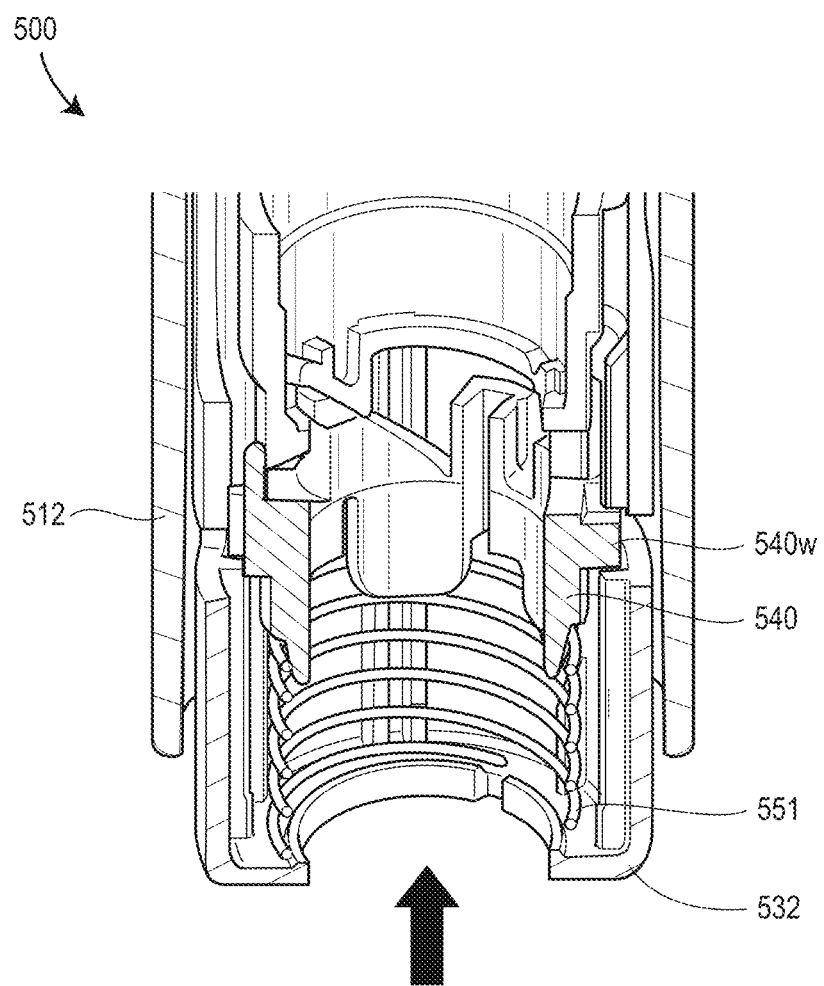
Figure 21C:
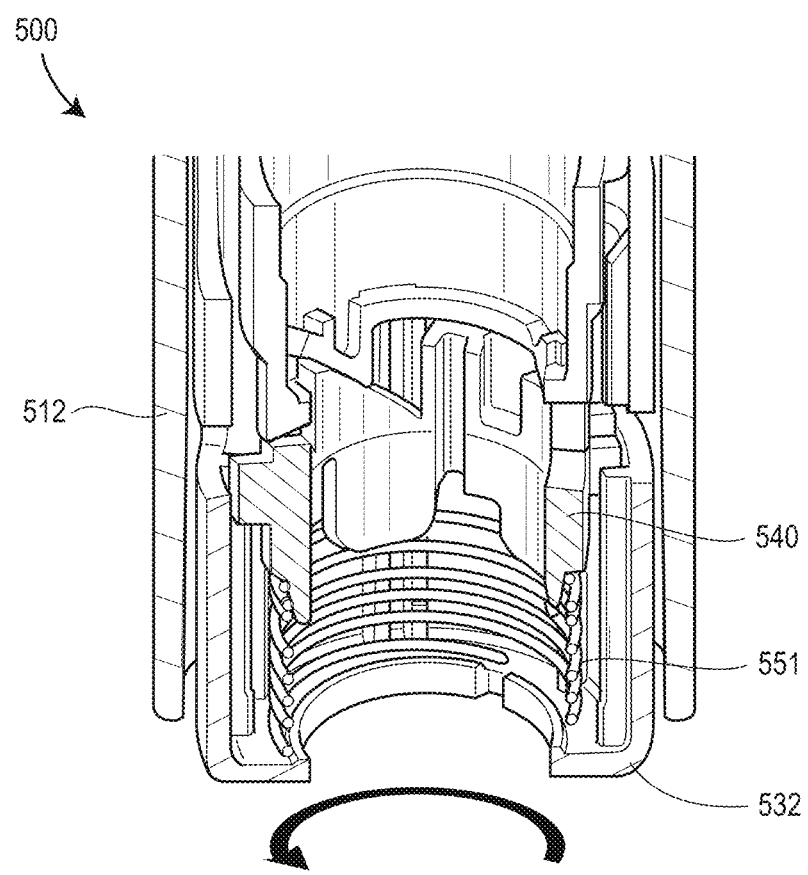
Figure 21D:
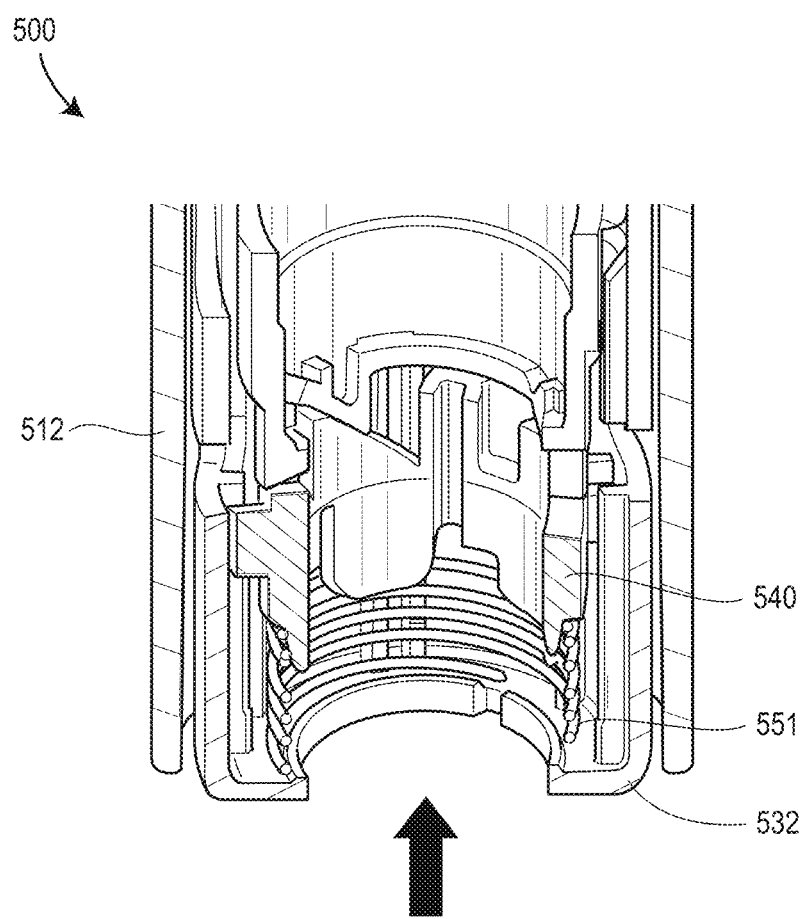
Figure 21E:
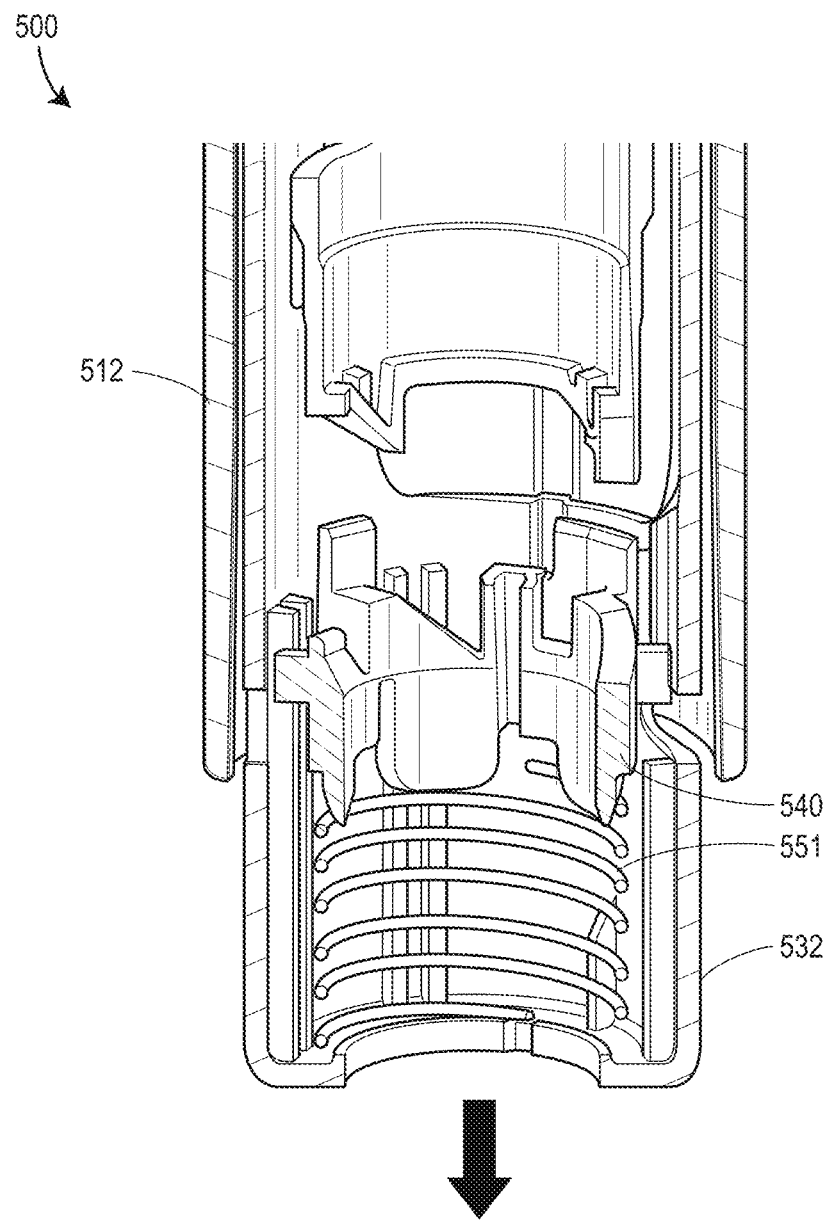
Figure 21F:
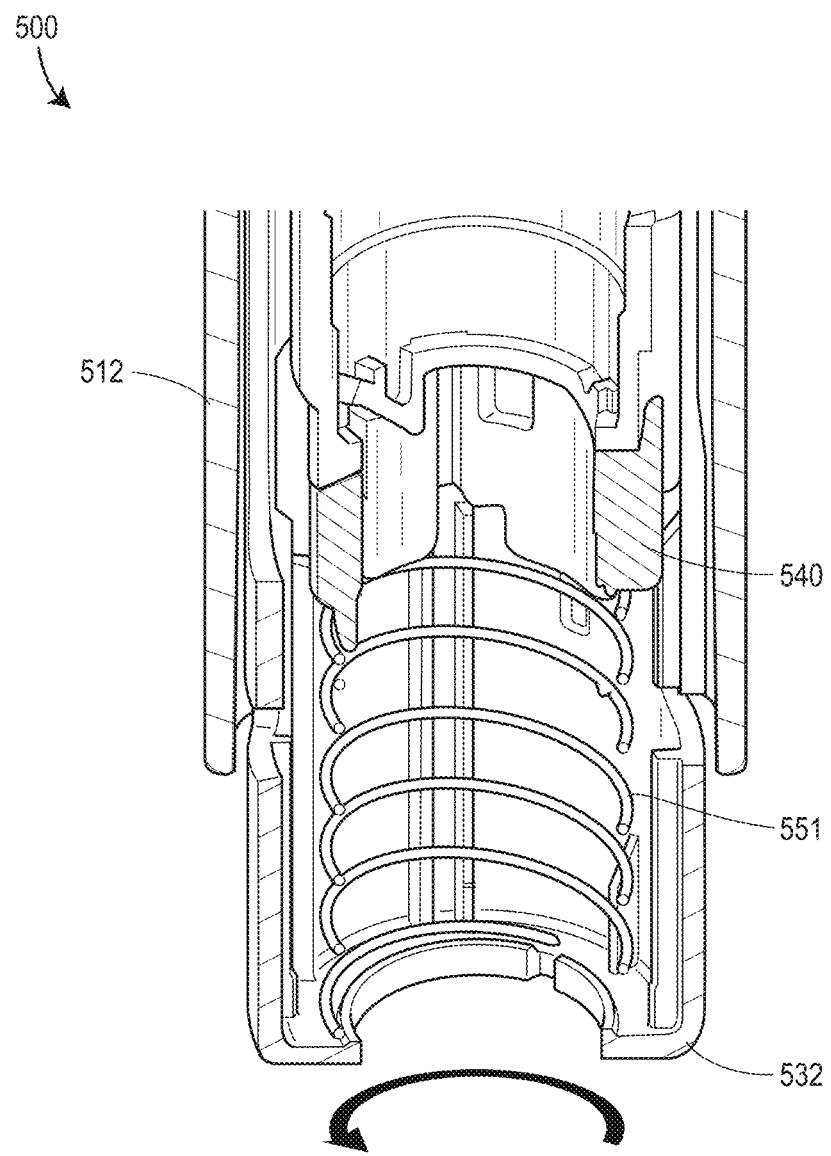

FIGS. 21A through 21F show a distal portion of another alternative design of a device 500, primarily showing a housing 512, a guard member 532, a lock ring 540, and a lock ring biasing member 551. The components of the device 500 are similar to those on the device 400, except that instead of the U-shaped projection 440w, the lock ring 540 has only a pair of parallel projections 540w that do not have a horizontal projection connecting them. In other words, the projections 540w have the "side portions" of a U-shape but do not have the "bottom portion" of a U-shape. In the state shown in FIG. 21A, the projections 540w are received within a long rib of the guard member 532 to prevent rotational movement of the lock ring. As relative movement occurs between the guard member and the housing, as shown in FIG. 21B, the projections 540w become aligned with an opening in the guard member, thereby allowing rotational movement of the lock ring with respect to the guard member (and urged by a camming surface on the housing). As shown in the state in FIG. 21C, the lock ring then rotates until stop surface 440v engages the short ribs in the guard member. FIG. 21D shows the distal components of the device during the injection activation. FIG. 21E shows the state of the distal components once the user has released pressure and the guard member is able to move (extend distally) relative to the housing. FIG. 21F shows the lock-out configuration.

Figure 24:
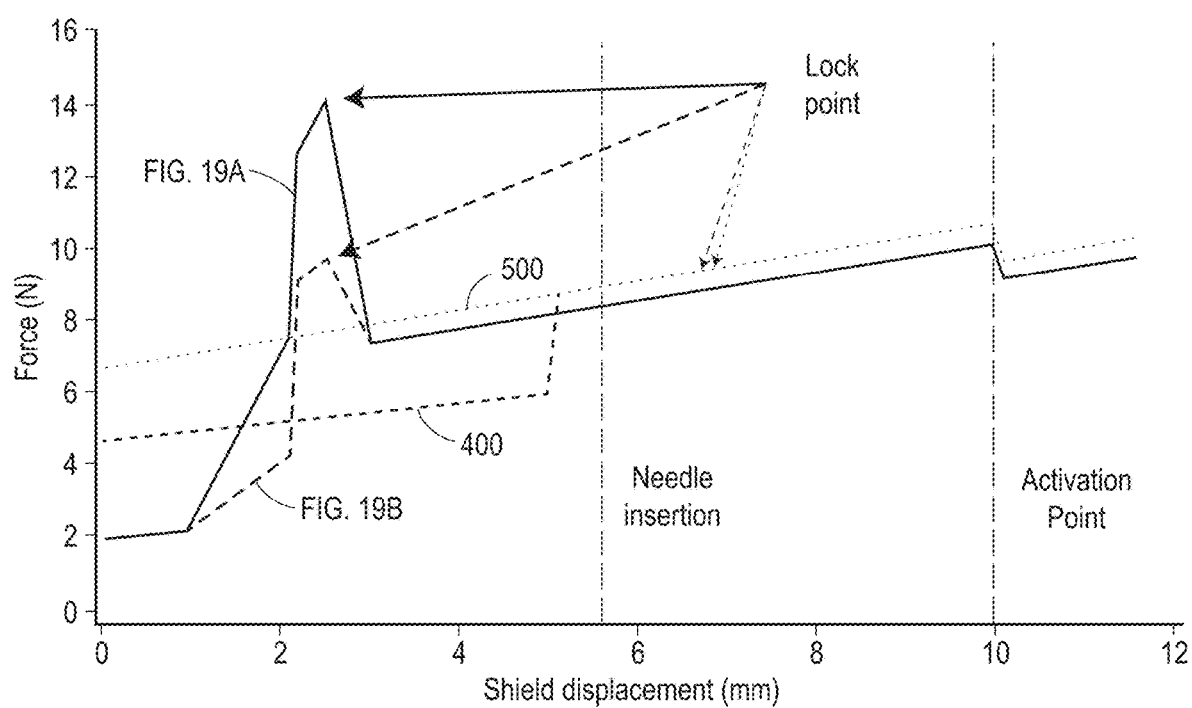
FIG. 24 shows the force profiles of various devices, with two of the force profiles shown in FIGS. 19A and 19B, respectively, one force profile (illustrated as a dashed line) attributable to the device 400 shown in FIGS. 20A-20G, and another force profile (illustrated as a dotted line) attributable to the device 500 shown in FIGS. 21A-21F.

FIG. 24 provides a graph for comparing the force profiles illustrated in FIGS. 19A and 19B with force profiles attributable to the drug delivery device 400 shown in FIGS. 20A-20G and the drug delivery device 500 shown in FIGS. 21A-21F. Similar to FIGS. 19A and 19B, FIG. 24 plots the resistance force experienced by a user versus displacement of a shield (e.g., the shield guard 32). Additionally, FIG. 24 identifies where in each force profile a lock point associated with a lock ring is designed to occur. FIG. 24 shows that the lock point for the force profiles in FIGS. 19A and 19B occurs at the same shield displacement as when the user experiences a peak resistance. By contrast, the lock point for the force profiles associated with drug delivery devices 400 and 500 does not coincide with a shield displacement corresponding to a peak resistance experienced by the user.

Continuing with FIG. 24, the force profile associated with the drug delivery device 400 is similar to the force profiles in FIGS. 19A and 19B in that prior to needle insertion the user experiences a sudden jump in resistance caused by displacing the shield. Unlike the force profiles in FIGS. 19A and 19B, the resistance experienced by the user of the drug delivery device 400 may continue to increase after this jump (until the activation point). FIG. 24 shows that the user of the drug delivery device 500 may not experience a sudden jump in resistance during shield displacement but rather may experience a gradual increase in resistance until the activation point. A manufacturer may choose one of the force profiles illustrated in FIG. 24 or a different force profiles depending on, for example, a desired user experience, physical and/or mental abilities of a target user or patient population, mechanical safety considerations, and/or additional considerations.

From the foregoing, it can be seen that the present disclosure advantageously provides a streamlined design for a drug delivery device having automated features. Various mechanisms and components of the drug delivery device may interact with each other in synergistic ways so as to limit the number of moving parts required by the drug delivery device, thereby improving the reliability of the drug delivery device and saving costs, as well as providing other benefits and advantages.

As will be recognized, the devices and methods according to the present disclosure may have one or more advantages relative to conventional technology, any one or more of which may be present in a particular embodiment in accordance with the features of the present disclosure included in that embodiment. Other advantages not specifically listed herein may also be recognized as well.

The above description describes various devices, assemblies, components, subsystems and methods for use related to a drug delivery device. The devices, assemblies, components, subsystems, methods or drug delivery devices can further comprise or be used with a drug including but not limited to those drugs identified below as well as their generic and biosimilar counterparts. The term drug, as used herein, can be used interchangeably with other similar terms and can be used to refer to any type of medicament or therapeutic material including traditional and non-traditional pharmaceuticals, nutraceuticals, supplements, biologics, biologically active agents and compositions, large molecules, biosimilars, bioequivalents, therapeutic antibodies, polypeptides, proteins, small molecules and generics. Non-therapeutic injectable materials are also encompassed. The drug may be in liquid form, a lyophilized form, or in a reconstituted from lyophilized form. The following example list of drugs should not be considered as all-inclusive or limiting.

The drug will be contained in a reservoir. In some instances, the reservoir is a primary container that is either filled or pre-filled for treatment with the drug. The primary container can be a vial, a cartridge or a pre-filled syringe.

In some embodiments, the reservoir of the drug delivery device may be filled with or the device can be used with colony stimulating factors, such as granulocyte colony-stimulating factor (G-CSF). Such G-CSF agents include but are not limited to Neulasta® (pegfilgrastim, pegylated filgastrim, pegylated G-CSF, pegylated hu-Met-G-CSF) and Neupogen® (filgrastim, G-CSF, hu-MetG-CSF), UDE-NYCA® (pegfilgrastim-cbqv), Ziextenzo® (LA-EP2006; pegfilgrastim-bmez), or FULPHILA (pegfilgrastim-bmez).

In other embodiments, the drug delivery device may contain or be used with an erythropoiesis stimulating agent (ESA), which may be in liquid or lyophilized form. An ESA is any molecule that stimulates erythropoiesis. In some embodiments, an ESA is an erythropoiesis stimulating protein. As used herein, "erythropoiesis stimulating protein" means any protein that directly or indirectly causes activation of the erythropoietin receptor, for example, by binding to and causing dimerization of the receptor. Erythropoiesis stimulating proteins include erythropoietin and variants, analogs, or derivatives thereof that bind to and activate erythropoietin receptor; antibodies that bind to erythropoietin receptor and activate the receptor; or peptides that bind to and activate erythropoietin receptor. Erythropoiesis stimulating proteins include, but are not limited to, Epogen® (epoetin alfa), Aranesp® (darbepoetin alfa), Dynepo® (epoetin delta), Mircera® (methyoxy polyethylene glycol-epoetin beta), Hematide®, MRK-2578, INS-22, Retacrit® (epoetin zeta), Neorecormon® (epoetin beta), Silapo® (epoetin zeta), Binocrit® (epoetin alfa), epoetin alfa Hexal, Abseamed® (epoetin alfa), Ratioepo® (epoetin theta), Eporatio® (epoetin theta), Biopoin® (epoetin theta), epoetin alfa, epoetin beta, epoetin iota, epoetin omega, epoetin delta, epoetin zeta, epoetin theta, and epoetin delta, pegylated erythropoietin, carbamylated erythropoietin, as well as the molecules or variants or analogs thereof.

Among particular illustrative proteins are the specific proteins set forth below, including fusions, fragments, analogs, variants or derivatives thereof: OPGL specific antibodies, peptibodies, related proteins, and the like (also referred to as RANKL specific antibodies, peptibodies and the like), including fully humanized and human OPGL specific antibodies, particularly fully humanized monoclonal antibodies; Myostatin binding proteins, peptibodies, related proteins, and the like, including myostatin specific peptibodies; IL-4 receptor specific antibodies, peptibodies, related proteins, and the like, particularly those that inhibit activities mediated by binding of IL-4 and/or IL-13 to the receptor; Interleukin 1-receptor 1 ("IL1-R1") specific antibodies, peptibodies, related proteins, and the like; Ang2 specific antibodies, peptibodies, related proteins, and the like; NGF specific antibodies, peptibodies, related proteins, and the like; CD22 specific antibodies, peptibodies, related proteins, and the like, particularly human CD22 specific antibodies, such as but not limited to humanized and fully human antibodies, including but not limited to humanized and fully human monoclonal antibodies, particularly including but not limited to human CD22 specific IgG antibodies, such as, a dimer of a human-mouse monoclonal hLL2 gamma-chain disulfide linked to a human-mouse monoclonal hLL2 kappa-chain, for example, the human CD22 specific fully humanized antibody in Epratuzumab, CAS registry number 501423-23-0; IGF-1 receptor specific antibodies, peptibodies, and related proteins, and the like including but not limited to anti-IGF-1R antibodies; B-7 related protein 1 specific antibodies, peptibodies, related proteins and the like ("B7RP-1" and also referring to B7H2, ICOSL, B7h, and CD275), including but not limited to B7RP-specific fully human monoclonal IgG2 antibodies, including but not limited to fully human IgG2 monoclonal antibody that binds an epitope in the first immunoglobulin-like domain of B7RP-1, including but not limited to those that inhibit the interaction of B7RP-1 with its natural receptor, ICOS, on activated T cells; IL-15 specific antibodies, peptibodies, related proteins, and the like, such as, in particular, humanized monoclonal antibodies, including but not limited to HuMax IL-15 antibodies and related proteins, such as, for instance, 145c7; IFN gamma specific antibodies, peptibodies, related proteins and the like, including but not limited to human IFN gamma specific antibodies, and including but not limited to fully human anti-IFN gamma antibodies; TALL-1 specific antibodies, peptibodies, related proteins, and the like, and other TALL specific binding proteins; Parathyroid hormone ("PTH") specific antibodies, peptibodies, related proteins, and the like; Thrombopoietin receptor ("TPO-R") specific antibodies, peptibodies, related proteins, and the like; Hepatocyte growth factor ("HGF") specific antibodies, peptibodies, related proteins, and the like, including those that target the HGF/SF:cMet axis (HGF/SF:c-Met), such as fully human monoclonal antibodies that neutralize hepatocyte growth factor/scatter (HGF/SF); TRAIL-R2 specific antibodies, peptibodies, related proteins and the like; Activin A specific antibodies, peptibodies, proteins, and the like; TGF-beta specific antibodies, peptibodies, related proteins, and the like; Amyloid-beta protein specific antibodies, peptibodies, related proteins, and the like; c-Kit specific antibodies, peptibodies, related proteins, and the like, including but not limited to proteins that bind c-Kit and/or other stem cell factor receptors; OX40L specific antibodies, peptibodies, related proteins, and the like, including but not limited to proteins that bind OX40L and/or other ligands of the OX40 receptor; Activase® (alteplase, tPA); Aranesp® (darbepoetin alfa) Erythropoietin [30-asparagine, 32-threonine, 87-valine, 88-asparagine, 90-threonine], Darbepoetin alfa, novel erythropoiesis stimulating protein (NESP); Epogen® (epoetin alfa, or erythropoietin); GLP-1, Avonex® (interferon beta-1a); Bexxar® (tositumomab, anti-CD22 monoclonal antibody); Betaseron® (interferon-beta); Campath® (alemtuzumab, anti-CD52 monoclonal antibody); Dynepo® (epoetin delta); Velcade® (bortezomib); MLN0002 (anti-α4β7 mAb); MLN1202 (anti-CCR2 chemokine receptor mAb); Enbrel® (etanercept, TNF-receptor/Fc fusion protein, TNF blocker); Eprex® (epoetin alfa); Erbitux® (cetuximab, anti-EGFR/HER1/c-ErbB-1); Genotropin® (somatropin, Human Growth Hormone); Herceptin® (trastuzumab, anti-HER2/neu (erbB2) receptor mAb); Kanjinti™ (trastuzumab-anns) anti-HER2 monoclonal antibody, biosimilar to Herceptin®, or another product containing trastuzumab for the treatment of breast or gastric cancers; Humatrope® (somatropin, Human Growth Hormone); Humira® (adalimumab); Vectibix® (panitumumab), Xgeva® (denosumab), Prolia® (denosumab), Immunoglobulin G2 Human Monoclonal Antibody to RANK Ligand, Enbrel® (etanercept, TNF-receptor/Fc fusion protein, TNF blocker), Nplate® (romiplostim), rilotumumab, ganitumab, conatumumab, brodalumab, insulin in solution; Infergen® (interferon alfacon-1); Natrecor® (nesiritide; recombinant human B-type natriuretic peptide (hBNP); Kineret® (anakinra); Leukine® (sargamostim, rhuGM-CSF); LymphoCide® (epratuzumab, anti-CD22 mAb); Benlysta™ (lymphostat B, belimumab, anti-BlyS mAb); Metalyse® (tenecteplase, t-PA analog); Mircera® (methoxy polyethylene glycol-epoetin beta); Mylotarg® (gemtuzumab ozogamicin); Raptiva® (efalizumab); Cimzia® (certolizumab pegol, CDP 870); Soliris™ (eculizumab); pexelizumab (anti-C5 complement); Numax® (MEDI-524); Lucentis® (ranibizumab); Panorex® (17-1A, edrecolomab); Trabio® (lerdelimumab); TheraCim hR3 (nimotuzumab); Omnitarg (pertuzumab, 2C4); Osidem® (IDM-1); OvaRex® (B43.13); Nuvion® (visilizumab); cantuzumab mertansine (huC242-DM1); NeoRecormon® (epoetin beta); Neumega® (oprelvekin, human interleukin-11); Orthoclone OKT3® (muromonab-CD3, anti-CD3 monoclonal antibody); Procrit® (epoetin alfa); Remicade® (infliximab, anti-TNFα monoclonal antibody); ReoPro® (abciximab, anti-GP IIb/IIIa receptor monoclonal antibody); Actemra® (anti-IL6 Receptor mAb); Avastin® (bevacizumab), HuMax-CD4 (zanolimumab); Mvasi™ (bevacizumab-awwb); Rituxan® (rituximab, anti-CD20 mAb); Tarceva® (erlotinib); Roferon-A®-(interferon alfa-2a); Simulect® (basiliximab); Prexige® (lumiracoxib); Synagis® (palivizumab); 145c7-CHO (anti-IL15 antibody, see U.S. Pat. No. 7,153,507); Tysabri® (natalizumab, anti-α4integrin mAb); Valortim® (MDX-1303, anti-B. anthracis protective antigen mAb); ABthrax™; Xolair® (omalizumab); ETI211 (anti-MRSA mAb); IL-1 trap (the Fc portion of human IgG1 and the extracellular domains of both IL-1 receptor components (the Type I receptor and receptor accessory protein)); VEGF trap (Ig domains of VEGFR1 fused to IgG1 Fc); Zenapax® (daclizumab); Zenapax® (daclizumab, anti-IL-2Rα mAb); Zevalin® (ibritumomab tiuxetan); Zetia® (ezetimibe); Orencia® (atacicept, TACI-Ig); anti-CD80 monoclonal antibody (galiximab); anti-CD23 mAb (lumiliximab); BR2-Fc (huBR3/huFc fusion protein, soluble BAFF antagonist); CNTO 148 (golimumab, anti-TNFα mAb); HGS-ETR1 (mapatumumab; human anti-TRAIL Receptor-1 mAb);

HuMax-CD20 (ocrelizumab, anti-CD20 human mAb); HuMax-EGFR (zalutumumab); M200 (volociximab, anti-αβ1 integrin mAb); MDX-010 (ipilimumab, anti-CTLA-4 mAb and VEGFR-1 (IMC-18F1); anti-BR3 mAb; anti-C. difficile Toxin A and Toxin B C mAbs MDX-066 (CDA-1) and MDX-1388); anti-CD22 dsFv-PE38 conjugates (CAT-3888 and CAT-8015); anti-CD25 mAb (HuMax-TAC); anti-CD3 mAb (NI-0401); adecatumumab; anti-CD30 mAb (MDX-060); MDX-1333 (anti-IFNAR); anti-CD38 mAb (HuMax CD38); anti-CD40L mAb; anti-Cripto mAb; anti-CTGF Idiopathic Pulmonary Fibrosis Phase I Fibrogen (FG-3019); anti-CTLA4 mAb; anti-eotaxin1 mAb (CAT-213); anti-FGF8 mAb; anti-ganglioside GD2 mAb; anti-ganglioside GM2 mAb; anti-GDF-8 human mAb (MYO-029); anti-GM-CSF Receptor mAb (CAM-3001); anti-HepC mAb (HuMax HepC); anti-IFNα mAb (MEDI-545, MDX-198); anti-IGF1R mAb; anti-IGF-1R mAb (HuMax-Inflam); anti-IL12 mAb (ABT-874); anti-IL12/IL23 mAb (CNTO 1275); anti-IL13 mAb (CAT-354); anti-IL2Ra mAb (Hu-Max-TAC); anti-IL5 Receptor mAb; anti-integrin receptors mAb (MDX-018, CNTO 95); anti-IP10 Ulcerative Colitis mAb (MDX-1100); BMS-66513; anti-Mannose Receptor/hCGβ mAb (MDX-1307); anti-mesothelin dsFv-PE38 conjugate (CAT-5001); anti-PD1mAb (MDX-1106 (ONO-4538)); anti-PDGFRα antibody (IMC-3G3); anti-TGFß mAb (GC-1008); anti-TRAIL Receptor-2 human mAb (HGS-ETR2); anti-TWEAK mAb; anti-VEGFR/Flt-1 mAb; and anti-ZP3 mAb (HuMax-ZP3).

In some embodiments, the drug delivery device may contain or be used with a sclerostin antibody, such as but not limited to romosozumab, blosozumab, BPS 804 (Novartis), Evenity™ (romosozumab-aqqg), another product containing romosozumab for treatment of postmenopausal osteoporosis and/or fracture healing and in other embodiments, a monoclonal antibody (IgG) that binds human Proprotein Convertase Subtilisin/Kexin Type 9 (PCSK9). Such PCSK9 specific antibodies include, but are not limited to, Repatha® (evolocumab) and Praluent® (alirocumab). In other embodiments, the drug delivery device may contain or be used with rilotumumab, bixalomer, trebananib, ganitumab, conatumumab, motesanib diphosphate, brodalumab, vidupiprant or panitumumab. In some embodiments, the reservoir of the drug delivery device may be filled with or the device can be used with IMLYGIC® (talimogene laherparepvec) or another oncolytic HSV for the treatment of melanoma or other cancers including but not limited to OncoV-EXGALV/CD; OrienX010; G207, 1716; NV1020; NV12023; NV1034; and NV1042. In some embodiments, the drug delivery device may contain or be used with endogenous tissue inhibitors of metalloproteinases (TIMPs) such as but not limited to TIMP-3. In some embodiments, the drug delivery device may contain or be used with Aimovig® (erenumab-aooe), anti-human CGRP-R (calcitonin gene-related peptide type 1 receptor) or another product containing erenumab for the treatment of migraine headaches. Antagonistic antibodies for human calcitonin gene-related peptide (CGRP) receptor such as but not limited to erenumab and bispecific antibody molecules that target the CGRP receptor and other headache targets may also be delivered with a drug delivery device of the present disclosure. Additionally, bispecific T cell engager (BiTE®) antibodies such as but not limited to BLINCYTO® (blinatumomab) can be used in or with the drug delivery device of the present disclosure. In some embodiments, the drug delivery device may contain or be used with an APJ large molecule agonist such as but not limited to apelin or analogues thereof. In some embodiments, a therapeutically effective amount of an anti-thymic stromal lymphopoietin (TSLP) or TSLP receptor antibody is used in or with the drug delivery device of the present disclosure. In some embodiments, the drug delivery device may contain or be used with Avsola™ (infliximab-axxq), anti-TNF α monoclonal antibody, biosimilar to Remicade® (infliximab) (Janssen Biotech, Inc.) or another product containing infliximab for the treatment of autoimmune diseases. In some embodiments, the drug delivery device may contain or be used with Kyprolis® (carfilzomib), (2S)—N—((S)-1-(S)-4-methyl-1-((R)-2-methyloxiran-2-yl)-1-oxopentan-2-ylcarbamoyl)-2-phenylethyl)-2-((S)-2-(2-morpholinoacetamido)-4-phenylbutanamido)-4-methylpentanamide, or another product containing carfilzomib for the treatment of multiple myeloma. In some embodiments, the drug delivery device may contain or be used with Otezla® (apremilast), N-[2-[(1S)-1-(3-ethoxy-4-methoxyphenyl)-2-(methylsulfonyl)ethyl]-2,3-dihydro-1,3-dioxo-1H-isoindol-4-yl]acetamide, or another product containing apremilast for the treatment of various inflammatory diseases. In some embodiments, the drug delivery device may contain or be used with Parsabiv™ (etelcalcetide HCl, KAI-4169) or another product containing etelcalcetide HCl for the treatment of secondary hyperparathyroidism (sHPT) such as in patients with chronic kidney disease (KD) on hemodialysis. In some embodiments, the drug delivery device may contain or be used with ABP 798 (rituximab), a biosimilar candidate to Rituxan®/MabThera™, or another product containing an anti-CD20 monoclonal antibody. In some embodiments, the drug delivery device may contain or be used with a VEGF antagonist such as a non-antibody VEGF antagonist and/or a VEGF-Trap such as aflibercept (Ig domain 2 from VEGFR1 and Ig domain 3 from VEGFR2, fused to Fc domain of IgG1). In some embodiments, the drug delivery device may contain or be used with ABP 959 (eculizumab), a biosimilar candidate to Soliris®, or another product containing a monoclonal antibody that specifically binds to the complement protein C5. In some embodiments, the drug delivery device may contain or be used with Rozibafusp alfa (formerly AMG 570) is a novel bispecific antibody-peptide conjugate that simultaneously blocks ICOSL and BAFF activity. In some embodiments, the drug delivery device may contain or be used with Omecamtiv mecarbil, a small molecule selective cardiac myosin activator, or myotrope, which directly targets the contractile mechanisms of the heart, or another product containing a small molecule selective cardiac myosin activator. In some embodiments, the drug delivery device may contain or be used with Sotorasib (formerly known as AMG 510), a $KRAS^{G12C}$ small molecule inhibitor, or another product containing a $KRAS^{G12C}$ small molecule inhibitor. In some embodiments, the drug delivery device may contain or be used with Tezepelumab, a human monoclonal antibody that inhibits the action of thymic stromal lymphopoietin (TSLP), or another product containing a human monoclonal antibody that inhibits the action of TSLP. In some embodiments, the drug delivery device may contain or be used with AMG 714, a human monoclonal antibody that binds to Interleukin-15 (IL-15) or another product containing a human monoclonal antibody that binds to Interleukin-15 (IL-15). In some embodiments, the drug delivery device may contain or be used with AMG 890, a small interfering RNA (siRNA) that lowers lipoprotein(a), also known as Lp(a), or another product containing a small interfering RNA (siRNA) that lowers lipoprotein(a). In some embodiments, the drug delivery device may contain or be used with ABP 654 (human IgG1 kappa antibody), a biosimilar candidate to Stelara®, or another product that contains human IgG1 kappa antibody and/or binds to the p40 subunit of human cytokines interleukin (IL)-12 and IL-23. In some embodiments, the drug delivery device may contain or be used with Amjevita™ or Amgevita™ (formerly ABP 501) (mab anti-TNF human IgG1), a biosimilar candidate to Humira®, or another product that contains human mab anti-TNF human IgG1. In some embodiments, the drug delivery device may contain or be used with AMG 160, or another product that contains a half-life extended (HLE) anti-prostate-specific membrane antigen (PSMA) x anti-CD3 BiTE® (bispecific T cell engager) construct. In some embodiments, the drug delivery device may contain or be used with AMG 119, or another product containing a delta-like ligand 3 (DLL3) CART (chimeric antigen receptor T cell) cellular therapy. In some embodiments, the drug delivery device may contain or be used with AMG 119, or another product containing a delta-like ligand 3 (DLL3) CAR T (chimeric antigen receptor T cell) cellular therapy. In some embodiments, the drug delivery device may contain or be used with AMG 133, or another product containing a gastric inhibitory polypeptide receptor (GIPR) antagonist and GLP-1R agonist. In some embodiments, the drug delivery device may contain or be used with AMG 171 or another product containing a Growth Differential Factor 15 (GDF15) analog. In some embodiments, the drug delivery device may contain or be used with AMG 176 or another product containing a small molecule inhibitor of myeloid cell leukemia 1 (MCL-1). In some embodiments, the drug delivery device may contain or be used with AMG 199 or another product containing a half-life extended (HLE) bispecific T cell engager construct (BiTE®). In some embodiments, the drug delivery device may contain or be used with AMG 256 or another product containing an anti-PD-1 x IL21 mutein and/or an IL-21 receptor agonist designed to selectively turn on the Interleukin 21 (IL-21) pathway in programmed cell death-1 (PD-1) positive cells. In some embodiments, the drug delivery device may contain or be used with AMG 330 or another product containing an anti-CD33 x anti-CD3 BiTE® (bispecific T cell engager) construct. In some embodiments, the drug delivery device may contain or be used with AMG 404 or another product containing a human anti-programmed cell death-1 (PD-1) monoclonal antibody being investigated as a treatment for patients with solid tumors. In some embodiments, the drug delivery device may contain or be used with AMG 427 or another product containing a half-life extended (HLE) anti-fms-like tyrosine kinase 3 (FLT3) x anti-CD3 BiTE® (bispecific T cell engager) construct. In some embodiments, the drug delivery device may contain or be used with AMG 430 or another product containing an anti-Jagged-1 monoclonal antibody. In some embodiments, the drug delivery device may contain or be used with AMG 506 or another product containing a multi-specific FAP x 4-1BB-targeting DARPin® biologic under investigation as a treatment for solid tumors. In some embodiments, the drug delivery device may contain or be used with AMG 509 or another product containing a bivalent T-cell engager and is designed using XmAb® 2+1 technology. In some embodiments, the drug delivery device may contain or be used with AMG 562 or another product containing a half-life extended (HLE) CD19 x CD3 BiTE® (bispecific T cell engager) construct. In some embodiments, the drug delivery device may contain or be used with Efavaleukin alfa (formerly AMG 592) or another product containing an IL-2 mutein Fc fusion protein. In some embodiments, the drug delivery device may contain or be used with AMG 596 or another product containing a CD3 x epidermal growth factor receptor vIII (EGFRvIII) BiTE® (bispecific T cell engager) molecule. In some embodiments, the drug delivery device may contain or be used with AMG 673 or another product containing a half-life extended (HLE) anti-CD33 x anti-CD3 BiTE® (bispecific T cell engager) construct. In some embodiments, the drug delivery device may contain or be used with AMG 701 or another product containing a half-life extended (HLE) anti-B-cell maturation antigen (BCMA) x anti-CD3 BiTE® (bispecific T cell engager) construct. In some embodiments, the drug delivery device may contain or be used with AMG 757 or another product containing a half-life extended (HLE) anti-delta-like ligand 3 (DLL3) x anti-CD3 BiTE® (bispecific T cell engager) construct. In some embodiments, the drug delivery device may contain or be used with AMG 910 or another product containing a half-life extended (HLE) epithelial cell tight junction protein claudin 18.2 x CD3 BiTE® (bispecific T cell engager) construct.

Although the drug delivery devices, assemblies, components, subsystems and methods have been described in terms of exemplary embodiments, they are not limited thereto. The detailed description is to be construed as exemplary only and does not describe every possible embodiment of the present disclosure. Numerous alternative embodiments could be implemented, using either current technology or technology developed after the filing date of this patent that would still fall within the scope of the claims defining the invention(s) disclosed herein.

Those skilled in the art will recognize that a wide variety of modifications, alterations, and combinations can be made with respect to the above described embodiments without departing from the spirit and scope of the invention(s) disclosed herein, and that such modifications, alterations, and combinations are to be viewed as being within the ambit of the inventive concept(s).

What is claimed is:

1. A drug delivery device comprising:
    a housing defining a longitudinal axis and having an opening;
    a drug storage container including a delivery member having an insertion end configured to extend at least partially through the opening during a delivery state;
    a plunger moveable toward a distal end of the drug storage container to expel a drug from the drug storage container through the delivery member, the plunger including a top portion at a proximal end, a base at a distal end, and a body portion connecting the top portion and the base, wherein the body portion has an inner wall defining an axial chamber and an outer wall cooperating with the inner wall to define a body thickness less than 2 millimeters; and
    a plunger biasing member disposed at least partially within the axial chamber, the plunger biasing member being configured to urge the plunger toward the distal end of the drug storage container, wherein the base of the plunger is configured to support a distal end of the plunger biasing member.

2. The drug delivery device of claim 1, wherein the body thickness is less than 1 millimeter.

3. The drug delivery device of claim 1, wherein the body thickness is less than 0.6 millimeters.

4. The drug delivery device of claim 1, wherein the body thickness is less than 0.4 millimeters.

5. The drug delivery device of claim 1, wherein the body thickness is less than 0.3 millimeters.

6. The drug delivery device of claim 1, wherein the body thickness is less than 0.2 millimeters.

7. The drug delivery device of claim 1, wherein the body thickness is less than 0.1 millimeters.

8. The drug delivery device of claim 1, wherein the body thickness is less than 0.05 millimeters.

9. The drug delivery device of claim 1, wherein the body portion is made of metal.

10. The drug delivery device of claim 1, wherein the body portion is made of a non-metal.

11. The drug delivery device of claim 1, further comprising a plunger guide fixed relative to the housing, the plunger being disposed at least partially within the plunger guide.

12. The drug delivery device of claim 11, wherein one of the plunger and the plunger guide comprises a cam and the other one of the plunger and the plunger guide comprises a cam follower.

13. The drug delivery device of claim 12, wherein the plunger includes the cam follower and the plunger guide includes the cam, and wherein the cam follower is formed by at least one flange extending radially outwardly from the plunger.

14. The drug delivery device of claim 1, wherein the drug storage container is filled or pre-filled with the drug, and wherein the drug comprises one of: a drug containing a human IgG1 kappa antibody, a drug containing a small interfering RNA (siRNA) that lowers lipoprotein (a), efavaleukin alfa, evolocumab, and a drug containing a gastric inhibitory polypeptide receptor (GIPR) antagonist and a GLP-1R agonist.

15. A drug delivery device comprising:
   a housing defining a longitudinal axis and having an opening;
   a drug storage container including a delivery member having an insertion end configured to extend at least partially through the opening during a delivery state;
   a plunger moveable toward a distal end of the drug storage container to expel a drug from the drug storage container through the delivery member, the plunger including a top portion at a proximal end, a base at a distal end, and a hollow rod connecting the top portion and the base, wherein the hollow rod has an annular wall having an inner surface defining an interior space and an outer surface cooperating with the inner surface to define a thickness of the annular wall of less than 2 millimeters; and
   a plunger biasing member disposed at least partially within the interior space, the plunger biasing member being configured to urge the plunger toward the distal end of the drug storage container, wherein the base of the plunger is configured to support a distal end of the plunger biasing member.

16. The drug delivery device of claim 15, wherein the thickness of the annular wall of the plunger is less than 1 millimeter.

17. The drug delivery device of claim 15, wherein the thickness of the annular wall of the plunger is less than 0.6 millimeters.

18. The drug delivery device of claim 15, wherein the thickness of the annular wall of the plunger is less than 0.4 millimeters.

19. The drug delivery device of claim 15, wherein the thickness of the annular wall of the plunger is less than 0.3 millimeters.

20. The drug delivery device of claim 15, wherein the thickness of the annular wall of the plunger is less than 0.2 millimeters.

21. The drug delivery device of claim 15, wherein the drug storage container is filled or pre-filled with the drug, and wherein the drug comprises one of: a drug containing a human IgG1 kappa antibody, a drug containing a small interfering RNA (siRNA) that lowers lipoprotein (a), efavaleukin alfa, evolocumab, and a drug containing a gastric inhibitory polypeptide receptor (GIPR) antagonist and a GLP-1R agonist.

22. The drug delivery device of claim 15, wherein the thickness of the annular wall of the plunger is less than 0.1 millimeters.

23. The drug delivery device of claim 15, wherein the thickness of the annular wall of the plunger is less than 0.05 millimeters.

24. The drug delivery device of claim 15, wherein the hollow rod is made of metal.

25. The drug delivery device of claim 15, wherein the hollow rod is made of a non-metal.

* * * * *